United States Patent
Dihora et al.

(10) Patent No.: US 12,133,906 B2
(45) Date of Patent: *Nov. 5, 2024

(54) DELIVERY PARTICLE

(71) Applicant: The Procter & Gamble Company, Cincinnati, OH (US)

(72) Inventors: Jiten Odhavji Dihora, Liberty Township, OH (US); Johan Smets, Lubbeek (BE); Todd Arlin Schwantes, Lena, WI (US)

(73) Assignee: The Procter & Gamble Company, Cincinnati, OH (US)

( * ) Notice: Subject to any disclaimer, the term of this patent is extended or adjusted under 35 U.S.C. 154(b) by 21 days.

This patent is subject to a terminal disclaimer.

(21) Appl. No.: 17/408,646

(22) Filed: Aug. 23, 2021

(65) Prior Publication Data

US 2022/0409497 A1 Dec. 29, 2022

Related U.S. Application Data

(63) Continuation of application No. 16/246,568, filed on Jan. 14, 2019, now Pat. No. 11,096,875, which is a continuation of application No. 14/543,432, filed on Nov. 17, 2014, now abandoned, which is a continuation of application No. 12/777,301, filed on May 11, 2010, now Pat. No. 9,186,642.

(60) Provisional application No. 61/328,949, filed on Apr. 28, 2010.

(51) Int. Cl.
| | | |
|---|---|---|
| *A61K 8/11* | (2006.01) | |
| *A61K 8/81* | (2006.01) | |
| *A61Q 5/02* | (2006.01) | |
| *A61Q 5/12* | (2006.01) | |
| *A61Q 13/00* | (2006.01) | |
| *A61Q 15/00* | (2006.01) | |
| *A61Q 19/00* | (2006.01) | |
| *A61Q 19/10* | (2006.01) | |
| *B01J 13/18* | (2006.01) | |
| *C09B 67/02* | (2006.01) | |
| *C11D 3/37* | (2006.01) | |
| *C11D 3/50* | (2006.01) | |
| *C11D 17/00* | (2006.01) | |
| *D06M 23/12* | (2006.01) | |

(52) U.S. Cl.
CPC .............. *A61K 8/11* (2013.01); *A61K 8/8147* (2013.01); *A61Q 5/02* (2013.01); *A61Q 5/12* (2013.01); *A61Q 13/00* (2013.01); *A61Q 15/00* (2013.01); *A61Q 19/00* (2013.01); *A61Q 19/10* (2013.01); *B01J 13/185* (2013.01); *C09B 67/0097* (2013.01); *C11D 3/3757* (2013.01); *C11D 3/505* (2013.01); *C11D 17/0039* (2013.01); *D06M 23/12* (2013.01); *A61K 2800/10* (2013.01); *A61K 2800/412* (2013.01); *A61K 2800/56* (2013.01); *A61K 2800/654* (2013.01)

(58) Field of Classification Search
None
See application file for complete search history.

(56) References Cited

U.S. PATENT DOCUMENTS

| | | |
|---|---|---|
| 2,396,278 A | 3/1946 | Otto |
| 2,438,091 A | 3/1948 | Lynch |
| 2,486,921 A | 11/1949 | Byerly |
| 2,486,922 A | 11/1949 | Bruce |
| 2,528,378 A | 10/1950 | McCabe, Jr. |
| 2,658,072 A | 11/1953 | Kosmin |
| 2,730,456 A | 1/1956 | Green |
| 2,730,457 A | 1/1956 | Green |
| 2,800,457 A | 7/1957 | Green |
| 2,800,458 A | 7/1957 | Green |
| 2,809,971 A | 10/1957 | Jack |
| 2,826,551 A | 3/1958 | Geen |
| RE24,899 E | 11/1960 | Green |
| 3,236,733 A | 2/1966 | Karsten |
| 3,332,880 A | 7/1967 | Adriaan |
| 3,429,827 A | 2/1969 | Ruus |
| 3,516,941 A | 6/1970 | Matson |
| 3,660,304 A | 5/1972 | Matsukawa |
| 3,681,248 A | 8/1972 | Gould |
| 3,691,140 A | 9/1972 | Silver |
| 3,753,196 A | 8/1973 | Kurtz |
| 3,761,418 A | 9/1973 | Parran |
| 3,772,215 A | 11/1973 | Gould |

(Continued)

FOREIGN PATENT DOCUMENTS

| | | |
|---|---|---|
| AU | 2616292 A | 4/1993 |
| CA | 2306397 A1 | 10/2000 |

(Continued)

OTHER PUBLICATIONS

"Aluminum Silicate Powder from READE", retrieved on Jul. 23, 2014, pp. 1-2.

(Continued)

*Primary Examiner* — H. Sarah Park
(74) *Attorney, Agent, or Firm* — Gregory S. Darley-Emerson; Andrew J. Mueller; George H. Leal

(57) ABSTRACT

The present application relates to encapsulated benefit agents, compositions comprising such encapsulated benefit agents and processes for making and using compositions comprising such encapsulated benefit agents. Such encapsulated benefit agents eliminate or minimize one or more of the drawbacks of current encapsulated benefit agents and thus provide formulators with additional perfume delivery opportunities.

17 Claims, No Drawings

(56) References Cited

U.S. PATENT DOCUMENTS

| | | |
|---|---|---|
| 3,826,756 A | 7/1974 | Bachmann |
| 3,886,085 A | 5/1975 | Kiritani |
| 3,898,039 A | 8/1975 | Lin |
| 3,920,819 A | 11/1975 | Stephens |
| 3,929,678 A | 12/1975 | Laughlin et al. |
| 3,958,581 A | 5/1976 | Abegg |
| 3,962,418 A | 6/1976 | Birkofer |
| 3,964,500 A | 6/1976 | Drakoff |
| 3,965,033 A | 6/1976 | Matsukawa |
| 4,001,140 A | 1/1977 | Foris |
| 4,046,750 A | 9/1977 | Rembaum |
| 4,062,799 A | 12/1977 | Matsukawa |
| 4,075,134 A | 2/1978 | Morehouse, Jr. |
| 4,081,376 A | 3/1978 | Strub |
| 4,087,376 A | 5/1978 | Foris |
| 4,089,802 A | 5/1978 | Foris |
| 4,093,556 A | 6/1978 | Wojciak |
| 4,100,103 A | 7/1978 | Foris |
| 4,105,823 A | 8/1978 | Hasler |
| 4,145,184 A | 3/1979 | Brain |
| 4,166,152 A | 8/1979 | Baker |
| 4,183,911 A | 1/1980 | Smithies |
| 4,197,346 A | 4/1980 | Stevens |
| 4,197,865 A | 4/1980 | Jacquet |
| 4,217,914 A | 8/1980 | Jacquet |
| 4,221,710 A | 9/1980 | Hoshi |
| 4,234,627 A | 11/1980 | Schilling |
| 4,240,450 A | 12/1980 | Cauwet |
| 4,247,411 A | 1/1981 | Vanlerberghe |
| 4,251,386 A | 2/1981 | Saeki |
| 4,254,201 A | 3/1981 | Sawai et al. |
| 4,275,055 A | 6/1981 | Nachtigal |
| 4,285,720 A | 8/1981 | Scher |
| 4,323,683 A | 4/1982 | Bolich, Jr. |
| 4,345,080 A | 8/1982 | Bolich, Jr. |
| 4,356,109 A | 10/1982 | Saeki |
| 4,364,837 A | 12/1982 | Pader |
| 4,379,753 A | 4/1983 | Bolich, Jr. |
| 4,381,919 A | 5/1983 | Jacquet |
| 4,422,853 A | 12/1983 | Jacquet |
| 4,423,099 A | 12/1983 | Mueller |
| 4,428,869 A | 1/1984 | Munteanu |
| 4,430,243 A | 2/1984 | Bragg |
| 4,444,699 A | 4/1984 | Hayford |
| 4,446,032 A | 5/1984 | Munteanu |
| 4,450,123 A | 5/1984 | Egawa |
| 4,470,982 A | 9/1984 | Winkler |
| 4,507,280 A | 3/1985 | Pohl |
| 4,515,705 A | 5/1985 | Moeddel |
| 4,529,586 A | 7/1985 | De Marco et al. |
| 4,537,706 A | 8/1985 | Severson, Jr. |
| 4,537,707 A | 8/1985 | Severson, Jr. |
| 4,547,429 A | 10/1985 | Greiner |
| 4,550,862 A | 11/1985 | Barker |
| 4,552,811 A | 11/1985 | Brown |
| 4,561,997 A | 12/1985 | Roehl |
| 4,561,998 A | 12/1985 | Wertz |
| 4,574,110 A | 3/1986 | Asano |
| 4,588,639 A | 5/1986 | Ozono |
| 4,597,898 A | 7/1986 | Vander Meer |
| 4,601,863 A | 7/1986 | Shioi |
| 4,608,250 A | 8/1986 | Jacquet |
| 4,610,927 A | 9/1986 | Igarashi |
| 4,622,267 A | 11/1986 | Riecke |
| 4,663,158 A | 5/1987 | Wolfram |
| 4,708,924 A | 11/1987 | Nagai |
| 4,719,099 A | 1/1988 | Grollier |
| 4,722,865 A | 2/1988 | Huizer |
| 4,741,855 A | 5/1988 | Grote |
| 4,746,467 A | 5/1988 | Sakamoto |
| 4,754,110 A | 6/1988 | Craft |
| 4,775,656 A | 10/1988 | Harada |
| 4,780,370 A | 10/1988 | Pointier |
| 4,798,691 A | 1/1989 | Kasai |
| 4,803,947 A | 2/1989 | Ueki |
| 4,824,707 A | 4/1989 | Spector |
| 4,863,626 A | 9/1989 | Coyne |
| 4,865,759 A | 9/1989 | Coyne |
| 4,882,220 A | 11/1989 | Ono |
| 4,908,271 A | 3/1990 | Kasai |
| 4,911,851 A | 3/1990 | Ladd, Jr. |
| 4,917,920 A | 4/1990 | Ono |
| 4,919,841 A | 4/1990 | Kamel |
| 4,946,624 A | 8/1990 | Michael |
| 4,957,666 A | 9/1990 | Kawamura |
| 4,968,451 A | 11/1990 | Scheibel |
| 4,972,000 A | 11/1990 | Kawashima |
| 5,009,880 A | 4/1991 | Grollier |
| 5,061,410 A | 10/1991 | Sakamoto |
| 5,066,419 A | 11/1991 | Walley |
| 5,071,706 A | 12/1991 | Soper |
| 5,104,646 A | 4/1992 | Bolich, Jr. |
| 5,105,823 A | 4/1992 | Blum |
| 5,106,609 A | 4/1992 | Bolich, Jr. |
| 5,113,585 A | 5/1992 | Rogers |
| 5,118,756 A | 6/1992 | Asano |
| 5,120,349 A | 6/1992 | Stewart |
| 5,137,646 A | 8/1992 | Schmidt et al. |
| 5,145,675 A | 9/1992 | Won |
| 5,176,903 A | 1/1993 | Goldberg |
| 5,185,155 A | 2/1993 | Behan |
| 5,188,753 A | 2/1993 | Schmidt |
| 5,225,278 A | 7/1993 | Kielbania, Jr. |
| 5,232,613 A | 8/1993 | Bacon |
| 5,232,769 A | 8/1993 | Yamato |
| 5,234,611 A | 8/1993 | Trinh |
| 5,234,682 A | 8/1993 | Macchio |
| 5,277,979 A | 1/1994 | Kielbania, Jr. |
| 5,278,106 A | 1/1994 | Nakashima |
| 5,292,835 A | 3/1994 | Jahns |
| RE34,584 E | 4/1994 | Grote |
| 5,324,444 A | 6/1994 | Berry |
| 5,342,556 A | 8/1994 | Traeubel |
| 5,362,565 A | 11/1994 | Murano |
| 5,366,652 A | 11/1994 | Capeci |
| 5,370,881 A | 12/1994 | Fuisz |
| 5,380,756 A | 1/1995 | Andrews |
| 5,399,192 A | 3/1995 | Yamasoe |
| 5,407,609 A | 4/1995 | Tice |
| 5,468,473 A | 11/1995 | Mullen |
| 5,486,303 A | 1/1996 | Capeci |
| 5,487,884 A | 1/1996 | Bissett |
| 5,489,392 A | 2/1996 | Capeci |
| 5,516,448 A | 5/1996 | Capeci |
| 5,565,145 A | 10/1996 | Watson |
| 5,565,422 A | 10/1996 | Del Greco et al. |
| 5,569,645 A | 10/1996 | Dinniwell |
| 5,573,756 A | 11/1996 | Lambrechts |
| 5,574,005 A | 11/1996 | Welch |
| 5,575,282 A | 11/1996 | Knoch |
| 5,576,282 A | 11/1996 | Miracle |
| 5,580,578 A | 12/1996 | Oshlack |
| 5,595,967 A | 1/1997 | Miracle |
| 5,596,051 A | 1/1997 | Jahns |
| 5,597,936 A | 1/1997 | Perkins |
| 5,607,980 A | 3/1997 | Mcatee |
| 5,611,972 A | 3/1997 | Tararuj |
| 5,637,401 A | 6/1997 | Berman |
| 5,648,328 A | 7/1997 | Angell |
| 5,652,228 A | 7/1997 | Bissett |
| 5,656,584 A | 8/1997 | Angell |
| 5,674,478 A | 10/1997 | Dodd |
| 5,681,852 A | 10/1997 | Bissett |
| 5,691,297 A | 11/1997 | Nassano |
| 5,702,714 A | 12/1997 | Goss |
| 5,716,938 A | 2/1998 | Provitt |
| 5,723,420 A | 3/1998 | Wei |
| 5,725,869 A | 3/1998 | Lo |
| 5,750,122 A | 5/1998 | Evans |
| 5,756,436 A | 5/1998 | Royce |
| 5,759,573 A | 6/1998 | Kim |
| 5,782,409 A | 7/1998 | Paul |
| 5,783,536 A | 7/1998 | Farrell |
| 5,800,805 A | 9/1998 | Salas |

(56) References Cited

U.S. PATENT DOCUMENTS

| | | |
|---|---|---|
| 5,807,956 A | 9/1998 | Czech |
| 5,827,538 A | 10/1998 | Cussler |
| 5,833,971 A | 11/1998 | Baldwin |
| 5,856,409 A | 1/1999 | Ziemelis |
| 5,876,755 A | 3/1999 | Perring |
| 5,879,584 A | 3/1999 | Bianchetti |
| 5,885,701 A | 3/1999 | Berman |
| 5,929,022 A | 7/1999 | Velazquez |
| 5,945,085 A | 8/1999 | Salas |
| 5,962,018 A | 10/1999 | Curtis |
| 5,972,859 A | 10/1999 | Farrell |
| 5,981,681 A | 11/1999 | Czech |
| 6,024,943 A | 2/2000 | Ness |
| D424,745 S | 5/2000 | Tseng |
| 6,075,003 A | 6/2000 | Haq |
| 6,147,037 A | 11/2000 | Gardlik |
| 6,159,485 A | 12/2000 | Yu |
| 6,182,365 B1 | 2/2001 | Tseng |
| 6,185,822 B1 | 2/2001 | Tseng |
| 6,194,375 B1 | 2/2001 | Ness |
| 6,207,782 B1 | 3/2001 | Czech |
| 6,221,326 B1 | 4/2001 | Amiche |
| 6,221,826 B1 | 4/2001 | Surutzidis |
| 6,225,464 B1 | 5/2001 | Hiler, II |
| 6,228,398 B1 | 5/2001 | Devane |
| 6,235,274 B1 | 5/2001 | Lou |
| 6,235,773 B1 | 5/2001 | Bissett |
| 6,245,366 B1 | 6/2001 | Popplewell |
| 6,245,733 B1 | 6/2001 | Mosbaugh |
| 6,248,364 B1 | 6/2001 | Sengupta |
| 6,258,857 B1 | 7/2001 | Iijima |
| 6,261,483 B1 | 7/2001 | Frank |
| 6,294,514 B1 | 9/2001 | Welling |
| 6,298,558 B1 | 10/2001 | Tseng |
| 6,306,812 B1 | 10/2001 | Perkins |
| 6,325,995 B1 | 12/2001 | El-nokaly |
| 6,326,348 B1 | 12/2001 | Vinson |
| 6,329,057 B1 | 12/2001 | Dungworth |
| 6,348,218 B1 | 2/2002 | Hed |
| 6,362,159 B1 | 3/2002 | Aguadisch |
| 6,368,633 B1 | 4/2002 | Lou |
| 6,375,872 B1 | 4/2002 | Chao |
| 6,375,983 B1 | 4/2002 | Kantor |
| 6,376,445 B1 | 4/2002 | Bettiol |
| 6,399,192 B1 | 6/2002 | Pinna |
| 6,413,548 B1 | 7/2002 | Hamer |
| 6,428,796 B1 | 8/2002 | Gers-barlag |
| 6,451,754 B1 | 9/2002 | Rowland |
| 6,482,969 B1 | 11/2002 | Helmrick |
| 6,489,047 B2 | 12/2002 | Mosbaugh |
| 6,498,135 B1 | 12/2002 | Angell |
| 6,503,495 B1 | 1/2003 | Alwattari |
| 6,524,564 B1 | 2/2003 | Kim |
| 6,531,156 B1 | 3/2003 | Clark |
| 6,550,092 B1 | 4/2003 | Brown |
| 6,558,706 B2 | 5/2003 | Kantor |
| 6,592,990 B2 | 7/2003 | Schwantes |
| 6,594,904 B1 | 7/2003 | Tseng |
| 6,607,717 B1 | 8/2003 | Johnson |
| 6,608,017 B1 | 8/2003 | Dihora |
| 6,638,591 B2 | 10/2003 | Bowen |
| 6,670,311 B1 | 12/2003 | Aldcroft |
| 6,682,749 B1 | 1/2004 | Potechin |
| 6,696,049 B2 | 2/2004 | Vatter |
| 6,696,400 B2 | 2/2004 | Puelle |
| 6,703,032 B2 | 3/2004 | Gers-barlag |
| 6,730,325 B2 | 5/2004 | Devane |
| 6,733,790 B2 | 5/2004 | Garces |
| 6,767,880 B1 | 7/2004 | Foley |
| 6,769,271 B2 | 8/2004 | Mosbaugh |
| 6,770,293 B2 | 8/2004 | Angel |
| 6,780,507 B2 | 8/2004 | Toreki |
| 6,783,770 B2 | 8/2004 | Angel |
| 6,790,814 B1 | 9/2004 | Marin |
| 6,793,936 B2 | 9/2004 | Devane |
| 6,797,683 B2 | 9/2004 | Shana |
| 6,800,598 B1 | 10/2004 | Waeschenbach |
| 6,806,249 B2 | 10/2004 | Yang |
| 6,846,785 B2 | 1/2005 | Patel |
| 6,849,584 B2 | 2/2005 | Geary |
| 6,849,591 B1 | 2/2005 | Boeckh |
| 6,864,223 B2 | 3/2005 | Smith |
| 6,869,923 B1 | 3/2005 | Cunningham |
| 6,872,853 B1 | 3/2005 | Van Der Schaaf et al. |
| 6,881,482 B2 | 4/2005 | Vasisht |
| 6,902,742 B2 | 6/2005 | Devane |
| 6,916,481 B1 | 7/2005 | Prud |
| 6,939,992 B2 | 9/2005 | Van Der Schaaf et al. |
| 6,944,952 B1 | 9/2005 | Tseng |
| 6,951,836 B2 | 10/2005 | Jahns |
| 6,955,823 B2 | 10/2005 | Casson |
| 6,958,313 B2 | 10/2005 | Caswell |
| 6,982,256 B2 | 1/2006 | Votteler |
| 7,015,186 B2 | 3/2006 | Aussant |
| 7,041,767 B2 | 5/2006 | Lange |
| 7,053,034 B2 | 5/2006 | Shefer |
| 7,069,658 B2 | 7/2006 | Tseng |
| 7,105,064 B2 | 9/2006 | Popplewell |
| 7,119,057 B2 | 10/2006 | Popplewell |
| 7,122,512 B2 | 10/2006 | Brain |
| 7,125,835 B2 | 10/2006 | Bennett |
| 7,137,570 B2 | 11/2006 | Wheatley |
| 7,159,792 B2 | 1/2007 | Wheatley |
| 7,186,679 B2 | 3/2007 | Shepherd, Jr. |
| 7,186,680 B2 | 3/2007 | Caswell |
| 7,192,599 B2 | 3/2007 | Mercier |
| 7,196,049 B2 | 3/2007 | Brain |
| 7,204,998 B2 | 4/2007 | Holzner |
| 7,208,463 B2 | 4/2007 | Heltovics |
| 7,208,465 B2 | 4/2007 | Heltovics |
| 7,211,273 B2 | 5/2007 | Hsu |
| 7,211,556 B2 | 5/2007 | Heibel |
| 7,217,777 B2 | 5/2007 | Lange |
| 7,226,607 B2 | 6/2007 | Uchiyama |
| 7,229,611 B2 | 6/2007 | Zamudio-tena |
| 7,235,261 B2 | 6/2007 | Smith |
| 7,241,835 B2 | 7/2007 | Obrien |
| 7,247,374 B2 | 7/2007 | Haggquist |
| 7,270,828 B2 | 9/2007 | Masuda |
| 7,279,542 B2 | 10/2007 | Ouali |
| 7,293,719 B2 | 11/2007 | Wheatley |
| 7,294,612 B2 | 11/2007 | Popplewell |
| 7,311,900 B2 | 12/2007 | Conover |
| 7,338,928 B2 | 3/2008 | Lau |
| 7,375,875 B2 | 5/2008 | Whitesides |
| 7,381,417 B2 | 6/2008 | Gamez-garcia |
| 7,399,324 B2 | 7/2008 | Roddenbery |
| 7,407,650 B2 | 8/2008 | Heltovics |
| 7,413,731 B2 | 8/2008 | Heltovics |
| 7,442,838 B2 | 10/2008 | Van Der Schaaf et al. |
| 7,452,547 B2 | 11/2008 | Lambino |
| 7,465,439 B2 | 12/2008 | Avery |
| 7,491,687 B2 | 2/2009 | Popplewell |
| 7,521,124 B2 | 4/2009 | Ahn |
| 7,524,807 B2 | 4/2009 | Clapp |
| 7,532,388 B2 | 5/2009 | Whitesides |
| 7,538,077 B2 | 5/2009 | Sichmann |
| 7,538,078 B2 | 5/2009 | Holzner |
| 7,569,528 B2 | 8/2009 | Lant |
| 7,575,633 B2 | 8/2009 | Romanin |
| 7,575,804 B2 | 8/2009 | Lang-wittkowski |
| 7,585,824 B2 | 9/2009 | Popplewell |
| 7,585,825 B2 | 9/2009 | Artiga |
| 7,585,832 B2 | 9/2009 | Smith |
| 7,736,695 B2 | 6/2010 | Schwantes |
| 7,772,175 B2 | 8/2010 | Panandiker |
| 7,794,836 B2 | 9/2010 | Vasishta |
| 7,799,421 B2 | 9/2010 | Goodson |
| 7,799,752 B2 | 9/2010 | Ness |
| 7,803,422 B2 | 9/2010 | Schwantes |
| 7,833,960 B2 | 11/2010 | Lei |
| 7,871,588 B2 | 1/2011 | Lindner |
| 7,985,445 B2 | 7/2011 | Schwantes |
| 7,998,494 B2 | 8/2011 | Holzner |

(56) References Cited

U.S. PATENT DOCUMENTS

| | | |
|---|---|---|
| 8,022,029 B2 | 9/2011 | Broze |
| 8,026,205 B2 | 9/2011 | Broze |
| 8,053,405 B2 | 11/2011 | Narayanan |
| 8,067,089 B2 | 11/2011 | Schwantes |
| 8,071,214 B2 | 12/2011 | Schwantes |
| 8,093,201 B2 | 1/2012 | Broze |
| 8,110,284 B2 | 2/2012 | Naigertsik |
| 8,119,163 B2 | 2/2012 | Devane |
| 8,129,327 B2 | 3/2012 | Zhang |
| 8,147,808 B2 | 4/2012 | Scavone |
| 8,158,571 B2 | 4/2012 | Alonso |
| 8,163,207 B2 | 4/2012 | Jung |
| 8,192,838 B2 | 6/2012 | Goodson |
| 8,206,820 B2 | 6/2012 | Bogaerts |
| 8,242,069 B2 | 8/2012 | Struillou |
| 8,246,869 B2 | 8/2012 | Stowell |
| 8,252,356 B2 | 8/2012 | Ogura |
| 8,304,075 B2 | 11/2012 | Lang-wittkowski |
| 8,329,154 B2 | 12/2012 | Uchiyama |
| 8,349,300 B2 | 1/2013 | Wells |
| 8,354,369 B2 | 1/2013 | Beaussoubre |
| 8,426,194 B2 | 4/2013 | Cao |
| 8,455,098 B2 | 6/2013 | Schwantes |
| 8,460,791 B2 | 6/2013 | Hentze |
| 8,460,864 B2 | 6/2013 | Cao |
| 8,470,762 B2 | 6/2013 | Broze |
| 8,551,935 B2 | 10/2013 | Smets |
| 9,186,642 B2 | 11/2015 | Dihora |
| 9,221,028 B2 | 12/2015 | Dihora |
| 9,993,793 B2 | 6/2018 | Dihora |
| 2002/0016269 A1 | 2/2002 | Noda |
| 2002/0102286 A1 | 8/2002 | Kantor |
| 2002/0136773 A1 | 9/2002 | Scher |
| 2002/0169233 A1 | 11/2002 | Schwantes |
| 2003/0017126 A1 | 1/2003 | Mahadeshwar |
| 2003/0017959 A1 | 1/2003 | Baeck |
| 2003/0024997 A1 | 2/2003 | Welch |
| 2003/0031722 A1 | 2/2003 | Cao |
| 2003/0073607 A1 | 4/2003 | Smets |
| 2003/0077378 A1 | 4/2003 | Lou |
| 2003/0108501 A1 | 6/2003 | Hofrichter |
| 2003/0109391 A1 | 6/2003 | Midha |
| 2003/0125222 A1 | 7/2003 | Jahns |
| 2003/0139312 A1 | 7/2003 | Caswell |
| 2003/0152542 A1 | 8/2003 | Decoster |
| 2003/0170304 A1 | 9/2003 | Devane |
| 2003/0194416 A1 | 10/2003 | Shefer |
| 2003/0199412 A1 | 10/2003 | Gupta |
| 2003/0203978 A1 | 10/2003 | Obrien |
| 2003/0215417 A1 | 11/2003 | Uchiyama |
| 2003/0216488 A1 | 11/2003 | Uchiyama |
| 2003/0220220 A1 | 11/2003 | Bach |
| 2004/0013737 A1 | 1/2004 | Becourt |
| 2004/0043078 A1 | 3/2004 | Herault |
| 2004/0071742 A1 | 4/2004 | Popplewell |
| 2004/0087470 A1 | 5/2004 | Grandmaire |
| 2004/0091445 A1 | 5/2004 | Dykstra |
| 2004/0101577 A1 | 5/2004 | Ahn |
| 2004/0109920 A1 | 6/2004 | Reuscher |
| 2004/0110898 A1 | 6/2004 | Dreja |
| 2004/0137028 A1 | 7/2004 | Poterie |
| 2004/0138088 A1 | 7/2004 | Pereira |
| 2004/0175347 A1 | 9/2004 | Bissett |
| 2004/0175404 A1 | 9/2004 | Shefer |
| 2004/0197405 A1 | 10/2004 | Devane |
| 2004/0208902 A1 | 10/2004 | Gupta |
| 2004/0214742 A1 | 10/2004 | Meli |
| 2004/0220062 A1 | 11/2004 | Pereira |
| 2004/0229769 A1 | 11/2004 | Smith |
| 2004/0267182 A1 | 12/2004 | Davis et al. |
| 2005/0014674 A1 | 1/2005 | Liechty |
| 2005/0038188 A1 | 2/2005 | Ahn |
| 2005/0043209 A1 | 2/2005 | Schmiedel |
| 2005/0048549 A1 | 3/2005 | Cao |
| 2005/0089540 A1* | 4/2005 | Uchiyama ............. C11D 3/505 424/59 |
| 2005/0112152 A1 | 5/2005 | Popplewell |
| 2005/0113282 A1 | 5/2005 | Parekh |
| 2005/0119351 A1 | 6/2005 | Van Der Schaaf et al. |
| 2005/0129759 A1 | 6/2005 | Sojka |
| 2005/0169793 A1 | 8/2005 | Wheatley |
| 2005/0226900 A1 | 10/2005 | Winton |
| 2005/0227907 A1 | 10/2005 | Lee |
| 2005/0276831 A1 | 12/2005 | Dihora |
| 2006/0008646 A1 | 1/2006 | Haggquist |
| 2006/0099168 A1 | 5/2006 | Corzani |
| 2006/0116304 A1 | 6/2006 | Mcritchie |
| 2006/0127430 A1 | 6/2006 | Gupta |
| 2006/0134154 A1 | 6/2006 | Giles |
| 2006/0160711 A1 | 7/2006 | Frank |
| 2006/0165740 A1 | 7/2006 | Frank |
| 2006/0166855 A1 | 7/2006 | Murad |
| 2006/0217288 A1 | 9/2006 | Wahl |
| 2006/0240105 A1 | 10/2006 | Devane |
| 2006/0248665 A1 | 11/2006 | Pluyter |
| 2006/0258557 A1 | 11/2006 | Popplewell |
| 2006/0263311 A1 | 11/2006 | Scavone |
| 2006/0263312 A1 | 11/2006 | Scavone |
| 2006/0263313 A1 | 11/2006 | Scavone |
| 2006/0263518 A1 | 11/2006 | Schwantes |
| 2006/0263519 A1 | 11/2006 | Schwantes |
| 2006/0263898 A1 | 11/2006 | Paget |
| 2006/0275237 A1 | 12/2006 | Bissett |
| 2006/0292098 A1 | 12/2006 | Scavone |
| 2007/0020205 A1 | 1/2007 | Blin |
| 2007/0031463 A1 | 2/2007 | Fotinos |
| 2007/0041929 A1 | 2/2007 | Torgerson |
| 2007/0048339 A1 | 3/2007 | Popplewell |
| 2007/0071781 A1 | 3/2007 | Louys, Jr. |
| 2007/0071978 A1 | 3/2007 | Sojka |
| 2007/0078071 A1 | 4/2007 | Lee |
| 2007/0122481 A1 | 5/2007 | Liversidge |
| 2007/0123442 A1 | 5/2007 | Holzner |
| 2007/0134411 A1 | 6/2007 | Cont |
| 2007/0138671 A1 | 6/2007 | Anastasiou |
| 2007/0138672 A1 | 6/2007 | Lee |
| 2007/0138673 A1 | 6/2007 | Lee |
| 2007/0138674 A1 | 6/2007 | Anastasiou |
| 2007/0160561 A1 | 7/2007 | Ouali |
| 2007/0160675 A1 | 7/2007 | Devane |
| 2007/0173433 A1 | 7/2007 | Heibel |
| 2007/0202063 A1 | 8/2007 | Dihora |
| 2007/0207109 A1 | 9/2007 | Peffly |
| 2007/0207174 A1 | 9/2007 | Pluyter |
| 2007/0224274 A1 | 9/2007 | Siol |
| 2007/0224395 A1 | 9/2007 | Rowitsch et al. |
| 2007/0248553 A1 | 10/2007 | Scavone |
| 2007/0286837 A1 | 12/2007 | Torgerson |
| 2007/0286904 A1 | 12/2007 | Popplewell |
| 2007/0292361 A1 | 12/2007 | Virgallito |
| 2007/0298061 A1 | 12/2007 | Boghani |
| 2008/0008750 A1 | 1/2008 | Tochio |
| 2008/0032909 A1 | 2/2008 | de Buzzaccarini et al. |
| 2008/0040082 A1 | 2/2008 | Stanton |
| 2008/0057021 A1 | 3/2008 | Dykstra |
| 2008/0102121 A1 | 5/2008 | Devane |
| 2008/0107615 A1 | 5/2008 | Keene |
| 2008/0113025 A1 | 5/2008 | Devane |
| 2008/0118556 A1 | 5/2008 | Devane |
| 2008/0128941 A1 | 6/2008 | Lopez |
| 2008/0182774 A1 | 7/2008 | Naraschkewitz |
| 2008/0187596 A1 | 8/2008 | Dihora |
| 2008/0199503 A1 | 8/2008 | Camargo |
| 2008/0200359 A1 | 8/2008 | Smets |
| 2008/0200363 A1 | 8/2008 | Smets |
| 2008/0213451 A1 | 9/2008 | Ogura |
| 2008/0226684 A1 | 9/2008 | Peppas |
| 2008/0234406 A1 | 9/2008 | Rawlins |
| 2008/0305982 A1 | 12/2008 | Smets |
| 2008/0311064 A1 | 12/2008 | Lei |
| 2008/0317788 A1 | 12/2008 | Louzan |
| 2008/0318788 A1 | 12/2008 | Nadian |
| 2009/0022764 A1 | 1/2009 | Frater |

(56) References Cited

U.S. PATENT DOCUMENTS

| | | |
|---|---|---|
| 2009/0029900 A1 | 1/2009 | Cetti |
| 2009/0035365 A1 | 2/2009 | Popplewell |
| 2009/0047434 A1 | 2/2009 | Trophardy |
| 2009/0053165 A1 | 2/2009 | Brown |
| 2009/0081265 A1 | 3/2009 | Peppas |
| 2009/0118399 A1 | 5/2009 | Benbakoura |
| 2009/0142444 A1 | 6/2009 | Jarrard, Jr. |
| 2009/0149479 A1 | 6/2009 | Jenkins |
| 2009/0202465 A1 | 8/2009 | Mougin |
| 2009/0209661 A1 | 8/2009 | Somerville |
| 2009/0221463 A1 | 9/2009 | Kitko |
| 2009/0232857 A1 | 9/2009 | Peppas |
| 2009/0232858 A1 | 9/2009 | Peppas |
| 2009/0247449 A1 | 10/2009 | Burdis |
| 2009/0252789 A1 | 10/2009 | Trophardy |
| 2009/0258042 A1 | 10/2009 | Anastasiou |
| 2009/0258812 A1 | 10/2009 | Sengupta |
| 2009/0274905 A1 | 11/2009 | Schwantes |
| 2009/0274906 A1* | 11/2009 | Schwantes ............... B01J 13/16 428/402.22 |
| 2009/0274907 A1 | 11/2009 | Schwantes |
| 2009/0275494 A1 | 11/2009 | Ferguson |
| 2009/0289216 A1 | 11/2009 | Jung |
| 2009/0324660 A1 | 12/2009 | Cetti |
| 2010/0003518 A1 | 1/2010 | Grey |
| 2010/0029537 A1 | 2/2010 | Dihora et al. |
| 2010/0040884 A1 | 2/2010 | Smets |
| 2010/0056414 A1 | 3/2010 | Smith |
| 2010/0061954 A1 | 3/2010 | Adams |
| 2010/0068163 A1 | 3/2010 | Lu |
| 2010/0068525 A1 | 3/2010 | Willax |
| 2010/0104611 A1 | 4/2010 | Chan |
| 2010/0104612 A1 | 4/2010 | Cropper |
| 2010/0104613 A1 | 4/2010 | Chan |
| 2010/0119679 A1 | 5/2010 | Dihora |
| 2010/0216684 A1 | 8/2010 | Ferguson |
| 2010/0275384 A1 | 11/2010 | Broze |
| 2010/0286018 A1 | 11/2010 | Hentze |
| 2010/0297446 A1 | 11/2010 | Oxley |
| 2011/0003152 A1 | 1/2011 | Grey |
| 2011/0008427 A1 | 1/2011 | Biggs |
| 2011/0008435 A1 | 1/2011 | Devane |
| 2011/0020416 A1 | 1/2011 | Pluyter |
| 2011/0033513 A1 | 2/2011 | Lei |
| 2011/0086788 A1 | 4/2011 | Smets |
| 2011/0093246 A1 | 4/2011 | Stanton |
| 2011/0111999 A1 | 5/2011 | Smets |
| 2011/0152147 A1 | 6/2011 | Smets |
| 2011/0245141 A1 | 10/2011 | Gizaw |
| 2011/0267702 A1 | 11/2011 | Fujimoto |
| 2011/0268778 A1 | 11/2011 | Dihora |
| 2011/0268802 A1 | 11/2011 | Dihora |
| 2011/0269657 A1 | 11/2011 | Dihora |
| 2011/0269658 A1 | 11/2011 | Dihora |
| 2012/0010120 A1 | 1/2012 | Somerville |
| 2012/0053108 A1 | 3/2012 | Glenn, Jr. |
| 2012/0071391 A1 | 3/2012 | Smets |
| 2012/0076839 A1 | 3/2012 | Chan |
| 2012/0114582 A1 | 5/2012 | Batchelor |
| 2012/0121677 A1 | 5/2012 | Franklin |
| 2012/0177924 A1 | 7/2012 | Jung |
| 2012/0258150 A1 | 10/2012 | Rauckhorst |
| 2012/0276175 A1 | 11/2012 | Dihora |
| 2012/0276210 A1 | 11/2012 | Dihora |
| 2012/0282309 A1 | 11/2012 | Dihora |
| 2012/0322709 A1 | 12/2012 | Li |
| 2013/0137625 A1 | 5/2013 | Stowell |
| 2013/0245153 A1 | 9/2013 | Schwantes |
| 2013/0296211 A1 | 11/2013 | Smets |
| 2014/0037703 A1 | 2/2014 | Dihora |
| 2014/0079747 A1 | 3/2014 | Dihora |
| 2014/0079748 A1 | 3/2014 | Cetti |
| 2014/0086965 A1 | 3/2014 | Dihora |
| 2014/0127309 A1 | 5/2014 | Drake |
| 2014/0178442 A1 | 6/2014 | Li |
| 2014/0227328 A1 | 8/2014 | Dihora |
| 2015/0017214 A1 | 1/2015 | Warr |
| 2015/0071977 A1 | 3/2015 | Dihora et al. |
| 2015/0086595 A1 | 3/2015 | Dihora |
| 2018/0360706 A1 | 12/2018 | Dihora |
| 2019/0142714 A1 | 5/2019 | Dihora |

FOREIGN PATENT DOCUMENTS

| | | |
|---|---|---|
| CN | 1965068 A | 5/2007 |
| CN | 101088567 A | 12/2007 |
| DE | 10062585 A1 | 6/2002 |
| DE | 102005029777 A1 | 1/2007 |
| DE | 102006058253 A1 | 6/2008 |
| DE | 10200803501 A1 | 1/2010 |
| DE | 102008044700 A1 | 2/2010 |
| EP | 0303461 A1 | 2/1989 |
| EP | 0462709 A2 | 12/1991 |
| EP | 0510761 A1 | 10/1992 |
| EP | 0523287 A1 | 1/1993 |
| EP | 0820762 A1 | 1/1998 |
| EP | 0829259 A1 | 3/1998 |
| EP | 1034705 A2 | 9/2000 |
| EP | 1201743 A1 | 5/2002 |
| EP | 1243318 A1 | 9/2002 |
| EP | 1243320 A1 | 9/2002 |
| EP | 1247568 A1 | 10/2002 |
| EP | 1502646 A1 | 2/2005 |
| EP | 1588760 A1 | 10/2005 |
| EP | 1600151 A1 | 11/2005 |
| EP | 1637188 A1 | 3/2006 |
| EP | 1702674 A1 | 9/2006 |
| EP | 1721963 A1 | 11/2006 |
| EP | 1719554 A3 | 8/2007 |
| EP | 1850887 B1 | 7/2008 |
| EP | 2132294 B1 | 9/2012 |
| EP | 2090284 B1 | 12/2012 |
| EP | 2433617 B1 | 5/2019 |
| FR | 2702961 A1 | 9/1994 |
| FR | 2881048 A1 | 7/2006 |
| GB | 1451411 A | 10/1976 |
| GB | 1478788 A | 7/1977 |
| GB | 1546480 A | 5/1979 |
| GB | 2062570 A | 5/1981 |
| GB | 2217603 A | 11/1989 |
| GB | 2274989 B | 3/1997 |
| GB | 2334724 A | 9/1999 |
| JP | S545051 A | 1/1979 |
| JP | S5819261 A | 2/1983 |
| JP | 59139268 A | 8/1984 |
| JP | 61244366 A | 10/1986 |
| JP | 62116506 A | 5/1987 |
| JP | 01256965 A | 10/1989 |
| JP | 02052661 A | 2/1990 |
| JP | H0236803 A | 2/1990 |
| JP | 04021513 A | 1/1992 |
| JP | 04082558 A | 3/1992 |
| JP | 04156851 A | 5/1992 |
| JP | 05017338 A | 1/1993 |
| JP | 06000361 A | 1/1994 |
| JP | H0641576 U | 6/1994 |
| JP | 07075666 A | 3/1995 |
| JP | 07305049 A | 11/1995 |
| JP | H10195478 A | 7/1998 |
| JP | 10231119 A | 9/1998 |
| JP | 2001049287 A | 2/2001 |
| JP | 2002326904 A | 11/2002 |
| JP | 2003099986 A | 4/2003 |
| JP | 2003161893 A | 6/2003 |
| JP | 2004083475 A | 3/2004 |
| JP | 2004099743 A | 4/2004 |
| JP | 2005194308 A | 7/2005 |
| JP | 2007016161 A | 1/2007 |
| JP | 2008156565 A | 7/2008 |
| JP | 2009035454 A | 2/2009 |
| JP | 2009280533 A | 12/2009 |
| JP | 2009290236 A | 12/2009 |
| KR | 20090082704 A | 7/2009 |
| WO | 8403630 A1 | 9/1984 |

(56) References Cited

FOREIGN PATENT DOCUMENTS

| | | |
|---|---|---|
| WO | 9220771 A1 | 11/1992 |
| WO | 9308600 A1 | 4/1993 |
| WO | 9747720 A2 | 12/1997 |
| WO | 9812298 A2 | 3/1998 |
| WO | 9826808 A2 | 6/1998 |
| WO | 9917736 A1 | 4/1999 |
| WO | 9921532 A1 | 5/1999 |
| WO | 9924159 A1 | 5/1999 |
| WO | 0032601 A2 | 6/2000 |
| WO | 0041528 A2 | 7/2000 |
| WO | 0067718 A1 | 11/2000 |
| WO | 200065020 A1 | 11/2000 |
| WO | 0141915 A1 | 6/2001 |
| WO | 0174310 A2 | 10/2001 |
| WO | 02092746 A1 | 11/2002 |
| WO | 03002248 A1 | 1/2003 |
| WO | 03020867 A1 | 3/2003 |
| WO | 2004006967 A1 | 1/2004 |
| WO | 2004060418 A1 | 7/2004 |
| WO | 2004096895 A2 | 11/2004 |
| WO | 2005041908 A1 | 5/2005 |
| WO | 2005047232 A1 | 5/2005 |
| WO | 2005055990 A1 | 6/2005 |
| WO | 2005025626 A3 | 7/2005 |
| WO | 2005123892 A1 | 12/2005 |
| WO | 2006027664 A2 | 3/2006 |
| WO | 2006127454 A2 | 11/2006 |
| WO | 2007040517 A1 | 4/2007 |
| WO | 2007128326 A1 | 11/2007 |
| WO | 2007137441 A1 | 12/2007 |
| WO | 2008005693 A2 | 1/2008 |
| WO | 2008016637 A1 | 2/2008 |
| WO | 2008058868 A1 | 5/2008 |
| WO | 2008129028 A1 | 10/2008 |
| WO | 2008145874 A1 | 12/2008 |
| WO | 2008152543 A1 | 12/2008 |
| WO | 2008154765 A1 | 12/2008 |
| WO | 2008104352 A3 | 1/2009 |
| WO | 2009047127 A1 | 4/2009 |
| WO | 2009047745 A2 | 4/2009 |
| WO | 2009080695 A1 | 7/2009 |
| WO | 2009083941 A2 | 7/2009 |
| WO | 2009095823 A1 | 8/2009 |
| WO | 2009106318 A2 | 9/2009 |
| WO | 2009093812 A3 | 10/2009 |
| WO | 2009134234 A1 | 11/2009 |
| WO | 2010079466 A2 | 7/2010 |
| WO | 2010079458 A3 | 1/2011 |
| WO | 2012166884 A3 | 5/2013 |

OTHER PUBLICATIONS

PCT Search Report and Written Opinion for PCT/IB2010/052127 dated Jul. 11, 2011, 16 pages.
All Office Actions; U.S. Appl. No. 12/777,301, filed May 11, 2020.
All Office Actions; U.S. Appl. No. 12/777,304, filed May 11, 2020.
All Office Actions; U.S. Appl. No. 12/777,314, filed May 11, 2010.
All Office Actions; U.S. Appl. No. 12/777,318, filed May 11, 2010.
All Office Actions; U.S. Appl. No. 14/032,835, filed Sep. 20, 2013.
All Office Actions; U.S. Appl. No. 14/032,859, filed Sep. 20, 2013.
All Office Actions; U.S. Appl. No. 14/032,868, filed Sep. 20, 2013.
All Office Actions; U.S. Appl. No. 14/032,888, filed Sep. 20, 2013.
All Office Actions; U.S. Appl. No. 14/045,661, filed Oct. 3, 2013.
All Office Actions; U.S. Appl. No. 14/045,670, filed Oct. 3, 2013.
All Office Actions; U.S. Appl. No. 14/543,432, filed Nov. 17, 2014.
All Office Actions; U.S. Appl. No. 14/543,885, filed Nov. 17, 2014.
All Office Actions; U.S. Appl. No. 15/992,506, filed May 30, 2018.
All Office Actions; U.S. Appl. No. 16/246,568, filed Jan. 14, 2019.
Brunauer, et al., "Absorption of Gases in Multimolecular Layers", Journal of the American Chemical Society, vol. 60, 1938, pp. 309-319.
Fernandes et al., "Influence of Spray Drying Operating Conditions on Microencapsulated Rosemary Essential Oil Properties", Ciência e Tecnologia de Alimentos, vol. 33, Suppl. 1, 2013, pp. 171-178.
Fowkes, F.M., "Attractive Forces at Interfaces", Industrial and Engineering Chemistry, vol. 56, No. 12, 1964, pp. 40-52.
Good, et al, A Theory for Estimation of Surface and Interfacial Energies, III, Estimation of Surface Energies or Solids from Contact Angle Data, The Journal of Physical Chemistry, vol. 64, May 1960, pp. 561-565.
Herbig, James A., "Microencapsulation", Kirk Othmer Encyclopedia of Chemical Technology, vol. 13, Second Edition, pp. 436-456.
Huber et al, "Capsular Adhesives", Tappi, vol. 49, No. 5, May 1966, pp. 41A-44A.
Leo et al, "Methods of Calculating Partition Coefficients", Comprehensive Medicinal Chemistry, vol. 4, 1990, pp. 295-319.
Takenaka et al., "Preparation of enteric-coated microcapsules for tableting by spray-drying technique and In Vitro simulation of drug release from the tablet in GI tract", Journal of Pharmaceutical Sciences, vol. 69, Issue 12, Dec. 1980, pp. 1388-1392.
Third Party Opposition filed for European Patent Application Ser. No. 10721568.3, dated Apr. 17, 2020; 16 pages.
Uppalapati et el., "Effect of External Lubricant on Mechanical Properties of Dry-Pressed Green Bodies", Journal of the American Ceramic Society, 2005, vol. 88, No. 6, pp. 1397-1402.
Washburn, Edward W., "The Dynamics of Capillary Flow", Physical Review Journals, vol. 17, No. 3, 1921, pp. 374-375.
Xie et al., "The Effects of Rheological Properties of Wall Materials on Morphology and Particle Size Distribution of Microcapsulein Czech", Journal of Food Science, 2010, vol. 28, No. 5, pp. 433-439.
Zhang, Z. et al, "Mechanical Properties of Melamine-FormaldehydeMicrocapsules", Journal of Microencapsulation, vol. 18, No. 5, 2001, pp. 593-602.
Zim's Crack Creme (R),2003, Perfects Products, Inc., Berlin Center, Ohio 44401, pp. 1-3.

* cited by examiner

DELIVERY PARTICLE

FIELD OF INVENTION

The present application relates to encapsulated benefit agents, compositions comprising such encapsulated benefit agents and processes for making and using compositions comprising such encapsulated benefit agents.

BACKGROUND OF THE INVENTION

Benefit agents, such as perfumes, silicones, waxes, flavors, vitamins and softening agents, are expensive and generally less effective when employed at high levels in personal care compositions, cleaning compositions, and fabric care compositions. As a result, there is a desire to maximize the effectiveness of such benefit agents. One method of achieving this objective is to improve the retention of such benefit agents whilst formulated and aged in a formulated product composition and delivery efficiencies of such benefit agents. Unfortunately, it is difficult to improve the retention and delivery efficiencies of benefit agents as such agents may be lost due to the agents' physical or chemical characteristics, or such agents may be incompatible with other compositional components or the situs that is treated.

In an effort to improve the delivery efficiencies of benefit agents, the industry, in many cases, encapsulated such benefit agents. In one aspect, U.S. Pat. Nos. 4,001,140; 4,081,376; and 4,089,802 disclose a method for capsule formation utilizing a reaction between urea and formaldehyde. In one aspect, U.S. Pat. No. 4,100,103 discloses a reaction between melamine and formaldehyde. Forming microcapsules from urea-formaldehyde resin and/or melamine formaldehyde resin via polycondensation reaction are disclosed in U.S. Pat. Nos. 4,001,140; 4,081,376; 4,089,802; 4,100,103; 4,015,823; and 4,444,699. Alternatively, one can utilize interfacial polymerization with polycondensation to manufacture poly(urea) and/or poly(urethane) capsules. Such microcapsule walls are the reaction products of a reaction of a polyisocyanate with a polyamine and/or a polyol, and are disclosed in U.S. Pat. No. 6,248,364; EP 0537167 B1; and USPA 2002/0136773 A1. Alternatively, one can utilize complex coacervation methods to develop a wall around a dispersed benefit agent. Such microcapsule walls are the reaction products of anionic polymers and cationic polymers and/or surfactants, optionally followed by a crosslinking reaction. The use of cationic polymers such as gelatin with anionic polymers, such as polyphosphates or polysaccharides, are disclosed in U.S. Pat. No. 4,622,267. Alternatively, one can surround a benefit agent core with an inorganic shell. Such capsules are disclosed in WO 2009/106318A2.

Alternatively, one can employ acrylates and esters of acrylic acid to surround a benefit agent core, such capsules are disclosed in U.S. Pat. No. 6,951,836 B2, and USPA 2009/0289216 A1. One approach described in the art is to manufacture a porous bead comprising acrylate materials, which can then be subsequently loaded with benefit agents, such approaches are disclosed in U.S. Pat. No. 5,145,675; WO2000041528, U.S. Pat. No. 5,856,409; USPA 2005/0121143 A1, USPA 2005/0129759 A1, and U.S. Pat. No. 5,725,869. Another approach disclosed in the art is for the use of acrylates as enteric coatings, e.g. to trigger the release of benefit agents from a delivery system upon a change in pH, such approaches are described in WO 2005055990, USPA 2010/0003518 A1, WO 2008058868, U.S. Pat. No. 6,375,983, USPA 2002/0102286 A1. Another approach is to utilize interfacial polymerization, wherein acrylate monomers are dispersed in a hydrophobic benefit agent, followed by polymerization of the dispersed monomers which then migrate to an oil/water interface to form a shell that surround the benefit agent. Such approaches are disclosed in U.S. Pat. No. 5,292,835; USPA 2003/0125222 A1, and USPA 2005/0043078 A1. Such microcapsules are deficient in their ability to manage both leakage of the benefit agent, and controlling the release of the benefit agent during or after application to a situs.

Unfortunately, capsules manufactured using the aforementioned methods and raw materials have several drawbacks which include: (1) they cannot be formulated in certain classes of products due to strict formulation limits, (2) they have high permeabilities when incorporated into products that contain high levels of surfactant, solvents, and/or water, which results in the premature benefit agent release, (3) they can only effectively encapsulate a limited breadth of benefit agents, and (4) they either are so stable that they do not release the benefit agent in use or have insufficient mechanical stability to withstand the processes required to incorporate them in and/or make a consumer product and (5) they do not adequately deposit on the situs that is being treated with consumer product that contains capsules.

Accordingly, there is a need for encapsulated benefit agents, compositions, that eliminate or minimize one or more of the aforementioned drawbacks.

SUMMARY OF THE INVENTION

The present application relates to encapsulated benefit agents, compositions comprising such encapsulated benefit agents and processes for making and using compositions comprising such encapsulated benefit agents. Such encapsulated benefit agents eliminate or minimize one or more of the drawbacks of current encapsulated benefit agents and thus provide formulators with additional perfume delivery opportunities.

DETAILED DESCRIPTION OF THE INVENTION

Definitions

As used herein "consumer product" means baby care, personal care, fabric & home care, family care, feminine care, health care, snack and/or beverage products or devices intended to be used or consumed in the form in which it is sold, and not intended for subsequent commercial manufacture or modification. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners; hair shampoos and hair-rinses; shower gels and foam baths and metal cleaners; as well as cleaning auxiliaries such as foam substrates, films, and combinations thereof, bleach additives and "stain-stick" or pre-treat types, substrate-laden products such as dryer added sheets, dry and wetted wipes and pads, nonwoven substrates, and sponges; as well as sprays and mists.

As used herein, the term "fabric care composition" includes, unless otherwise indicated, fabric softening compositions, fabric enhancing compositions, fabric freshening compositions and combinations there of.

As used herein, the term "personal care composition" includes, unless otherwise indicated, any personal care composition that can be applied to the keratinaceous surfaces of the body including the skin and/or hair. The personal care compositions can be, for example, formulated as bars, liquids, emulsions, shampoos, gels, powders, sticks, hair conditioners (rinse off and leave in), hair tonics, pastes, hair colorants, sprays, mousses and/or other styling products, as well as shave prep products, and devices used for shaving.

As used herein, the term "fluid" includes liquid, gel, paste and gas product forms.

As used herein, the term "solid" means granular, powder, bar and tablet product forms.

As used herein, the term "situs" includes paper products, fabrics, garments, hard surfaces, hair and skin.

As used herein, the terms "particle", "benefit agent delivery particle", "capsule" and "microcapsule" are synonymous and microcapsules encompass perfume microcapsules.

As used herein, the articles including "a" and "an" when used in a claim, are understood to mean one or more of what is claimed or described.

As used herein, the terms "include", "includes" and "including" are meant to be non-limiting.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Particles

Current encapsulated benefit agents are made by processes including coacervation, polycondensation, interfacial polymerization, emulsion polymerization, solvent evaporation, solvent exchange, lyophilization, nanoprecipitation, spray drying, extrusion, fluid bed coating, and combinations thereof. As noted, such encapsulated benefit agents have certain drawbacks.

Applicants encapsulated benefit agents are made by an interfacial polymerization process. While not being bound by theory, Applicants believe that the proper selection of materials and the aforementioned process results in the surprising improved properties of Applicants' encapsulated benefit agents. Such improved properties include, the required safety profile coupled with the correct range of permeability and friability as well as the ability to encapsulate a wide range of benefit agents. In short, particles made according to the invention can be employed without restriction in consumer products, exhibit surprisingly lower benefit agent leakage and yet adequately release their benefit agent in use.

In one aspect, particles, each of said particles independently having a particle size of from about 2 microns to about 80 microns, from about 5 microns to about 50 microns or even from about 10 microns to about 30 microns, each particle comprising:

a.) a core that comprises, based on total particle weight, from about 6% to about 99.9%, from about 11% to about 95%, or from about 50% to about 75%, of a benefit agent and from about 0.1% to about 94%, from about 5% to about 89%, or even from about 25% to about 50% of a partitioning modifier and/or density modifier; and b.) a shell that encapsulates said core, said shell comprising, based on total shell weight, from about 50% to about 100%, from about 70% to about 100% or even from about 80% to about 100% of a polyacrylate, is disclosed.

In one aspect, of said particles, said particles may comprise, a material selected from the group consisting of perfumes; brighteners; insect repellants; silicones; waxes; flavors; vitamins; fabric softening agents; skin care agents; enzymes; probiotics; dye polymer conjugate; dye clay conjugate; perfume delivery system; sensates in one aspect a cooling agent; attractants, in one aspect a pheromone; antibacterial agents; dyes; pigments; bleaches; and mixtures thereof.

In one aspect, of said particles, said benefit agent may comprise:

a.) a perfume oil; and b.) a partitioning modifier selected from the group consisting of oil soluble materials that have a C log P greater than from about 4, or from about 5, or from about 7, or even from about 11 and/or materials that also have a density higher than 1 gram per cubic centimeter. In one aspect, suitable partitioning modifier may comprise a material selected from the group consisting of materials include Mono, di- and tri-esters of $C_4$-$C_{24}$ fatty acids and glycerine; fatty acid esters of polyglycerol oligomers; polyalphaolefins; silicone oil; crosslinked silicones comprising polyether substituted structural units and acrylate crosslinks; polyglycerol ether silicone crosspolymers; alkyl substituted cellulose; hydroxypropyl cellulose; fatty esters of acrylic or methacrylic acid that have side chain crystallizing groups; copolymers of ethylene, including ethylene and vinyl acetate, ethylene and vinyl alcohol, ethylene/acrylic elastomers; acetyl caryophyllene, hexarose, butyl oleate, hydrogenated castor oil, sucrose benzoate, dodecanoic acid, palmitic acid, stearic acid, tetradecanol, hexadecanol, 1-octanediol, isopropyl myristate, castor oil, mineral oil, isoparaffin, capryllic triglyceride, soybean oil, vegetable oil, brominated vegetable oil, bromoheptane, sucrose octaacetate, geranyl palmitate, acetylcaryophyllene, sucrose benzoate, butyl oleate, silicones, polydimethylsiloxane, vitamin E, decamethylcyclopentasiloxane, dodecamethylcyclohxasiloxane, sucrose soyate, sucrose stearate, sucrose soyanate, lauryl alcohol, 1-tetradecanol, 1-hexadecanol, cetyl alcohol, 1-octadecanol, 1-docosanol, 2-octyl-1-dodecanol, perfume oils, in one aspect perfume oils having a C log P>5, in one aspect said perfume oils may be selected from the group consisting of: Octadecanoic acid, octadecyl ester; Tetracosane, 2,6,10,15,19, 23-hexamethyl-; Octadecanoic acid, diester dissolved in 1,2,3-propanetriol; Isotridecane, 1,1'-[(3,7-dimethyl-6-octenylidene)bis(oxy)]bis-; Tetradecanoic acid, octadecyl ester; 2,6,10,14,18,22-Tetracosahexaene, 2,6,10, 15,19,23-hexamethyl-, (all-E)-; Tricosane; Docosane; Hexadecanoic acid, dodecyl ester; 1,2-Benzenedicarboxylic acid, didodecyl ester; Decanoic acid, 1,2,3-propanetriyl ester; 1-Undecene, 11,11-bis[(3,7-dimethyl-6-octenyl)oxy]-; Heneicosane; Benzene, [2-[bis[(3,7-dimethyl-2,6-octadienyl)oxy]methyl]-1-;
1-Undecene, 11,11-bis[(3,7-dimethyl-2,6-octadienyl) oxy]-; Benzene, [2-[bis[(1-ethenyl-1,5-dimethyl-4-hexenyl)oxy]methyl]-1-; Dodecanoic acid, tetradecyl ester; 2H-1-Benzopyran-6-ol, 3,4-dihydro-2,5,7,8-tetramethyl-2-(4,8,12-trimethyltridecyl)-, [2R-[2R*(4R*,8R*)]]—; Octanoic acid, octadecyl ester; Eicosane; 2H-1-Benzopyran-6-ol, 3,4-dihydro-2,5,8-trimethyl-2-(4,8,12-trimethyltridecyl)-, [2R*(4R*, 8R*)]—; 2-Naphthalenol, 1-[6-(2,2-dimethyl-6-methylenecyclohexyl)-4-methyl-3-hexenyl]decahydro-2,5, 5,8a-tetramethyl-, [1R-[1.alpha.[E(S*)],2.beta., 4a.beta.,8a.alpha.]]-; 2H-1-Benzopyran-6-ol, 3,4-dihydro-2,7,8-trimethyl-2-(4,8,12-trimethyltridecyl)-, [2R-[2R*(4R*, 8R*)]—; Heptanoic acid, octadecyl ester; Nonadecane; 2,4,6,8,10,12,14,16-Heptadecaoctaenal, 2,6,11,15-tetramethyl-17-(2,6,6-trimethyl-1-cyclohexen-1-yl)-, (2E,4E,6E,8E,10E,12E,14E,16E)-; 2H-1-Benzopyran-6-ol, 3,4-dihydro-2,8-dimethyl-2-(4,8,12-trimethyltridecyl)-, [2R-[2R*(4R*, 8R*)]]—; Hexadecanoic acid, 2-ethylhexyl ester; 1,2-Benzenedicarboxylic acid, didecyl ester; Octadecane; Benzoic acid, 24 [2-(phenylmethylene)octylidene]amino]-,1-ethenyl-1,5-di methyl-4-hexenyl ester; Octadecanoic acid, 3-methylbutyl ester; Decanoic acid, ester with 1,2,3-propanetriol octanoate; Heptadecane; 1-Hexadecene, 7,11,15-trimethyl-3-methylene-; Dodecanoic acid, decyl ester; Octadecanoic acid, butyl ester; Decanedioic acid, bis(2-ethylhexyl) ester; Benzene, [2,2-bis[(3,7-dimethyl-6-octenyl)oxy]ethyl]-; Benzene, [2,2-bis[(3,7-dimethyl-2,6-octadienyl)oxy]ethyl]-; 9-Octadecenoic acid (Z)—, butyl ester; Octanoic acid, 1,2,3-propanetriyl ester; Hexadecane; Cyclohexene, 4-(5-methyl-1-methylene-4-hexenyl)-1-(4-methyl-3-pentenyl)-; 2-Hexadecen-1-ol, 3,7,11,15-tetramethyl-, acetate, [R—[R*,R*-(E)]]-; Hexadecanoic acid, butyl ester; Octadecanoic acid, ethyl ester; 1-Dodecanol, 2-octyl-; Pentadecane; Tetradecanoic acid, hexyl ester; Decanoic acid, decyl ester; Acetic acid, octadecyl ester; Hexadecanoic acid, 2-methylpropyl ester; 9-Octadecenoic acid (Z)—, ethyl ester; Heptadecanoic acid, ethyl ester; Octadecanoic acid, methyl ester; Tetradecane; Tetradecanoic acid, 3-methylbutyl ester; 2-Hexadecen-1-ol, 3,7,11,15-tetramethyl-, [R—[R*,R*-(E)]]-; 2-Hexadecen-1-ol, 3,7,11,15-tetramethyl-; Hexadecanoic acid, 1-methylethyl ester; 1H-Indole, 1,1'-(3,7-dimethyl-6-octenylidene)bis-; Octadecanoic acid; Cyclopentasiloxane, decamethyl-; Benzoic acid, 2-[[2-(phenylmethylene)octylidene]amino]-,3-methylbutyl ester; 9,12-Octadecadienoic acid (Z,Z)—, ethyl ester; 1-Octadecanol; Hexanedioic acid, dioctyl ester; 9-Octadecenoic acid (Z)—, methyl ester; Octadecanoic acid, 2-hydroxypropyl ester; Tetradecanoic acid, butyl ester; Dodecanoic acid, hexyl ester; 9,12,15-Octadecatrienoic acid, ethyl ester, (Z,Z,Z)—; Hexadecanoic acid, ethyl ester; 1-Hexadecanol, acetate; 9-Octadecenoic acid (Z)—; Hexanedioic acid, bis(2-ethylhexyl) ester; 1,8,11,14-Heptadecatetraene; 1,8,11,14-Heptadecatetraene; 1,8,11,14-Heptadecatetraene; 9-Octadecen-1-ol, (Z)—; Tetradecanoic acid, 2-methylpropyl ester; Nonanoic acid, 1-methyl-1,2-ethanediyl ester; Tridecane; Naphthalene, decahydro-1,6-dimethyl-4-(1-methylethyl)-, [1S-(1.alpha.,4.alpha.,4a.alpha.,6.alpha.,8a.beta.)]-, didehydro deriv.; 1-Hexadecyn-3-ol, 3,7,11,15-tetramethyl-; 9,12-Octadecadienoic acid (Z,Z)—, methyl ester; 1-Heptadecanol; 6,10,14-Hexadecatrien-3-ol, 3,7,11,15-tetramethyl-; Benzoic acid, 2-[[[4-(4-methyl-3-pentenyl)-3-cyclohexen-1-yl]methylene]amino]-, methyl ester; 9,12-Octadecadienoic acid (Z,Z)—; 2-Nonene, 1,1'-oxybis-; Santalol, benzeneacetate; 10-Undecenoic acid, heptyl ester; 9,12,15-Octadecatrienoic acid, methyl ester, (Z,Z,Z)—; Octadecanoic acid, monoester with 1,2,3-propanetriol; Dodecanoic acid, pentyl ester; Octanoic acid, nonyl ester; Pentadecanoic acid, ethyl ester; Hexadecanoic acid, methyl ester; Dodecanoic acid, 4-methylphenyl ester; Dodecanoic acid, 3-methylbutyl ester; Tetradecanoic acid, 1-methylethyl ester; Hexadecanoic acid; 1-Phenanthrenecarboxylic acid, tetradecahydro-1,4a-dimethyl-7-(1-methylethyl)-, methyl ester, [1R-(1.alpha.,4a.beta.,4b.alpha.,7.beta.,8a.beta.,10a.alpha.)]-; 1-Hexadecanol; Dodecane; 2-Pentadecanone, 6,10,14-trimethyl-; 9-Heptadecanone; 1-Phenanthrenemethanol, 1,2,3,4,4 a,4b,5,6,10,10 a-decahydro-1,4a-dimethyl-7-(1-methylethyl)-, acetate, [1R-(1.alpha.,4a.beta.,4b.alpha.,10a.alpha.)]-; Isohexadecanol; Dodecanoic acid, 2-methylpropyl ester; Hexadecanenitrile; Octadecanoic acid, 2,3-dihydroxypropyl ester; Isododecane; 1-Phenanthrenemethanol, tetradecahydro-1,4a-dimethyl-7-(1-methylethyl)-; Octanoic acid, 3,7-dimethyl-2,6-octadienyl ester, (E)-; Dodecanoic acid, butyl ester; Tetradecanoic acid, ethyl ester; Butanoic acid, dodecyl ester; Benzoic acid, 2-amino-, decyl ester; Oxacycloheptadecan-2-one; Propanoic acid, 2-methyl-, dodecyl ester; 1H-Indene, octahydro-1,1,2,3,3-pentamethyl-; 1-Phenanthrenecarboxylic acid, 1,2,3,4,4a,4b,5,6,7,8,10,10a-dodecahydro-1,4a-dimethyl-7-(1-methylethyl)-, methyl ester; 9-Octadecenoic acid (Z)—, ester with 1,2,3-propanetriol; 9,12,15-Octadecatrienoic acid, (Z,Z,Z)—; 1,4,8-Cycloundecatriene, 2,6,6,9-tetramethyl-, (E,E,E)-; 1-Phenanthrenemethanol, dodecahydro-1,4a-dimethyl-7-(1-methylethyl)-; Benzoic acid, 3,4,5-trihydroxy-, dodecyl ester; 1H-Indole-1-heptanol, .eta.-1H-indol-1-yl-.alpha.,.alpha.,.epsilon.-; Cyclododecane; 9-Hexadecenoic acid, (Z)—; Benzoic acid, 2-[[2-(phenylmethylene)heptylidene]amino]-, methyl; 9-Octadecenoic acid (Z)—, 2,3-dihydroxypropyl ester; 2-Naphthalenecarboxaldehyde, 5,6,7,8-tetrahydro-3,5,5,6,7,8,8-heptamethyl-, trans-; Octanoic acid, 1-ethenyl-1,5-dimethyl-4-hexenyl ester; 2-Hexadecanone and mixtures thereof; and/or a density modifier selected from the group consisting of Brominated vegetable oil; sucrose octaacetate; bromoheptane; titanium dioxide; zinc oxides; iron oxides; cobalt oxides; nickel oxides; silver oxides; copper oxides; zirconium oxides; silica; silver; zinc; iron; cobalt; nickel; copper; epoxidized soybean oil polyols; 1h-indene, 2,3-dihydro-1,1,3,3,5-pentamethyl-4,6-dinitro-; benzene, (2-bromoethenyl)-; benzeneacetic acid, 2-methoxy-4-(1-propenyl)phenyl ester; ethanone, 1-(2,5-dimethyl-3-thienyl)-; oxiranecarboxylic acid, 3-(4-methoxyphenyl)-, ethyl ester; benzoic acid, 2-[(1-hydroxy-3-phenylbutyl)amino]-, methyl ester; 1,3-benzodioxole-5-carboxylic acid, ethyl ester; 1,3-benzodioxole, 5-(2-propenyl)-; benzoic acid, 4-methoxy-; benzenemethanol, .alpha.-(trichloromethyl)-, acetate; phenol, 2-methoxy-4-(2-propenyl)-, formate; phenol, 2-methoxy-4-(2-propenyl)-, benzoate; 2-propen-1-ol, 3-phenyl-, benzoate; benzeneacetic acid, 3-methylphenyl ester; benzene, 1-(1,1-dimethylethyl)-3,4,5-trimethyl-2,6-dinitro-; benzeneacetic acid, 4-methylphenyl ester; benzeneacetic acid, phenylmethyl ester; benzeneacetic acid, (4-methoxyphenyl) methyl ester; 2-propenoic acid, 3-phenyl-, phenylmethyl ester; 2-propenoic acid, 3-phenyl-, 2-phenylethyl ester; benzeneacetic acid, 2-methoxy-4-(2-propenyl) phenyl ester; phenol, 2-(methylthio)-; benzoic acid, 2-[[3-(1,3-benzodioxol-5-yl)-2-methylpropylidene] amino]-, methyl ester; benzoic acid, 2-[[3-(4-methoxyphenyl)-2-methylpropylidene]amino]-,methyl ester; benzoic acid, 3,5-dimethoxy-; benzoic acid, 2-hydroxy-, phenyl ester; benzoic acid, 2-hydroxy-, phenylmethyl ester; benzoic acid, 2-hydroxy-, ethyl ester; benzoic acid, 2-hydroxy-, methyl ester; benzoic acid, 2-amino-, methyl ester; ethanone, 2-hydroxy-1,2-diphenyl-; benzoic acid, 4-hydroxy-, ethyl ester; benzoic acid, phenylmethyl ester; 1,3-benzodioxole, 5-(1-propenyl)-; benzothiazole, 2-methyl-; 5h-dibenzo[a,d]cyclohepten-5-one, 10,11-dihydro-; oxiranecarboxylic acid, 3-phenyl-, ethyl ester; benzoic acid, 4-methoxy-, methyl ester; 2-propenoic acid, 3-phenyl-, 3-phenyl-2-propenyl ester; tricyclo[3.3.1.13,7]decan-2-ol, 4-methyl-8-methylene-; tricyclo[3.3.1.13,7]decan-2-ol, 4-methyl-8-methylene-, acetate; methanone, bis(2,4-dihydroxyphenyl)-; methanone, (2-hydroxy-4-methoxyphenyl)phenyl-; dibenzofuran; benzoic acid, 2-amino-, (naphthalenyl)-; furan, 2,2'-[thiobis(methylene)]bis-; 1,2,3-propanetriol, tripropanoate; 2-propenoic acid, 3-phenyl-, (e)-; phenol, 4-ethyl-2,6-dimethoxy-; disulfide, methyl phenyl; benzoic acid, 2-[[(4-methoxyphenyl)methylene]amino]-, methyl ester; 2-propenoic acid, 3-(2-methoxyphenyl)-, (z)-; 8-quinolinol; disulfide, bis(phenylmethyl); 1,2-propanediol, dibenzoate; benzene, 1-bromo-4-ethenyl-; trisulfide, di-2-propenyl; phenol, 2,6-dimethoxy-4-(1-propenyl)-, (e)-; benzene, (2-isothiocyanatoethyl)-; benzoic acid, 2-hydroxy-5-methyl-, methyl ester; 1,2,4-trithiolane, 3,5-dimethyl-; propanoic acid, 2-(methyldithio)-, ethyl ester; benzoic acid, 2-hydroxy-, cyclohexyl ester; benzoic acid, 2-[(1-oxopropyl)amino]-, methyl ester; ethanethioic acid, s-(4,5-dihydro-2-methyl-3-furanyl) ester; benzoic acid, 2-(acetylamino)-, methyl ester; 1,3,5-trithiane, 2,4,6-trimethyl-; benzoic acid, 2-amino-, propyl ester; butanoic acid, 1-naphthalenyl ester; benzoic acid, 2,4-dihydroxy-3-methyl-, methyl ester; trisulfide, methyl 2-propenyl; 2-furanmethanol, benzoate; benzoic acid, 2-hydroxy-5-methyl-, ethyl ester; benzene, (2,2-dichloro-1-methylcyclopropyl)-; 2-thiophenecarboxaldehyde, 5-ethyl-; benzoic acid, [(phenylmethylene)amino]-, methyl ester; spiro[1,3-dithiolo[4,5-b]furan-2,3'(2'h)-furan], hexahydro-2',3a-dimethyl-; 1,3-benzodioxole, 5-(diethoxymethyl)-; cyclododeca[c]furan, 1,3,3a,4,5,6,7,8,9,10,11,13a-dodecahydro-; benzeneacetic acid, 2-methoxyphenyl ester; 2-benzofurancarboxaldehyde; 1,2,4-trithiane, 3-methyl-; furan, 2,2'-[dithiobis(methylene)]bis-; 1,6-heptadiene-3,5-dione, 1,7-bis(4-hydroxy-3-methoxyphenyl)-, (e,e)-; benzoic acid, 2,4-dihydroxy-3,6-dimethyl-, methyl ester; benzoic acid, 2-hydroxy-4-methoxy-, methyl ester; propanoic acid, 2-methyl-, 1,3-benzodioxol-5-ylmethyl ester; 1,2,4-trithiolane, 3,5-diethyl-; 1,2,4-trithiolane, 3,5-bis(1-methylethyl)-; furan, 2-[(methyldithio)methyl]-; tetrasulfide, dimethyl; benzeneacetaldehyde, .alpha.-(2-furanylmethylene)-; benzoic acid, 3-methoxy-; benzenecarbothioic acid, s-methyl ester; benzoic acid, 2-methoxy-, methyl ester; benzoic acid, 2-hydroxy-, 4-methylphenyl ester; benzoic acid, 2-hydroxy-, propyl ester; 2-propenoic acid, 3-(2-methoxyphenyl)-; 2-propenoic acid, 3-(3-methoxyphenyl)-; benzoic acid, 2-hydroxy-4-methoxy-6-methyl-, ethyl ester; benzaldehyde, 2-hydroxy-5-methyl-; 1,2,3-propanetriol, tribenzoate; benzoic acid, 4-methylphenyl ester; 2-furancarboxylic acid, propyl ester; benzoic acid, 2-hydroxy-, 2-methylphenyl ester; benzoic acid, 4-hydroxy-3-methoxy-, ethyl ester; 2-propenoic acid, 3-phenyl-; benzene, 1,3-dibromo-2-methoxy-4-methyl-5-nitro-; benzene, (isothiocyanatomethyl)-; 2-propenoic acid, 3-(2-furanyl)-, ethyl ester; benzenemethanethiol, 4-methoxy-; 2-thiophenemethanethiol; benzene, 1,1'-[(2-phenylethylidene)bis(oxymethylene)]bis-; phenol, 2,6-dimethoxy-4-(2-propenyl)-; benzoic acid, 2-[(2-phenylethylidene)amino]-, methyl ester; benzenepropanoic acid, .beta.-oxo-, 4-methylphenyl ester; 1h-indole-3-heptanol, .eta.-1h-indol-3-yl-.alpha.,.alpha.,.epsilon.-trimethyl-; benzoic acid, 2-hydroxy-, 3-methyl-2-butenyl ester; 1,3-benzodioxole-5-propanol, .alpha.-methyl-, acetate; thiophene, 2,2'-dithiobis-; benzoic acid, 2-hydroxy-; benzaldehyde, 2-hydroxy-4-methyl-; disulfide, methyl phenylmethyl; 2-furancarboxylic acid, 2-phenylethyl ester; benzenethiol, 2-methoxy-; benzoic acid, 2-[[(4-hydroxy-3-methoxyphenyl)methylene]amino]-,methyl ester; ethanol, 2-(4-methylphenoxy)-1-(2-phenylethoxy)-; benzeneacetic acid, 3-phenyl-2-propenyl ester; benzoic acid, 2-amino-, 2-propenyl ester; bicyclo[3.2.1]octan-8-one, 1,5-dimethyl-, oxime; 2-thiophenethiol; phenol, 2-methoxy-4-(1-propenyl)-, formate; benzoic acid, 2-amino-, cyclohexyl ester; phenol, 4-ethenyl-2-methoxy-; benzoic acid, 2-hydroxy-, 2-(1-methylethoxy)ethyl ester; ethanone, 1-[4-(1,1-dimethylethyl)-2,6-dimethyl-3,5-dinitrophenyl]-; benzene, 1-(1,1-dimethylethyl)-3,5-dimethyl-2,4,6-trinitro-; 2-propenoic acid, 3-(4-methoxyphenyl)-; benzene, 1-(1,1-dimethylethyl)-2-methoxy-4-methyl-3,5-dinitro-; 1,2-benzenedicarboxylic acid, diethyl ester; ethanone, 1-(3,4-dihydro-2h-pyrrol-5-yl)-; benzoic acid, 2-(methylamino)-, methyl ester; 2h-1-benzopyran-2-one, 7-ethoxy-4-methyl-; benzoic acid, 2-hydroxy-, 2-phenylethyl ester; benzoic acid, 2-amino-, ethyl ester; 2-propen-1-ol, 3-phenyl-, 2-aminobenzoate; phenol, 4-chloro-3,5-dimethyl-; disulfide, diphenyl; 1-naphthalenol; [1,1'-biphenyl]-2-ol; benzenemethanol, .alpha.-phenyl-; 2-naphthalenethiol; ethanone, 1-(2-naphthalenyl)-; phenol, 2-methoxy-4-(1-propenyl)-, acetate; 2-naphthalenol, benzoate; benzoic acid, phenyl ester; pyridine, 2-[3-(2-chlorophenyl)propyl]-; benzoic acid, 4-hydroxy-, propyl ester; ethanone, 1-(1-naphthalenyl)-; propanoic acid, 3-[(2-furanylmethyl)thio]-, ethyl ester; 2-propen-1-one, 1,3-diphenyl-; 3-pyridinecarboxylic acid, phenylmethyl ester; benzoic acid, 2-phenylethyl ester; piperidine, 1-[5-(1,3-benzodioxol-5-yl)-1-oxo-2,4-pentadienyl]-,(e,e)-; benzothiazole and mixtures thereof.

In one aspect of said particles, said perfume may comprise from about 2% to about 80%, from about 20% to about 70%, from about 30% to about 60% of a perfume raw material with a C log P less than 3.5, less than 3 or even from about 0.5 to about 3.

In one aspect of said particles, said perfume may comprise from about 2% to about 80%, from about 20% to about 70%, from about 30% to about 60% of a perfume raw material with an Odor Detection Threshold (ODT) less than 50 parts per billion, less than 25 parts per billon, or even from about 0.1 parts per billion to about 25 parts per billion.

In one aspect of said particles, said polyacrylate may comprise a polyacrylate random copolymer, said polyacrylate random copolymer comprising, based on total polyacrylate weight:
  a.) from about 0.2% to about 2.0%, amine content;
  b.) from about 0.6% to about 6.0% carboxylic acid; or
  c.) from about 0.1% to about 1.0% amine content and from about 0.3% to about 3.0% carboxylic acid.

In one aspect of said particles said particles may have a cationic charge at a pH range from about 2 to about 10, from about 3 to about 9 or even from about 4 to about 8.

In one aspect of said particles, at least 75% of said particles may have a fracture strength of from about 0.2 MPa to about 30 MPa; from about 0.6 MPa to about 10 MPa, from about 1.0 MPa to about 5 MPa, or even from about 1.2 MPa to about 3 MPa.

In one aspect, Applicants' particles may be made by any of the processes disclosed in the present specification.

Process of Making Particles

In one aspect, a process of making particles, each of said particles independently having a particle size of from about 2 microns to about 80 microns, from about 5 microns to about 50 microns or even from about 10 microns to about 30 microns, each particle comprising:
  a.) a core that comprises, based on total particle weight, from about 6% to about 99.9%, from about 11% to about 95%, or from about 50% to about 75%, of a benefit agent and from about 0.1% to about 94%, from about 5% to about 89%, or even from about 25% to about 50% of a partitioning modifier and/or density modifier; and
  b.) a shell that encapsulates said core, said shell comprising, based on total shell weight, from about 50% to about 100%, from about 70% to about 100% or even from about 80% to about 100% of a polyacrylate
is disclosed.

In one aspect, a process of making a particle comprising:
  a.) reacting a multifunctional acrylate monomer and/or multifunctional acrylate oligomer, in one aspect a multifunctional methacrylate monomer and/or multifunctional methacrylate oligomer, in a benefit agent comprising a partitioning modifier and/or density modifier with a composition comprising:
    i) an amine acrylate and/or methacrylate and a strong acid; or
    ii) a carboxylic acid acrylate and/or methacrylate monomer and a strong base; or
    iii) an amine acrylate and/or methacrylate monomer and a carboxylic acid acrylate and/or carboxylic acid methacrylate monomer
  to form a core composition,
  b.) forming an emulsion comprising said core composition, a surfactant, in one aspect anionic, cationic or neutral surfactant, and water;
  c.) curing said emulsion by applying a sufficient amount of thermal, UV, and/or electron beam energy to said emulsion to induce sufficient free-radical polymerization to form a particle having a core comprising said benefit agent and a shell comprising an acrylate, said shell encapsulating said benefit agent is disclosed.

The properties of the oil play an important role in determining how much, how quickly, and how permeable the polyacrylate shell material will be when established at the oil/water interface. If the oil phase comprises highly polar materials, these materials will reduce the diffusion of the acrylate oligomers and polymers to the oil/water interface and result in a very thin, highly permeable shell. Incorporation of partitioning modifier which can adjust the polarity of the core, thereby changing the partition coefficient of the polar materials in the partitioning modifier versus the acrylate oligomers, can result in the establishment of a well defined, highly impermeable shell. In one aspect, of the invention, the partitioning modifier and/or density modifier are combined with the core oil material prior to incorporation of the wall forming monomers.

The emulsifier comprises a water-soluble or water-dispersible material and optionally a water phase initiator, where the first composition initiator and the water phase initiator is an energy-activated initiator. The reaction product of the first composition and second composition results in the formation of a population of microcapsules having a microcapsule wall of low leakage of the core material.

In one aspect of the invention, encapsulated benefit agent particles have reduced leakage when incorporated in a surfactant containing cleaning composition. In one aspect of the invention, the Headspace Ratio is from about 0.05 to 0.90, from about 0.20 to about 0.80, or even from about 0.2 to about 0.40. The Headspace Ratio compares the quantity of volatile material in the headspace of a consumer product formulation when the volatile material is in an encapsulated form vs. a non-encapsulated form. The Headspace Ratio is a relative measure of the leakage stability of the encapsulated benefit agent.

In one aspect of the invention, encapsulated benefit agents are manufactured and are subsequently coated with a material to reduce the rate of leakage of the benefit agent from the particles when the particles are subjected to a bulk environment containing, for example, surfactants, polymers, and solvents. Non-limiting examples of coating materials that can serve as barrier materials include materials selected from the group consisting of polyvinyl pyrrolidone homopolymer, and its various copolymers with styrene, vinyl acetate, imidazole, primary and secondary amine containing monomers, methyl acrylate, polyvinyl acetal, maleic anhydride; polyvinyl alcohol homopolymer, and its various copolymers with vinyl acetate, 2-acrylamide-2-methylpropane sulfonate, primary and secondary amine containing monomers, imidazoles, methyl acrylate; polyacrylamides; polyacrylic acids; microcrystalline waxes; styrene-butadiene latex; paraffin waxes; modified polysaccharides such as waxy maize or dent corn starch, octenyl succinated starches, derivatized starches such as hydroxyethylated or hydroxypropylated starches, high amylose starches, gel forming retrogradable starches, pre-gelatinized starches, carrageenan, guar gum, sodium alginate, pectin, xanthan gum; modified celluloses such as hydrolyzed cellulose acetate, hydroxy propyl cellulose, carboxymethyl hydroxyethyl cellulose, hydroxyethyl cellulose, methyl cellulose, microcrystalline cellulose, acid-hydrolyzed microcrystalline cellulose to yield cellulose nanocrystals, and the like; modified proteins such as gelatin, casein; hydrogenated and non-hydrogenated polyalkenes; fatty acids; polyacrylic acid; hardened shells such as, gelatin-polyphosphate, polyvinyl alcohol crosslinked with sodium tetraborate or gluteraldehyde; latexes of styrene-butadiene, ethyl cellulose, silica and modified silica; inorganic materials such as clays including magnesium silicates, aluminosilicates; sodium silicates, and the like; and mixtures thereof. Such materials can be obtained from CP Kelco Corp. of San Diego, California, USA; Degussa AG or Dusseldorf, Germany; BASF AG of Ludwigshafen, Germany; Rhodia Corp. of Cranbury, New Jersey, USA; Baker Hughes Corp. of Houston, Texas, USA; Hercules Corp. of Wilmington, Delaware, USA; Agrium Inc. of Calgary, Alberta, Canada, ISP of New Jersey U.S.A, Purdue University, Indiana, USA.

Suitable equipment for use in the processes disclosed herein may include continuous stirred tank reactors, homogenizers, turbine agitators, recirculating pumps, paddle mixers, ploughshear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Kentucky, U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minnesota, USA), Arde Barinco (New Jersey, USA).

Slurry/Agglomerate

In one aspect, a slurry that may comprise any of the particles disclosed in the present specification is disclosed. Said slurry may be combined with an adjunct ingredient to form a composition, for example, a consumer product.

In one aspect of said slurry one or more processing aids are selected from the group consisting of water, aggregate inhibiting materials such as divalent salts, particle suspending polymers, and mixtures thereof. Examples of aggregate inhibiting materials include salts that can have a charge-shielding effect around the particle, such as magnesium chloride, calcium chloride, magnesium bromide, magnesium sulfate, and mixtures thereof. Examples of particle suspending polymers include polymers such as xanthan gum, carrageenan gum, guar gum, shellac, alginates, chitosan; cellulosic materials such as carboxymethyl cellulose, hydroxypropyl methyl cellulose, cationically charged cellulosic materials; polyacrylic acid; polyvinyl alcohol; hydrogenated castor oil; ethylene glycol distearate; and mixtures thereof.

In one aspect, said slurry may comprise one or more processing aids, selected from the group consisting of water, aggregate inhibiting materials such as divalent salts; particle suspending polymers such as xanthan gum, guar gum, caboxy methyl cellulose.

In one aspect of the aforementioned slurry said one or more carriers may be selected from the group consisting of polar solvents, including but not limited to, water, ethylene glycol, propylene glycol, polyethylene glycol, glycerol; non-polar solvents, including but not limited to, mineral oil, perfume raw materials, silicone oils, hydrocarbon paraffin oils, and mixtures thereof.

In one aspect of said slurry, said slurry may comprise a deposition aid that may comprise a polymer selected from the group comprising: polysaccharides, in one aspect, cationically modified starch and/or cationically modified guar; polysiloxanes; poly diallyl dimethyl ammonium halides; copolymers of poly diallyl dimethyl ammonium chloride and polyvinyl pyrrolidone; a composition comprising polyethylene glycol and polyvinyl pyrrolidone; acrylamides; imidazoles; imidazolinium halides; polyvinyl amine; copolymers of poly vinyl amine and N-vinyl formamide; polyvinylformamide, polyvinyl alcohol; polyvinyl alcohol crosslinked with boric acid; polyacrylic acid; polyglycerol ether silicone crosspolymers; polyacrylic acids, polyacrylates, copolymers of polyvinylamine and polvyinylalcohol oligimers of amines, in one aspect a diethylenetriamine, ethylene diamine, bis(3-aminopropyl)piperazine, N,N-Bis-(3-aminopropyl)methylamine, tris(2-aminoethyl)amine and mixtures thereof; polyethyleneimime, a derivatized polyethyleneimine, in one aspect an ethoxylated polyethyleneimine; a polymeric compound comprising, at least two moieties selected from the moieties consisting of a carboxylic acid moiety, an amine moiety, a hydroxyl moiety, and a nitrile moiety on a backbone of polybutadiene, polyisoprene, polybutadiene/styrene, polybutadiene/acrylonitrile, carboxyl-terminated polybutadiene/acrylonitrile or combinations thereof; pre-formed coacervates of anionic surfactants combined with cationic polymers; polyamines and mixtures thereof.

In one aspect, an agglomerate that comprises said particles and a second material is disclosed.

In one aspect of said agglomerate, said second material may comprise a material selected from the group consisting of silicas, citric acid, sodium carbonate, sodium sulfate, sodium chloride, and binders such as sodium silicates, modified celluloses, polyethylene glycols, polyacrylates, polyacrylic acids, zeolites and mixtures thereof Compositions Comprising Particles Particles made according to the invention can be employed without restriction in consumer products, exhibit surprisingly lower benefit agent leakage and yet adequately release their benefit agent in use.

In one aspect, a composition comprising an adjunct ingredient and, based on total composition weight, and from about 0.1% to about 50%, from about 0.2% to about 25%, from about 0.5% to about 10%, or even from about 0.75% to about 5% particles, each of said particles independently having a particle size of from about 2 microns to about 80 microns, from about 5 microns to about 50 microns or even from about 10 microns to about 30 microns, each particle comprising:

a.) a core that comprises, based on total particle weight, from about 6% to about 99.9%, from about 11% to about 95%, or from about 50% to about 75%, of a benefit agent and from about 0.1% to about 94%, from about 5% to about 89%, or even from about 25% to about 50% of a partitioning modifier and/or density modifier; and b.) a shell that encapsulates said core, said shell comprising, based on total shell weight, from about 50% to about 100%, from about 70% to about 100% or even from about 80% to about 100% of a polyacrylate, said composition being a consumer product, is disclosed.

In one aspect, of said composition said benefit agent may comprise, a material selected from the group consisting of perfumes; brighteners; insect repellants; silicones; waxes; flavors; vitamins; fabric softening agents; skin care agents; enzymes; probiotics; dye polymer conjugate; dye clay conjugate; perfume delivery system; sensates in one aspect a cooling agent; attractants, in one aspect a pheromone; antibacterial agents; dyes; pigments; bleaches; and mixtures thereof.

In one aspect, of said composition said benefit agent may comprise:

a.) a perfume oil; and b.) a partitioning modifier selected from the group consisting of oil soluble materials that have a C log P greater than from about 4, or from about 5, or from about 7, or even from about 11 and/or materials that also have a density higher than 1 gram per cubic centimeter. In one aspect, suitable partitioning modifier may comprise a material selected from the group consisting of materials include Mono, di- and tri-esters of $C_4$-$C_{24}$ fatty acids and glycerine; fatty acid esters of polyglycerol oligomers; polyalphaolefins; silicone oil; crosslinked silicones comprising polyether substituted structural units and acrylate crosslinks; polyglycertol ether silicone crosspolymers; alkyl substituted cellulose; hydroxypropyl cellulose; fatty esters of acrylic or methacrylic acid that have side chain crystallizing groups; copolymers of ethylene, including ethylene and vinyl acetate, ethylene and vinyl alcohol, ethylene/acrylic elastomers; acetyl caryophyllene, hexarose, butyl oleate, hydrogenated castor oil, sucrose benzoate, dodecanoic acid, palmitic acid, stearic acid, tetradecanol, hexadecanol, 1-octanediol, isopropyl myristate, castor oil, mineral oil, isoparaffin, capryllic triglyceride, soybean oil, vegetable oil, brominated vegetable oil, bromoheptane, sucrose octaacetate, geranyl palmitate, acetylcaryophyllene, sucrose benzoate, butyl oleate, silicones, polydimethylsiloxane, vitamin E, decamethylcyclopentasiloxane, dodecamethylcyclohxasiloxane, sucrose soyate, sucrose stearate, sucrose soyanate, lauryl alcohol, 1-tetradecanol, 1-hexadecanol, cetyl alcohol, 1-octadecanol, 1-docosanol, 2-octyl-1-dodecanol, perfume oils, in one aspect perfume oils having a C log P>5, in one aspect said perfume oils may be selected from the group consisting of: Octadecanoic acid, octadecyl ester; Tetracosane, 2,6,10,15,19, 23-hexamethyl-; Octadecanoic acid, diester dissolved in 1,2,3-propanetriol; Isotridecane, 1,1'-[(3,7-dimethyl-6-octenylidene)bis(oxy)]bis-; Tetradecanoic acid, octadecyl ester; 2,6,10,14,18,22-Tetracosahexaene, 2,6,10, 15,19,23-hexamethyl-, (all-E)-; Tricosane; Docosane; Hexadecanoic acid, dodecyl ester; 1,2-Benzenedicarboxylic acid, didodecyl ester; Decanoic acid, 1,2,3-propanetriyl ester; 1-Undecene, 11,11-bis[(3,7-dimethyl-6-octenyl)oxy]-; Heneicosane; Benzene, [2-[bis [(3,7-dimethyl-2,6-octadienyl)oxy]methyl]-1-; 1-Undecene, 11,11-bis[(3,7-dimethyl-2,6-octadienyl) oxy]-; Benzene, [2-[bis[(1-ethenyl-1,5-dimethyl-4-hexenyl)oxy]methyl]-1-; Dodecanoic acid, tetradecyl ester; 2H-1-Benzopyran-6-ol, 3,4-dihydro-2,5,7,8-tetramethyl-2-(4,8,12-trimethyltridecyl)-, [2R-[2R* (4R*,8R*)]]—; Octanoic acid, octadecyl ester; Eicosane; 2H-1-Benzopyran-6-ol, 3,4-dihydro-2,5,8-trimethyl-2-(4,8,12-trimethyltridecyl)-, [2R*(4R*, 8R*)]]—; 2-Naphthalenol, 1-[6-(2,2-dimethyl-6-methylenecyclohexyl)-4-methyl-3-hexenyl]decahydro-2,5, 5,8a-tetramethyl-, [1R-[1.alpha.[E(S*)],2.beta., 4a.beta.,8a.alpha.]]-; 2H-1-Benzopyran-6-ol, 3,4-dihydro-2,7,8-trimethyl-2-(4,8,12-trimethyltridecyl)-, [2R-[2R*(4R*,8R*)]]—; Heptanoic acid, octadecyl ester; Nonadecane; 2,4,6,8,10,12,14,16-Heptadecaoctaenal, 2,6,11,15-tetramethyl-17-(2,6,6-trimethyl-1-cyclohexen-1-yl)-, (2E,4E,6E,8E,10E,12E,14E,16E)-; 2H-1-Benzopyran-6-ol, 3,4-dihydro-2,8-dimethyl-2-(4,8,12-trimethyltridecyl)-, [2R-[2R*(4R*, 8R*)]]—; Hexadecanoic acid, 2-ethylhexyl ester; 1,2-Benzenedicarboxylic acid, didecyl ester; Octadecane; Benzoic acid, 2-[[2-(phenylmethylene)octylidene]amino]-,1-ethenyl-1,5-di methyl-4-hexenyl ester; Octadecanoic acid, 3-methylbutyl ester; Decanoic acid, ester with 1,2,3-propanetriol octanoate; Heptadecane; 1-Hexadecene, 7,11,15-trimethyl-3-methylene-; Dodecanoic acid, decyl ester; Octadecanoic acid, butyl ester; Decanedioic acid, bis(2-ethylhexyl) ester; Benzene, [2,2-bis[(3,7-dimethyl-6-octenyl)oxy]ethyl]-; Benzene, [2,2-bis[(3,7-dimethyl-2,6-octadienyl)oxy]ethyl]-; 9-Octadecenoic acid (Z)—, butyl ester; Octanoic acid, 1,2,3-propanetriyl ester; Hexadecane; Cyclohexene, 4-(5-methyl-1-methylene-4-hexenyl)-1-(4-methyl-3-pentenyl)-; 2-Hexadecen-1-ol, 3,7,11,15-tetramethyl-, acetate, [R—[R*,R*-(E)]]-; Hexadecanoic acid, butyl ester; Octadecanoic acid, ethyl ester; 1-Dodecanol, 2-octyl-; Pentadecane; Tetradecanoic acid, hexyl ester; Decanoic acid, decyl ester; Acetic acid, octadecyl ester; Hexadecanoic acid, 2-methylpropyl ester; 9-Octadecenoic acid (Z)—, ethyl ester; Heptadecanoic acid, ethyl ester; Octadecanoic acid, methyl ester; Tetradecane; Tetradecanoic acid, 3-methylbutyl ester; 2-Hexadecen-1-ol, 3,7,11,15-tetramethyl-, [R—[R*,R*-(E)]]-; 2-Hexadecen-1-ol, 3,7,11,15-tetramethyl-; Hexadecanoic acid, 1-methylethyl ester; 1H-Indole, 1,1'-(3,7-dimethyl-6-octenylidene)bis-; Octadecanoic acid; Cyclopentasiloxane, decamethyl-; Benzoic acid, 2-[[2-(phenylmethylene)octylidene]amino]-,3-methylbutyl ester; 9,12-Octadecadienoic acid (Z,Z)—, ethyl ester; 1-Octadecanol; Hexanedioic acid, dioctyl ester; 9-Octadecenoic acid (Z)—, methyl ester; Octadecanoic acid, 2-hydroxypropyl ester; Tetradecanoic acid, butyl ester; Dodecanoic acid, hexyl ester; 9,12,15-Octadecatrienoic acid, ethyl ester, (Z,Z,Z)—; Hexadecanoic acid, ethyl ester; 1-Hexadecanol, acetate; 9-Octadecenoic acid (Z)—; Hexanedioic acid, bis(2-ethylhexyl) ester; 1,8, 11,14-Heptadecatetraene; 1,8,11,14-Heptadecatetraene; 1,8,11,14-Heptadecatetraene; 9-Octadecen-1-ol, (Z)—; Tetradecanoic acid, 2-methylpropyl ester; Nonanoic acid, 1-methyl-1,2-ethanediyl ester; Tridecane; Naphthalene, decahydro-1,6-dimethyl-4-(1-methylethyl)-, [1S-(1.alpha.,4.alpha.,4a.alpha.,6.alpha.,8a.beta.)]-, didehydro deriv.; 1-Hexadecyn-3-ol, 3,7,11,15-tetramethyl-; 9,12-Octadecadienoic acid (Z,Z)—, methyl ester; 1-Heptadecanol; 6,10,14-Hexadecatrien-3-ol, 3,7,11,15-tetramethyl-; Benzoic acid, 2-[[[4-(4-methyl-3-pentenyl)-3-cyclohexen-1-yl]methylene]amino]-, methyl ester; 9,12-Octadecadienoic acid (Z,Z)—; 2-Nonene, 1,1'-oxybis-; Santalol, benzeneacetate; 10-Undecenoic acid, heptyl ester; 9,12,15-Octadecatrienoic acid, methyl ester, (Z,Z,Z)—; Octadecanoic acid, monoester with 1,2,3-propanetriol; Dodecanoic acid, pentyl ester; Octanoic acid, nonyl ester; Pentadecanoic acid, ethyl ester; Hexadecanoic acid, methyl ester; Dodecanoic acid, 4-methylphenyl ester; Dodecanoic acid, 3-methylbutyl ester; Tetradecanoic acid, 1-methylethyl ester; Hexadecanoic acid; 1-Phenanthrenecarboxylic acid, tetradecahydro-1,4a-dimethyl-7-(1-methylethyl)-, methyl ester, [1R-(1.alpha.,4a.beta.,4b.alpha.,7.beta.,8a.beta.,10a.alpha.)]-; 1-Hexadecanol; Dodecane; 2-Pentadecanone, 6,10,14-trimethyl-; 9-Heptadecanone; 1-Phenanthrenemethanol, 1,2,3,4,4 a,4b,5,6,10,10a-decahydro-1,4a-dimethyl-7-(1-methylethyl)-, acetate, [1R-(1.alpha.,4a.beta.,4b.alpha.,10a.alpha.)]-; Isohexadecanol; Dodecanoic acid, 2-methylpropyl ester; Hexadecanenitrile; Octadecanoic acid, 2,3-dihydroxypropyl ester; Isododecane; 1-Phenanthrenemethanol, tetradecahydro-1,4a-dimethyl-7-(1-methylethyl)-; Octanoic acid, 3,7-dimethyl-2,6-octadienyl ester, (E)-; Dodecanoic acid, butyl ester; Tetradecanoic acid, ethyl ester; Butanoic acid, dodecyl ester; Benzoic acid, 2-amino-, decyl ester; Oxacycloheptadecan-2-one; Propanoic acid, 2-methyl-, dodecyl ester; 1H-Indene, octahydro-1,1,2,3,3-pentamethyl-; 1-Phenanthrenecarboxylic acid, 1,2,3,4,4a,4b,5,6,7,8,10,10a-dodecahydro-1,4a-dimethyl-7-(1-methylethyl)-, methyl ester; 9-Octadecenoic acid (Z)—, ester with 1,2,3-propanetriol; 9,12,15-Octadecatrienoic acid, (Z,Z,Z)—; 1,4,8-Cycloundecatriene, 2,6,6,9-tetramethyl-, (E,E,E)-; 1-Phenanthrenemethanol, dodecahydro-1,4a-dimethyl-7-(1-methylethyl)-; Benzoic acid, 3,4,5-trihydroxy-, dodecyl ester; 1H-Indole-1-heptanol, .eta.-1H-indol-1-yl-.alpha.,.alpha.,.epsilon.-; Cyclododecane; 9-Hexadecenoic acid, (Z)—; Benzoic acid, 2-[[2-(phenylmethylene)heptylidene]amino]-, methyl; 9-Octadecenoic acid (Z)—, 2,3-dihydroxypropyl ester; 2-Naphthalenecarboxaldehyde, 5,6,7,8-tetrahydro-3,5,5,6,7,8,8-heptamethyl-, trans-; Octanoic acid, 1-ethenyl-1,5-dimethyl-4-hexenyl ester; 2-Hexadecanone and mixtures thereof; and/or a density modifier selected from the group consisting of Brominated vegetable oil; sucrose octaacetate; bromoheptane; titanium dioxide; zinc oxides; iron oxides; cobalt oxides; nickel oxides; silver oxides; copper oxides; zirconium oxides; silica; silver; zinc; iron; cobalt; nickel; copper; epoxidized soybean oil polyols; 1h-indene, 2,3-dihydro-1,1,3,3,5-pentamethyl-4,6-dinitro-; benzene, (2-bromoethenyl)-; benzeneacetic acid, 2-methoxy-4-(1-propenyl)phenyl ester; ethanone, 1-(2,5-dimethyl-3-thienyl)-; oxiranecarboxylic acid, 3-(4-methoxyphenyl)-, ethyl ester; benzoic acid, 2-[(1-hydroxy-3-phenylbutyl)amino]-, methyl ester; 1,3-benzodioxole-5-carboxylic acid, ethyl ester; 1,3-benzodioxole, 5-(2-propenyl)-; benzoic acid, 4-methoxy-; benzenemethanol, .alpha.-(trichloromethyl)-, acetate; phenol, 2-methoxy-4-(2-propenyl)-, formate; phenol, 2-methoxy-4-(2-propenyl)-, benzoate; 2-propen-1-ol, 3-phenyl-, benzoate; benzeneacetic acid, 3-methylphenyl ester; benzene, 1-(1,1-dimethylethyl)-3,4,5-trimethyl-2,6-dinitro-; benzeneacetic acid, 4-methylphenyl ester; benzeneacetic acid, phenylmethyl ester; benzeneacetic acid, (4-methoxyphenyl) methyl ester; 2-propenoic acid, 3-phenyl-, phenylmethyl ester; 2-propenoic acid, 3-phenyl-, 2-phenylethyl ester; benzeneacetic acid, 2-methoxy-4-(2-propenyl) phenyl ester; phenol, 2-(methylthio)-; benzoic acid, 2-[[3-(1,3-benzodioxol-5-yl)-2-methylpropylidene] amino]-, methyl ester; benzoic acid, 2-[[3-(4-methoxyphenyl)-2-methylpropylidene]amino]-,methyl ester; benzoic acid, 3,5-dimethoxy-; benzoic acid, 2-hydroxy-, phenyl ester; benzoic acid, 2-hydroxy-, phenylmethyl ester; benzoic acid, 2-hydroxy-, ethyl ester; benzoic acid, 2-hydroxy-, methyl ester; benzoic acid, 2-amino-, methyl ester; ethanone, 2-hydroxy-1,2-diphenyl-; benzoic acid, 4-hydroxy-, ethyl ester; benzoic acid, phenylmethyl ester; 1,3-benzodioxole, 5-(1-propenyl)-; benzothiazole, 2-methyl-; 5h-dibenzo[a,d]cyclohepten-5-one, 10,11-dihydro-; oxiranecarboxylic acid, 3-phenyl-, ethyl ester; benzoic acid, 4-methoxy-, methyl ester; 2-propenoic acid, 3-phenyl-, 3-phenyl-2-propenyl ester; tricyclo[3.3.1.13,7]decan-2-ol, 4-methyl-8-methylene-; tricyclo[3.3.1.13,7]decan-2-ol, 4-methyl-8-methylene-, acetate; methanone, bis(2,4-dihydroxyphenyl)-; methanone, (2-hydroxy-4-methoxyphenyl)phenyl-; dibenzofuran; benzoic acid, 2-amino-, 2-phenylethyl ester; ethanone, 1-(naphthalenyl)-; furan, 2,2'-[thiobis(methylene)]bis-; 1,2,3-propanetriol, tripropanoate; 2-propenoic acid, 3-phenyl-, (e)-; phenol, 4-ethyl-2,6-dimethoxy-; disulfide, methyl phenyl; benzoic acid, 2-[[(4-methoxyphenyl)methylene]amino]-, methyl ester; 2-propenoic acid, 3-(2-methoxyphenyl)-, (z)-; 8-quinolinol; disulfide, bis(phenylmethyl); 1,2-propanediol, dibenzoate; benzene, 1-bromo-4-ethenyl-; trisulfide, di-2-propenyl; phenol, 2,6-dimethoxy-4-(1-propenyl)-, (e)-; benzene, (2-isothiocyanatoethyl)-; benzoic acid, 2-hydroxy-5-methyl-, methyl ester; 1,2,4-trithiolane, 3,5-dimethyl-; propanoic acid, 2-(methyldithio)-, ethyl ester; benzoic acid, 2-hydroxy-, cyclohexyl ester; benzoic acid, 2-[(1-oxopropyl)amino]-, methyl ester; ethanethioic acid, s-(4,5-dihydro-2-methyl-3-furanyl) ester; benzoic acid, 2-(acetylamino)-, methyl ester; 1,3,5-trithiane, 2,4,6-trimethyl-; benzoic acid, 2-amino-, propyl ester; butanoic acid, 1-naphthalenyl ester; benzoic acid, 2,4-dihydroxy-3-methyl-, methyl ester; trisulfide, methyl 2-propenyl; 2-furanmethanol, benzoate; benzoic acid, 2-hydroxy-5-methyl-, ethyl ester; benzene, (2,2-dichloro-1-methylcyclopropyl)-; 2-thiophenecarboxaldehyde, 5-ethyl-; benzoic acid, [(phenylmethylene)aminol-, methyl ester; spiro[1,3-dithiolo[4,5-b]furan-2,3' (2'h)-furan], hexahydro-2',3a-dimethyl-; 1,3-benzodioxole, 5-(di ethoxy methyl)-; cyclododeca[c] furan, 1,3,3a,4,5,6,7,8,9,10,11,13a-dodecahydro-; benzeneacetic acid, 2-methoxyphenyl ester; 2-benzofurancarboxaldehyde; 1,2,4-trithiane, 3-methyl-; furan, 2,2'-[dithiobis(methylene)]bis-; 1,6-heptadiene-3,5-dione, 1,7-bis(4-hydroxy-3-methoxyphenyl)-, (e,e)-; benzoic acid, 2,4-dihydroxy-3,6-dimethyl-, methyl ester; benzoic acid, 2-hydroxy-4-methoxy-, methyl ester; propanoic acid, 2-methyl-, 1,3-benzodioxol-5-ylmethyl ester; 1,2,4-trithiolane, 3,5-diethyl-; 1,2,4-trithiolane, 3,5-bis(1-methylethyl)-; furan, 2-[(methyldithio)methyl]-; tetrasulfide, dimethyl; benzeneacetaldehyde, .alpha.-(2-furanylmethylene)-; benzoic acid, 3-methoxy-; benzenecarbothioic acid, s-methyl ester; benzoic acid, 2-methoxy-, methyl ester; benzoic acid, 2-hydroxy-, 4-methylphenyl ester; benzoic acid, 2-hydroxy-, propyl ester; 2-propenoic acid, 3-(2-methoxyphenyl)-; 2-propenoic acid, 3-(3-methoxyphenyl)-; benzoic acid, 2-hydroxy-4-methoxy- 6-methyl-, ethyl ester; benzaldehyde, 2-hydroxy-5-methyl-; 1,2,3-propanetriol, tribenzoate; benzoic acid, 4-methylphenyl ester; 2-furancarboxylic acid, propyl ester; benzoic acid, 2-hydroxy-, 2-methylphenyl ester; benzoic acid, 4-hydroxy-3-methoxy-, ethyl ester; 2-propenoic acid, 3-phenyl-; benzene, 1,3-dibromo-2-methoxy-4-methyl-5-nitro-; benzene, (isothiocyanatomethyl)-; 2-propenoic acid, 3-(2-furanyl)-, ethyl ester; benzenemethanethiol, 4-methoxy-; 2-thiophenemethanethiol; benzene, 1,1'-[(2-phenylethylidene)bis(oxymethylene)]bis-; phenol, 2,6-dimethoxy-4-(2-propenyl)-; benzoic acid, 2-[(2-phenylethylidene)amino]-, methyl ester; benzenepropanoic acid, .beta.-oxo-, 4-methylphenyl ester; 1h-indole-3-heptanol, .eta.-1h-indol-3-yl-.alpha.,.alpha.,.epsilon.-trimethyl-; benzoic acid, 2-hydroxy-, 3-methyl-2-butenyl ester; 1,3-benzodioxole-5-propanol, .alpha.-methyl-, acetate; thiophene, 2,2'-dithiobis-; benzoic acid, 2-hydroxy-; benzaldehyde, 2-hydroxy-4-methyl-; disulfide, methyl phenylmethyl; 2-furancarboxylic acid, 2-phenylethyl ester; benzenethiol, 2-methoxy-; benzoic acid, [(4-hydroxy-3-methoxyphenyl)methylene]amino]-,methyl ester; ethanol, 2-(4-methylphenoxy)-1-(2-phenylethoxy)-; benzeneacetic acid, 3-phenyl-2-propenyl ester; benzoic acid, 2-amino-, 2-propenyl ester; bicyclo[3.2.1]octan-8-one, 1,5-dimethyl-, oxime; 2-thiophenethiol; phenol, 2-methoxy-4-(1-propenyl)-, formate; benzoic acid, 2-amino-, cyclohexyl ester; phenol, 4-ethenyl-2-methoxy-; benzoic acid, 2-hydroxy-, 2-(1-methylethoxy)ethyl ester; ethanone, 1-[4-(1,1-dimethylethyl)-2,6-dimethyl-3,5-dinitrophenyl]-; benzene, 1-(1,1-dimethyl ethyl)-3,5-dimethyl-2,4,6-trinitro-; 2-propenoic acid, 3-(4-methoxyphenyl)-; benzene, 1-(1,1-dimethylethyl)-2-methoxy-4-methyl-3,5-dinitro-; 1,2-benzenedicarboxylic acid, diethyl ester; ethanone, 1-(3,4-dihydro-2h-pyrrol-5-yl)-; benzoic acid, 2-(methylamino)-, methyl ester; 2h-1-benzopyran-2-one, 7-ethoxy-4-methyl-; benzoic acid, 2-hydroxy-, 2-phenylethyl ester; benzoic acid, 2-amino-, ethyl ester; 2-propen-1-ol, 3-phenyl-, 2-aminobenzoate; phenol, 4-chloro-3,5-dimethyl-; disulfide, diphenyl; 1-naphthalenol; [1,1'-biphenyl]-2-ol; benzenemethanol, .alpha.-phenyl-; 2-naphthalenethiol; ethanone, 1-(2-naphthalenyl)-; phenol, 2-methoxy-4-(1-propenyl)-, acetate; 2-naphthalenol, benzoate; benzoic acid, phenyl ester; pyridine, 2-[3-(2-chlorophenyl)propyl]-; benzoic acid, 4-hydroxy-, propyl ester; ethanone, 1-(1-naphthalenyl)-; propanoic acid, 3-[(2-furanylmethyl)thio]-, ethyl ester; 2-propen-1-one, 1,3-diphenyl-; 3-pyridinecarboxylic acid, phenylmethyl ester; benzoic acid, 2-phenylethyl ester; piperidine, 1-[5-(1,3-benzodioxol-5-yl)-1-oxo-2,4-pentadienyl]-,(e,e)-; benzothiazole and mixtures thereof.

In one aspect of said composition, said perfume may comprise from about 2% to about 80%, from about 20% to about 70%, from about 30% to about 60% of a perfume raw material with a C log P less than 3.5, less than 3 or even from about 0.5 to about 3.

In one aspect of said composition, said perfume may comprise from about 2% to about 80%, from about 20% to about 70%, from about 30% to about 60% of a perfume raw material with an Odor Detection Threshold (ODT) less than 50 parts per billion, less than 25 parts per billon, or even from about 0.1 parts per billion to about 25 parts per billion.

In one aspect of said composition, said the Headspace Ratio of said composition may be from about 0.05 to 0.90, from about 0.20 to about 0.80, or even from about 0.2 to about 0.40.

In one aspect of said composition, said polyacrylate may comprise a polyacrylate random copolymer, said polyacrylate random copolymer comprising, based on total polyacrylate weight:
  a.) from about 0.2% to about 2.0%, amine content;
  b.) from about 0.6% to about 6.0% carboxylic acid; or
  c.) from about 0.1% to about 1.0% amine content and from about 0.3% to about 3.0% carboxylic acid.

In one aspect of said composition said adjunct may be selected from the group consisting of polymers, in one aspect, a cationic polymer, surfactants, builders, chelating agents, dye transfer inhibiting agents, dispersants, enzymes, enzyme stabilizers, catalytic materials, bleach activators, polymeric dispersing agents, clay soil removal/anti-redeposition agents, brighteners, dye polymer conjugates; dye clay conjugates, suds suppressors, dyes, bleach catalysts, additional perfume and/or perfume delivery systems, structure elasticizing agents, fabric softeners, carriers, hydrotropes, processing aids, rheology modifiers, structurants, thickeners, pigments, water and mixtures thereof.

In one aspect of said composition said composition may comprise a material selected from the group consisting of dyes; perfume; optical brighteners; rheology modifiers, structurants, thickeners, deposition aids; and mixtures thereof.

In one aspect of said composition said particles may have a cationic charge at a pH range from about 2 to about 10, from about 3 to about 9 or even from about 4 to about 8.

In one aspect of said composition, said composition may comprise a deposition aid that may comprise a polymer selected from the group comprising: polysaccharides, in one aspect, cationically modified starch and/or cationically modified guar; polysiloxanes; poly diallyl dimethyl ammonium halides; copolymers of poly diallyl dimethyl ammonium chloride and polyvinyl pyrrolidone; a composition comprising polyethylene glycol and polyvinyl pyrrolidone; acrylamides; imidazoles; imidazolinium halides; polyvinyl amine; copolymers of poly vinyl amine and N-vinyl formamide; polyvinylformamide, polyvinyl alcohol; polyvinyl alcohol crosslinked with boric acid; polyacrylic acid; polyglycerol ether silicone crosspolymers; polyacrylic acids, polyacrylates, copolymers of polyvinylamine and polvyinylalcohol oligimers of amines, in one aspect a diethylenetriamine, ethylene diamine, bis(3-aminopropyl)piperazine, N,N-Bis-(3-aminopropyl)methylamine, tris(2-aminoethyl)amine and mixtures thereof; polyethyleneimime, a derivatized polyethyleneimine, in one aspect an ethoxylated polyethyleneimine; a polymeric compound comprising, at least two moieties selected from the moieties consisting of a carboxylic acid moiety, an amine moiety, a hydroxyl moiety, and a nitrile moiety on a backbone of polybutadiene, polyisoprene, polybutadiene/styrene, polybutadiene/acrylonitrile, carboxyl-terminated polybutadiene/acrylonitrile or combinations thereof; pre-formed coacervates of anionic surfactants combined with cationic polymers; polyamines and mixtures thereof.

In one aspect of said composition at least 75% of said particles may have a fracture strength of from about 0.2 MPa to about 30 MPa; from about 0.6 MPa to about 10 MPa, from about 1.0 MPa to about 5 MPa, or even from about 1.2 MPa to about 3 MPa.

In one aspect of said composition said composition may comprise a rheology modifier, thickener and/or structurant having a high shear viscosity, at 20 sec$^{-1}$ shear rate and at 21° C., of from 1 to 7000 cps and a viscosity at low shear (0.5 sec$^{-1}$ shear rate at 21° C.) of greater than 1000 cps, or even 1000 cps to 200,000 cps. In one aspect, for cleaning and treatment compositions, such rheology modifiers may impart to the aqueous liquid composition a high shear viscosity, at 20 sec$^{-1}$ and at 21° C., of from 50 to 3000 cps and a viscosity at low shear (0.5 sec$^{-1}$ shear rate at 21° C.) of greater than 1000 cps, or even 1000 cps to 200,000 cps. In one aspect, suitable rheology modifiers, thickeners and/or structurants may be selected from the group consisting of polyacrylates, polymethacrylates, polycarboxylates, polymeric gums like pectine, alginate, arabinogalactan (gum Arabic), carrageenan, gellan gum, xanthan gum and guar gum, other non-gum polysaccharides like gellan gum, and combinations of these polymeric materials, hydroxyl-containing fatty acids, fatty esters or fatty waxes, castor oil and its derivatives, hydrogenated castor oil derivatives such as hydrogenated castor oil and hydrogenated castor wax; and mixtures thereof.

In one aspect of said composition said composition may be a fluid detergent that may comprise, based on total fluid detergent weight, less than about less then about 80% water, less than about 60% to about 2% water, from about 45% to about 7% water, from about 35% to about 9% water.

In one aspect of said composition said composition may have a viscosity of from about 10 cps to about 999 cps, or even from about 100 cps to about 800 cps at shear rate of 1 sec$^{-1}$.

In one aspect of said composition said composition may be a gel that may comprise, based on total gel weight, less than about 45% water less than about 45% to about 2% water, from about 45% to about 7% water, from about 35% to about 9% water and may have a neat viscosity of from about 1,000 cps to about 10,000 cps or even from about 1,200 cps to about 8,000 cps;

In one aspect of said composition said composition may be a fluid fabric enhancer; a solid fabric enhancer; a fluid shampoo; a solid shampoo; hair conditioner; body wash; solid antiperspirant; fluid antiperspirant; solid deodorant; fluid deodorant; fluid moisturizer; solid moisturizer; fluid lotion; fluid facial cleanser; solid facial cleanser; fluid cosmetic product; solid cosmetic product; fluid hair colorant composition; solid hair colorant composition; fluid detergent; solid detergent; fluid hard surface cleaner; solid hard surface cleaner; or a unit dose detergent comprising a detergent and a water soluble film encapsulating said detergent.

In one aspect, Applicants disclose a composition made by any of the processes disclosed in the present specification.

Aspects of the invention include the use of the particles of the present invention in laundry detergent compositions (e.g., TIDE™), hard surface cleaners (e.g., MR CLEAN™) automatic dishwashing liquids (e.g., CASCADE™), and floor cleaners (e.g., SWIFFER™) Non-limiting examples of cleaning compositions may include those described in U.S. Pat. Nos. 4,515,705; 4,537,706; 4,537,707; 4,550,862; 4,561,998; 4,597,898; 4,968,451; 5,565,145; 5,929,022; 6,294,514; and 6,376,445. The cleaning compositions disclosed herein are typically formulated such that, during use in aqueous cleaning operations, the wash water will have a pH of between about 6.5 and about 12, or between about 7.5 and 10.5. Liquid dishwashing product formulations typically have a pH between about 6.8 and about 9.0. Cleaning products are typically formulated to have a pH of from about 7 to about 12. Techniques for controlling pH at recommended usage levels include the use of buffers, alkalis, acids, etc., and are well known to those skilled in the art.

Aspects of the invention especially include the use of the particles in personal care compositions. The personal care compositions of the present invention can be applied to the skin and/or hair. The compositions can be, for example, formulated as bars, liquids, emulsions, shampoos, gels, powders, sticks, hair conditioners (rinse off and leave in), hair tonics, pastes, hair colorants, sprays, mousses and/or other styling products.

Personal Care Compositions

In one aspect, the consumer products disclosed herein may be personal care compositions comprising any aspect of the particles described in the present specification. Such compositions may be in solid or fluid form. Such compositions can be applied to the skin and/or hair or in other embodiments used to treat and/clean a situs. The compositions can be, for example, formulated as bars, liquids, emulsions, shampoos, gels, powders, sticks, hair conditioners (rinse off and leave in), hair tonics, pastes, hair colorants, sprays, mousses and other styling products.

In one embodiment, the particle is incorporated into a personal care composition suitable for use before, during or after hair removal. The personal care composition of the present invention can be used in combination with various hair removal applications (prior to, concurrently with, and/or after), including but not limited to shaving (wet or dry shaving, via electric razors, via powered or manual razors which can be reusable or disposable, and combinations thereof), epilation, electrolysis, wax or depilatories as well as energy delivery devices to help regulate hair growth. The hair removal composition can be an aerosol, such as an aerosol shave preparation which can be a foam, gel, or post foaming gel, or a non-aerosol shave preparation such as generally available in the market. In one embodiment, the shave preparation is an emulsion which can be in the form of a cream or lotion, or the shave preparation can be a gel, which most commonly consists of polymer thickened surfactant systems.

In one embodiment, the particle is incorporated into a shaving aid which can be incorporated into a shaving razor cartridge. Those of skill in the art will understand that shaving aids are also commonly referred to as lubricating strips. Suitable shaving aids and/or lubricating strips are disclosed in U.S. Pat. Nos. 7,069,658, 6,944,952, 6,594,904, 6,182,365, 6,185,822, 6,298,558 and 5,113,585, and U.S. Design Pat. No. D424,745. In one embodiment, the shaving aid comprises from about 50% to about 95% of a lubricious water soluble polymer, selected from the group consisting of polyethylene oxide; polyvinyl pyrrolidone, polyacrylamide, modified hydroxyalkyl cellulose, polyvinyl imidazoline, polyvinyl alcohol, polysulfone, polyhydroxyethyl-methacrylate, and mixture thereof. The shaving aid may also include from about 1% to about 50% of a non-soluble polymer selected from the group consisting of polyethylene, polypropylene, polystyrene, butadiene-styrene copolymer, polyacetal, acrylonitrile-butadiene-styrene copolymer, ethylene vinyl acetate copolymer, polyurethane, and mixtures thereof.

The compositions of the present inventions may include the following components:

A. Detersive Surfactant

The composition of the present invention may include a detersive surfactant. The detersive surfactant component may comprise anionic detersive surfactant, zwitterionic or amphoteric detersive surfactant, or a combination thereof. The concentration of the anionic surfactant component in the composition should be sufficient to provide the desired cleaning and lather performance, and generally range from about 5% to about 50%.

Anionic surfactants suitable for use in the compositions are the alkyl and alkyl ether sulfates. Other suitable anionic detersive surfactants are the water-soluble salts of organic, sulfuric acid reaction products conforming to the formula $[R^1—SO_3-M]$ where $R^1$ is a straight or branched chain, saturated, aliphatic hydrocarbon radical having from about 8 to about 24, or about 10 to about 18, carbon atoms; and M is a cation described hereinbefore. Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278.

Other anionic detersive surfactants suitable for use in the compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include olefin sulfonates having about 10 to about 24 carbon atoms. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880.

Another class of anionic detersive surfactants suitable for use in the compositions is the beta-alkyloxy alkane sulfonates. These surfactants conform to the formula

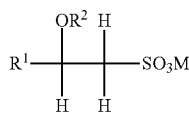

where $R^1$ is a straight chain alkyl group having from about 6 to about 20 carbon atoms, $R^2$ is a lower alkyl group having from about 1 to about 3 carbon atoms, or even 1 carbon atom, and M is a water-soluble cation as described hereinbefore.

U.S. Pat. Nos. 3,929,678, 2,658,072; 2,438,091; 2,528,378.

B. Cationic Surfactant System

The composition of the present invention may comprise a cationic surfactant system. The cationic surfactant system can be one cationic surfactant or a mixture of two or more cationic surfactants. If present, the cationic surfactant system is included in the composition at a level by weight of from about 0.1% to about 10%, from about 0.5% to about 8%, from about 1% to about 5%, or even from about 1.4% to about 4%, in view of balance among ease-to-rinse feel, rheology and wet conditioning benefits.

A variety of cationic surfactants including mono- and di-alkyl chain cationic surfactants can be used in the compositions of the present invention. Examples of suitable materials include mono-alkyl chain cationic surfactants in view of the desired gel matrix and wet conditioning benefits. The mono-alkyl cationic surfactants are those having one long alkyl chain which has from 12 to 22 carbon atoms, from 16 to 22 carbon atoms, or a $C_{18}$-$C_{22}$ alkyl group, in view of providing balanced wet conditioning benefits. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms. Such mono-alkyl cationic surfactants include, for example, mono-alkyl quaternary ammonium salts and mono-alkyl amines. Mono-alkyl quaternary ammonium salts include, for example, those having a non-functionalized long alkyl chain. Mono-alkyl amines include, for example, mono-alkyl amidoamines and salts thereof.

Mono-long alkyl quaternized ammonium salts useful herein are those having the formula (II):

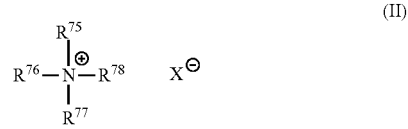

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. In one aspect, one of $R^{75}$, $R^{76}$, $R^{77}$ and $R^{78}$ is selected from an alkyl group of from 12 to 30 carbon atoms, in another aspect, from 16 to 22 carbon atoms, in another aspect, from 18 to 22 carbon atoms, or even 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Examples of suitable mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt. Among them, highly useful materials are behenyl trimethyl ammonium salt and stearyl trimethyl ammonium salt.

Mono-alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; in one aspect, l-glutamic acid, lactic acid, citric acid are highly useful. In one aspect, amines herein are partially neutralized with any of the acids at a molar ratio of the amine to the acid of from about 1:0.3 to about 1:2, or even from about 1:0.4 to about 1:1.

Although the mono-alkyl chain cationic surfactants are useful, other cationic surfactants such as di-alkyl chain cationic surfactants may also be used alone, or in combination with the mono-alkyl chain cationic surfactants. Such di-alkyl chain cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

C. High Melting Point Fatty Compound

The composition of the present invention may include a high melting point fatty compound. The high melting point fatty compound useful herein has a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section.

Among a variety of high melting point fatty compounds, fatty alcohols are used in one aspect the present invention. The fatty alcohols useful herein are those having from about 14 to about 30 carbon atoms, or even from about 16 to about 22 carbon atoms. These fatty alcohols are saturated and can be straight or branched chain alcohols. In one aspect, fatty alcohols include, for example, cetyl alcohol, stearyl alcohol, behenyl alcohol, and mixtures thereof.

High melting point fatty compounds of a single compound of high purity are typically used. In one aspect, single compounds of pure fatty alcohols selected from the group of pure cetyl alcohol, stearyl alcohol, and behenyl alcohol are employed. By "pure" herein, what is meant is that the compound has a purity of at least about 90%, or even at least about 95%. These single compounds of high purity provide good rinsability from the hair when the consumer rinses off the composition.

The high melting point fatty compound is included in the composition at a level of from about 0.1% to about 40%, from about 1% to about 30%, from about 1.5% to about 16% by weight of the composition, or even from about 1.5% to about 8% in view of providing improved conditioning benefits such as slippery feel during the application to wet hair, softness and moisturized feel on dry hair.

D. Cationic Polymers

The compositions of the present invention may contain a cationic polymer. Concentrations of the cationic polymer in the composition typically range from about 0.05% to about 3%, in another embodiment from about 0.075% to about 2.0%, and in yet another embodiment from about 0.1% to about 1.0%. Suitable cationic polymers will have cationic charge densities of at least about 0.5 meq/gm, in another embodiment at least about 0.9 meq/gm, in another embodiment at least about 1.2 meq/gm, in yet another embodiment at least about 1.5 meq/gm, but in one embodiment also less than about 7 meq/gm, and in another embodiment less than about 5 meq/gm, at the pH of intended use of the composition, which pH will generally range from about pH 3 to about pH 9, in one embodiment between about pH 4 and about pH 8. Herein, "cationic charge density" of a polymer refers to the ratio of the number of positive charges on the polymer to the molecular weight of the polymer. The average molecular weight of such suitable cationic polymers will generally be between about 10,000 and 10 million, in one embodiment between about 50,000 and about 5 million, and in another embodiment between about 100,000 and about 3 million.

Suitable cationic polymers for use in the compositions of the present invention contain cationic nitrogen-containing moieties such as quaternary ammonium or cationic protonated amino moieties. The cationic protonated amines can be primary, secondary, or tertiary amines (in one aspect, secondary or tertiary), depending upon the particular species and the selected pH of the composition. Any anionic counterion can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate and methyl sulfate.

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquaternium 6 and Polyquaternium 7, respectively); amphoteric copolymers of acrylic acid including copolymers of acrylic acid and dimethyldiallylammonium chloride (referred to in the industry by CTFA as Polyquaternium 22), terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methyl acrylate (referred to in the industry by CTFA as Polyquaternium 47). In one aspect, cationic substituted monomers may be the cationic substituted dialkylaminoalkyl acrylamides, dialkylaminoalkyl methacrylamides, and combinations thereof. Such monomers conform to the formula

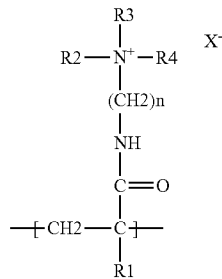

wherein $R^1$ is hydrogen, methyl or ethyl; each of $R^2$, $R^3$ and $R^4$ are independently hydrogen or a short chain alkyl having from about 1 to about 8 carbon atoms, from about 1 to about 5 carbon atoms, or even from about 1 to about 2 carbon atoms; n is an integer having a value of from about 1 to about 8, or even from about 1 to about 4; and X is a counterion. The nitrogen attached to $R^2$, $R^3$ and $R^4$ may be a protonated amine (primary, secondary or tertiary), but is in one aspect, a quaternary ammonium wherein each of $R^2$, $R^3$ and $R^4$ are alkyl groups a non limiting example of which is polymethacrylamidopropyl trimonium chloride, available under the trade name Polycare®133, from Rhone-Poulenc, Cranberry, N.J., U.S.A.

Other suitable cationic polymers for use in the composition include polysaccharide polymers, such as cationic cellulose derivatives and cationic starch derivatives. Suitable cationic polysaccharide polymers include those which conform to the formula

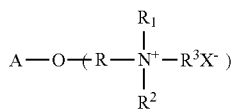

wherein A is an anhydroglucose residual group, such as a starch or cellulose anhydroglucose residual; R is an alkylene oxyalkylene, polyoxyalkylene, or hydroxyalkylene group, or combination thereof; $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) is typically about 20 or less; and X is an anionic counterion as described in hereinbefore.

Useful cationic cellulose polymers include salts of hydroxyethyl cellulose reacted with trimethyl ammonium substituted epoxide, referred to in the industry (CTFA) as Polyquaternium 10 and available from Amerchol Corp. (Edison, N.J., USA) in their Ucare™ Polymer LR, Ucare™ Polymer JR, and Ucare™ Polymer KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the trade name Ucare™ Polymer LM-200.

Other suitable cationic polymers include cationic guar gum derivatives, such as guar hydroxypropyltrimonium chloride, specific examples of which include the Jaguar series commercially available from Rhone-Poulenc Incorporated and the N-Hance® series commercially available from Aqualon Division of Hercules, Inc. Other suitable cationic polymers include quaternary nitrogen-containing cellulose ethers, some examples of which are described in U.S. Pat. No. 3,962,418. Other suitable polymers include synthetic polymers such as those disclosed in U.S. Publication No. 2007/0207109A1. Other suitable cationic polymers include copolymers of etherified cellulose, guar and starch, some examples of which are described in U.S. Pat. No. 3,958,581. When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

E. Nonionic Polymers

The composition of the present invention may include a nonionic polymer. Polyalkylene glycols having a molecular weight of more than about 1000 are useful herein. Useful are those having the following general formula:

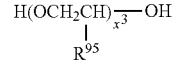

wherein $R^{95}$ is selected from the group consisting of H, methyl, and mixtures thereof. Polyethylene glycol polymers useful herein are PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

F. Conditioning Agents

Conditioning agents, and in particular silicones, may be included in the composition. Conditioning agents include any material which is used to give a particular conditioning benefit to hair and/or skin. In hair treatment compositions, suitable conditioning agents are those which deliver one or more benefits relating to shine, softness, compatibility, antistatic properties, wet-handling, damage, manageability, body, and greasiness. The conditioning agents useful in the compositions of the present invention typically comprise a water insoluble, water dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Such conditioning agents should be physically and chemically compatible with the essential components of the composition, and should not otherwise unduly impair product stability, aesthetics or performance.

The concentration of the conditioning agent in the composition should be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

1. Silicones

The conditioning agent of the compositions of the present invention can be an insoluble silicone conditioning agent. The silicone conditioning agent particles may comprise volatile silicone, non-volatile silicones, or combinations thereof. In one aspect, non-volatile silicones conditioning agents are employed. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

The concentration of the silicone conditioning agent typically ranges from about 0.01% to about 10%, from about 0.1% to about 8%, from about 0.1% to about 5%, or even from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609. The silicone conditioning agents for use in the compositions of the present invention typically have a viscosity, as measured at 25° C., from about 20 centistokes to about 2,000,000 centistokes ("cst"), from about 1,000 cst to about 1,800,000 cst, from about 50,000 cst to about 1,500,000 cst, or even from about 100,000 cst to about 1,500,000 csk.

The dispersed silicone conditioning agent particles typically have a number average particle diameter ranging from about 0.01 µm to about 50 µm. For small particle application to hair, the number average particle diameters typically range from about 0.01 µm to about 4 µm, from about 0.01 µm to about 2 µm, or even from about 0.01 µm to about 0.5 µm. For larger particle application to hair, the number average particle diameters typically range from about 4 µm to about 50 µm, from about 6 µm to about 30 µm, from about 9 µm to about 20 µm, or even from about 12 µm to about 18 µm.

a. Silicone Oils

Silicone fluids may include silicone oils, which are flowable silicone materials having a viscosity, as measured at 25° C., less than 1,000,000 cst, from about 5 cst to about 1,000,000 cst, or even from about 100 cst to about 600,000 cst. Suitable silicone oils for use in the compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

b. Amino and Cationic Silicones

Compositions of the present invention may include an aminosilicone. Aminosilicones, as provided herein, are silicones containing at least one primary amine, secondary amine, tertiary amine, or a quaternary ammonium group. Useful aminosilicones may have less than about 0.5% nitrogen by weight of the aminosilicone, less than about 0.2%, or even less than about 0.1%. Higher levels of nitrogen (amine functional groups) in the amino silicone tend to result in less friction reduction, and consequently less conditioning benefit from the aminosilicone. It should be understood that in some product forms, higher levels of nitrogen are acceptable in accordance with the present invention.

In one aspect, the aminosilicones used in the present invention have a particle size of less than about 50µ once incorporated into the final composition. The particle size measurement is taken from dispersed droplets in the final composition. Particle size may be measured by means of a laser light scattering technique, using a Horiba model LA-930 Laser Scattering Particle Size Distribution Analyzer (Horiba Instruments, Inc.).

In one embodiment, the aminosilicone typically has a viscosity of from about 1,000 cst (centistokes) to about 1,000,000 cst, from about 10,000 to about 700,000 cst, from about 50,000 cst to about 500,000 cst, or even from about 100,000 cst to about 400,000 cst. This embodiment may also comprise a low viscosity fluid, such as, for example, those materials described below in Section F.(1). The viscosity of aminosilicones discussed herein is measured at 25° C.

In another embodiment, the aminosilicone typically has a viscosity of from about 1,000 cst to about 100,000 cst, from about 2,000 cst to about 50,000 cst, from about 4,000 cst to about 40,000 cst, or even from about 6,000 cst to about 30,000 cs.

The aminosilicone typically is contained in the composition of the present invention at a level by weight of from about 0.05% to about 20%, from about 0.1% to about 10%, and or even from about 0.3% to about 5%.

c. Silicone Gums

Other silicone fluids suitable for use in the compositions of the present invention are the insoluble silicone gums. These gums are polyorganosiloxane materials having a viscosity, as measured at 25° C., of greater than or equal to 1,000,000 csk. Specific non-limiting examples of silicone gums for use in the compositions of the present invention include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

d. High Refractive Index Silicones

Other non-volatile, insoluble silicone fluid conditioning agents that are suitable for use in the compositions of the present invention are those known as "high refractive index silicones," having a refractive index of at least about 1.46, at least about 1.48, m at least about 1.52, or even at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (III) above, as well as cyclic polysiloxanes such as those represented by Formula (VIII) below:

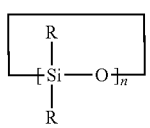

wherein R is as defined above, and n is a number from about 3 to about 7, or even from about 3 to about 5.

Silicone fluids suitable for use in the compositions of the present invention are disclosed in U.S. Pat. Nos. 2,826,551, 3,964,500, and 4,364,837.

e. Silicone Resins

Silicone resins may be included in the conditioning agent of the compositions of the present invention. These resins are highly cross-linked polymeric siloxane systems. The crosslinking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit Sift. Primes of the unit symbols (e.g. M', D', T', and Q') denote substituents other than methyl, and must be specifically defined for each occurrence.

In one aspect, silicone resins for use in the compositions of the present invention include, but are not limited to MQ, MT, MTQ, MDT and MDTQ resins. In one aspect, Methyl is a highly suitable silicone substituent. In another aspect, silicone resins are typically MQ resins, wherein the M:Q ratio is typically from about 0.5:1.0 to about 1.5:1.0 and the average molecular weight of the silicone resin is typically from about 1000 to about 10,000.

f. Modified Silicones or Silicone Copolymers

Other modified silicones or silicone copolymers are also useful herein. Examples of these include silicone-based quaternary ammonium compounds (Kennan quats) disclosed in U.S. Pat. Nos. 6,607,717 and 6,482,969; end-terminal quaternary siloxanes; silicone aminopolyalkyleneoxide block copolymers disclosed in U.S. Pat. Nos. 5,807, 956 and 5,981,681; hydrophilic silicone emulsions disclosed in U.S. Pat. No. 6,207,782; and polymers made up of one or more crosslinked rake or comb silicone copolymer segments disclosed in U.S. Pat. No. 7,465,439. Additional modified silicones or silicone copolymers useful herein are described in US Patent Application Nos. 2007/0286837A1 and 2005/0048549A1.

In alternative embodiments of the present invention, the above-noted silicone-based quaternary ammonium compounds may be combined with the silicone polymers described in U.S. Pat. Nos. 7,041,767 and 7,217,777 and US Application number 2007/0041929A1.

2. Organic Conditioning Oils

The compositions of the present invention may also comprise from about 0.05% to about 3%, from about 0.08% to about 1.5%, or even from about 0.1% to about 1%, of at least one organic conditioning oil as the conditioning agent, either alone or in combination with other conditioning agents, such as the silicones (described herein). Suitable conditioning oils include hydrocarbon oils, polyolefins, and fatty esters. Suitable hydrocarbon oils include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils are typically from about $C_{12}$ to about $C_{19}$. Branched chain hydrocarbon oils, including hydrocarbon polymers, typically will contain more than 19 carbon atoms. Suitable polyolefins include liquid polyolefins, liquid poly-α-olefins, or even hydrogenated liquid poly-α-olefins. Polyolefins for use herein may be prepared by polymerization of $C_4$ to about $C_{14}$ or even $C_6$ to about $C_{12}$. Suitable fatty esters include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

3. Other Conditioning Agents

Also suitable for use in the compositions herein are the conditioning agents described by the Procter & Gamble Company in U.S. Pat. Nos. 5,674,478, and 5,750,122. Also suitable for use herein are those conditioning agents described in U.S. Pat. Nos. 4,529,586, 4,507,280, 4,663,158, 4,197,865, 4,217, 914, 4,381,919, and 4,422, 853.

G. Anti-Dandruff Actives

The compositions of the present invention may also contain an anti-dandruff agent. Suitable, non-limiting examples of anti-dandruff actives include: antimicrobial actives, pyridinethione salts, azoles, selenium sulfide, particulate sulfur, keratolytic acid, salicylic acid, octopirox (piroctone olamine), coal tar, and combinations thereof. In one aspect, the anti-dandruff actives typically are pyridinethione salts. Such anti-dandruff particulate should be physically and chemically compatible with the essential components of the composition, and should not otherwise unduly impair product stability, aesthetics or performance.

Pyridinethione anti-dandruff agents are described, for example, in U.S. Pat. Nos. 2,809,971; 3,236,733; 3,753,196; 3,761,418; 4,345,080; 4,323,683; 4,379,753; and 4,470,982. It is contemplated that when ZPT is used as the anti-dandruff particulate in the compositions herein, that the growth or re-growth of hair may be stimulated or regulated, or both, or that hair loss may be reduced or inhibited, or that hair may appear thicker or fuller.

H. Humectant

The compositions of the present invention may contain a humectant. The humectants herein are selected from the group consisting of polyhydric alcohols, water soluble alkoxylated nonionic polymers, and mixtures thereof. The humectants, when used herein, are typically used at levels of from about 0.1% to about 20%, or even from about 0.5% to about 5%.

I. Suspending Agent

The compositions of the present invention may further comprise a suspending agent at concentrations effective for suspending water-insoluble material in dispersed form in the compositions or for modifying the viscosity of the composition. Such concentrations range from about 0.1% to about 10%, or even from about 0.3% to about 5.0%.

Suspending agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carrageenan, pectin, agar, quince seed (*Cydonia oblonga* Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Commercially available viscosity modifiers highly useful herein include Carbomers with trade names Carbopol® 934, Carbopol® 940, Carbopol® 950, Carbopol® 980, and Carbopol® 981, all available from B. F. Goodrich Company, acrylates/steareth-20 methacrylate copolymer with trade name ACRYSOL™ 22 available from Rohm and Hass, nonoxynyl hydroxyethylcellulose with trade name Amercell™ POLYMER HM-1500 available from Amerchol, methylcellulose with trade name BENECEL®, hydroxyethyl cellulose with trade name NATROSOL®, hydroxypropyl cellulose with trade name KLUCEL®, cetyl hydroxyethyl cellulose with trade name POLYSURF® 67, all supplied by Hercules, ethylene oxide and/or propylene oxide based polymers with trade names CARBOWAX® PEGs, POLYOX WASRs, and UCON® FLUIDS, all supplied by Amerchol.

Other optional suspending agents include crystalline suspending agents which can be categorized as acyl derivatives, long chain amine oxides, and mixtures thereof. These suspending agents are described in U.S. Pat. No. 4,741,855.

These suspending agents include ethylene glycol esters of fatty acids in one aspect having from about 16 to about 22 carbon atoms. In one aspect, useful suspending agents include ethylene glycol stearates, both mono and distearate, but in one aspect, the distearate containing less than about 7% of the mono stearate. Other suitable suspending agents include alkanol amides of fatty acids, having from about 16 to about 22 carbon atoms, or even about 16 to 18 carbon atoms, examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin® R available from Rheox, Inc. Long chain acyl derivatives, ethylene glycol esters of long chain carboxylic acids, long chain amine oxides, and alkanol amides of long chain carboxylic acids in addition to the materials listed above may be used as suspending agents.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl dimethyl amine oxides, e.g., stearyl dimethyl amine oxide.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

J. Aqueous Carrier

The formulations of the present invention can be in the form of pourable liquids (under ambient conditions). Such compositions will therefore typically comprise an aqueous carrier, which is present at a level of from about 20% to about 95%, or even from about 60% to about 85%. The aqueous carrier may comprise water, or a miscible mixture of water and organic solvent, and in one aspect may comprise water with minimal or no significant concentrations of organic solvent, except as otherwise incidentally incorporated into the composition as minor ingredients of other essential or optional components.

The carrier useful in the present invention includes water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

K. Dispersed Particles

The compositions may optionally comprise particles. The particles may be dispersed water-insoluble particles. The particles may be inorganic, synthetic, or semi-synthetic. In one embodiment, the particles have an average mean particle size of less than about 300 μm.

L. Gel Matrix

The above cationic surfactants, together with high melting point fatty compounds and an aqueous carrier, may form a gel matrix in the composition of the present invention.

The gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, from about 1:1 to about 1:10, or even from about 1:1 to about 1:6.

M. Skin Care Actives

The composition may comprise at least one skin care active, useful for regulating and/or improving the condition and/or appearance of mammalian skin. The skin care active may be soluble in oil or water, and may be present primarily in the oil phase and/or in the aqueous phase. Suitable actives include, but are not limited to, vitamins, peptides, sugar amines, sunscreens, oil control agents, tanning actives, anti-acne actives, desquamation actives, anti-cellulite actives, chelating agents, skin lightening agents, flavonoids, protease inhibitors, non-vitamin antioxidants and radical scavengers, hair growth regulators, anti-wrinkle actives, anti-atrophy actives, minerals, phytosterols and/or plant hormones, tyrosinase inhibitors, anti-inflammatory agents, N-acyl amino acid compounds, antimicrobials, and antifungals.

The composition may comprise from about 0.001% to about 10%, alternatively from about 0.01% to about 5%, of at least one vitamin. Herein, "vitamins" means vitamins, pro-vitamins, and their salts, isomers and derivatives. Non-limiting examples of suitable vitamins include: vitamin B compounds (including B1 compounds, B2 compounds, B3 compounds such as niacinamide, niacinnicotinic acid, tocopheryl nicotinate, $C_1$-$C_{18}$ nicotinic acid esters, and nicotinyl alcohol; B5 compounds, such as panthenol or "pro-B5", pantothenic acid, pantothenyl; B6 compounds, such as pyroxidine, pyridoxal, pyridoxamine; carnitine, thiamine, riboflavin); vitamin A compounds, and all natural and/or synthetic analogs of Vitamin A, including retinoids, retinol, retinyl acetate, retinyl palmitate, retinoic acid, retinaldehyde, retinyl propionate, carotenoids (pro-vitamin A), and other compounds which possess the biological activity of Vitamin A; vitamin D compounds; vitamin K compounds; vitamin E compounds, or tocopherol, including tocopherol sorbate, tocopherol acetate, other esters of tocopherol and tocopheryl compounds; vitamin C compounds, including ascorbate, ascorbyl esters of fatty acids, and ascorbic acid derivatives, for example, ascorbyl phosphates such as magnesium ascorbyl phosphate and sodium ascorbyl phosphate, ascorbyl glucoside, and ascorbyl sorbate; and vitamin F compounds, such as saturated and/or unsaturated fatty acids. In one embodiment, the composition may comprise a vitamin selected from the group consisting of vitamin B compounds, vitamin C compounds, vitamin E compounds and mixtures thereof. Alternatively, the vitamin is selected from the group consisting of niacinamide, tocopheryl nicotinate, pyroxidine, panthenol, vitamin E, vitamin E acetate, ascorbyl phosphates, ascorbyl glucoside, and mixtures thereof.

The composition may comprise one or more peptides. Herein, "peptide" refers to peptides containing ten or fewer amino acids, their derivatives, isomers, and complexes with other species such as metal ions (for example, copper, zinc, manganese, and magnesium). As used herein, peptide refers to both naturally occurring and synthesized peptides. In one embodiment, the peptides are di-, tri-, tetra-, penta-, and hexa-peptides, their salts, isomers, derivatives, and mixtures thereof. Examples of useful peptide derivatives include, but are not limited to, peptides derived from soy proteins, carnosine (beta-alanine-histidine), palmitoyl-lysine-threonine (pal-KT) and palmitoyl-lysine-threonine-threonine-lysine-serine (pal-KTTKS, available in a composition known as MATRIXYL®), palmitoyl-glycine-glutamine-proline-arginine (pal-GQPR, available in a composition known as RIGIN®), these three being available from Sederma, France, acetyl-glutamate-glutamate-methionine-glutamine-arginine-arginine (Ac-EEMQRR; Argireline®), and Cu-histidine-glycine-glycine (Cu-HGG, also known as IAMIN®). The compositions may comprise from about $1 \times 10^{-7}$% to about 20%, alternatively from about $1 \times 10^{-6}$% to about 10%, and alternatively from about $1 \times 10^{-5}$% to about 5% of the peptide.

The composition may comprise a sugar amine, also known as amino sugars, and their salts, isomers, tautomers and derivatives. Sugar amines can be synthetic or natural in origin and can be used as pure compounds or as mixtures of compounds (e.g., extracts from natural sources or mixtures of synthetic materials). For example, glucosamine is generally found in many shellfish and can also be derived from fungal sources. Examples of sugar amines include glucosamine, N-acetyl glucosamine, mannosamine, N-acetyl mannosamine, galactosamine, N-acetyl galactosamine, their isomers (e.g., stereoisomers), and their salts (e.g., HCl salt). Other sugar amine compounds useful in skin care compositions include those described in U.S. Pat. No. 6,159,485, issued to Yu, et al. In one embodiment, the composition may comprise from about 0.01% to about 15%, alternatively from about 0.1% to about 10%, and alternatively from about 0.5% to about 5%, of the sugar amine.

The composition may comprise one or more sunscreen actives (or sunscreen agents) and/or ultraviolet light absorbers. Herein, suitable sunscreen actives include oil-soluble sunscreens, insoluble sunscreens, and water-soluble sunscreens. In certain embodiments, the composition may comprise from about 1% to about 20%, or, alternatively, from about 2% to about 10%, by weight of the composition, of the sunscreen active and/or ultraviolet light absorber. Exact amounts will vary depending upon the chosen sunscreen active and/or ultraviolet light absorber and the desired Sun Protection Factor (SPF), and are within the knowledge and judgment of one of skill in the art.

Non-limiting examples of suitable oil-soluble sunscreens include benzophenone-3, bis-ethylhexyloxyphenol methoxyphenyl triazine, butyl methoxydibenzoyl-methane, diethylamino hydroxy-benzoyl hexyl benzoate, drometrizole trisiloxane, ethylhexyl methoxy-cinnamate, ethylhexyl salicylate, ethylhexyl triazone, octocrylene, homosalate, polysilicone-15, and derivatives and mixtures thereof.

Non-limiting examples of suitable insoluble sunscreens include methylene bis-benzotriazolyl tetramethylbutyl-phenol, titanium dioxide, zinc cerium oxide, zinc oxide, and derivatives and mixtures thereof.

Non-limiting examples of suitable water-soluble sunscreens include phenylbenzimidazole sulfonic acid (PBSA), terephthalylidene dicamphor sulfonic acid, (Mexoryl™ SX), benzophenone-4, benzophenone-5, benzylidene camphor sulfonic acid, cinnamidopropyl-trimonium chloride, methoxycinnamido-propyl ethyldimonium chloride ether, disodium bisethylphenyl triaminotriazine stilbenedisulfonate, disodium distyrylbiphenyl disulfonate, disodium phenyl dibenzimidazole tetrasulfonate, methoxycinnamido-propyl hydroxysultaine, methoxycinnamido-propyl laurdimonium tosylate, PEG-25 PABA (p-aminobenzoic acid), polyquaternium-59, TEA-salicylate, and salts, derivatives and mixtures thereof.

The composition may comprise one or more compounds for regulating the production of skin oil, or sebum, and for improving the appearance of oily skin. Examples of suitable oil control agents include salicylic acid, dehydroacetic acid, benzoyl peroxide, vitamin B3 compounds (for example, niacinamide or tocopheryl nicotinate), their isomers, esters, salts and derivatives, and mixtures thereof. The compositions may comprise from about 0.0001% to about 15%, alternatively from about 0.01% to about 10%, alternatively from about 0.1% to about 5%, and alternatively from about 0.2% to about 2%, of an oil control agent.

The composition may comprise a tanning active. The compositions may comprise from about 0.1% to about 20%, from about 2% to about 7%, or, alternatively, from about 3% to about 6%, by weight of the composition, of a tanning active. A suitable tanning active includes dihydroxyacetone, which is also known as DHA or 1,3-dihydroxy-2-propanone.

The composition may comprise a safe and effective amount of one or more anti-acne actives. Examples of useful anti-acne actives include resorcinol, sulfur, salicylic acid, erythromycin, zinc, and benzoyl peroxide. Suitable anti-acne actives are described in further detail in U.S. Pat. No. 5,607,980. The composition may comprise a safe and effective amount of a desquamation active such as from about 0.01% to about 10%, from about 0.5% to about 5%, or, alternatively, from about 0.1% to about 2%, by weight of the composition. For example, the desquamation actives tend to improve the texture of the skin (e.g., smoothness). A suitable desquamation system may comprise sulfhydryl compounds and zwitterionic surfactants and is described in U.S. Pat. No. 5,681,852. Another suitable desquamation system may comprise salicylic acid and zwitterionic surfactants and is described in U.S. Pat. No. 5,652,228.

The composition may comprise a safe and effective amount of an anti-cellulite agent. Suitable agents may include, but are not limited to, xanthine compounds (e.g., caffeine, theophylline, theobromine, and aminophylline).

Skin care compositions may comprise a safe and effective amount of a chelating agent such as from about 0.1% to about 10% or from about 1% to about 5% of the composition. Exemplary chelators are disclosed in U.S. Pat. No. 5,487,884. A suitable chelator is furildioxime and derivatives.

The composition may comprise a skin lightening agent. The compositions may comprise from about 0.1% to about 10%, from about 0.2% to about 5%, or, alternatively, from about 0.5% to about 2%, by weight of the composition, of a skin lightening agent. Suitable skin lightening agents include kojic acid, arbutin, tranexamic acid, ascorbic acid and derivatives (e.g., magnesium ascorbyl phosphate or sodium ascorbyl phosphate or other salts of ascorbyl phosphate), ascorbyl glucoside, and the like. Other suitable skin lightening materials include undecylenoyl phenylalanine (Sepiwhite® from SEPPIC), aloesin, Actiwhite® (Cognis), and Emblica® (Rona).

The composition compositions may comprise a flavonoid. The flavonoid can be synthetic materials or obtained as extracts from natural sources, which also further may be derivatized. Examples of classes of suitable flavonoids are disclosed in U.S. Pat. No. 6,235,773.

The composition may comprise protease inhibitors including, but are not limited to, hexamidine compounds, vanillin acetate, menthyl anthranilate, soybean trypsin inhibitor, Bowman-Birk inhibitor, and mixtures thereof. Skin care compositions can include hexamidine compounds, its salts, and derivatives. As used herein, "hexaminide compound" means a compound having the formula:

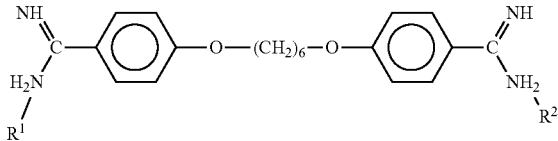

wherein $R^1$ and $R^2$ are optional or are organic acids (e.g., sulfonic acids, etc.). A particularly suitable hexamidine compound is hexamidine diisethionate.

The composition may other optional components such as non-vitamin antioxidants and radical scavengers, hair growth regulators, anti-wrinkle actives, anti-atrophy actives, minerals, phytosterols and/or plant hormones, tyrosinase inhibitors, anti-inflammatory agents, N-acyl amino acid compounds, antimicrobial or antifungal actives, and other useful skin care actives, which are described in further detail in U.S. application publication No. US 2006/0275237A1 and US 2004/0175347A1.

N. Color Cosmetics

The silicones of the present invention may also be used in cosmetic compositions, i.e., in products suitable for use in, on, or around the eyes, eyebrows, face, neck, chest, lips, hands, feet, or nails. Exemplary cosmetic products include eye liners, eye shadows, eyebrow pencils, mascaras, eye makeup removers, false eyelashes, under-eye concealers, eye creams, concealers, correctors, primers, blushes, bronzers, highlighters, shimmers, foundations, powders, sunscreens, brushes, face creams, lip primers, lip pencils, lipsticks, lip glosses, lip balms, lip stains, lip creams, and lotions. Examples of cosmetic products are found in U.S. Pat. No. 6,325,995 directed to an exemplary lip product; and U.S. Pat. No. 6,696,049 directed to an exemplary face product; and U.S. Pat. No. 6,503,495. The silicones of the present invention may be combined with materials commonly found in these compositions, such as alkyl dimethicone copolyols, polyols, hydrophilic skin treatment agents, carriers, thickening agent (such as solid waxes, gelling agents, inorganic thickeners, oil soluble polymers, fatty compounds, and mixtures thereof), pigments, film forming agents, preservatives, vitamins, etc. See U.S. Pat. No. 7,270,828 for examples.

O. Other Optional Components

The compositions of the present invention may contain also vitamins and amino acids such as: water soluble vitamins such as vitamin B1, B2, B6, B12, C, pantothenic acid, pantothenyl ethyl ether, panthenol, biotin, and their derivatives, water soluble amino acids such as asparagine, alanin, indole, glutamic acid and their salts, water insoluble vitamins such as vitamin A, D, E, and their salts and/or derivatives, water insoluble amino acids such as tyrosine, tryptamine, viscosity modifiers, dyes, nonvolatile solvents or diluents (water soluble and insoluble), pearlescent aids, foam boosters, additional surfactants or nonionic co-surfactants, pediculocides, pH adjusting agents, perfumes, preservatives, chelants, proteins, skin active agents, sunscreens, UV absorbers, vitamins, niacinamide, caffeine and minoxidil..

The compositions of the present invention may also contain pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C. I. Names. The compositions of the present invention may also contain antimicrobial agents which are useful as cosmetic biocides. The compositions of the present invention may also contain chelating agents.

The compositions of the present invention may include oxidative dye compounds in the form of primary intermediates (developers) or couplers. The compounds suitable for use in the inventive compositions (including those optionally added), in so far as they are bases, may be used as free bases or in the form of their physiologically compatible salts with organic or inorganic acids, such as hydrochloric, hydrobromic, citric, acetic, lactic, succinic, tartaric, or sulfuric acids, or, in so far as they have aromatic hydroxyl groups, in the form of their salts with bases, such as alkali phenolates.

Developers

Suitable developers for use in the compositions described herein include, but are not limited to, p-phenylenediamine derivatives, e.g. benzene-1,4-diamine (commonly known as p-phenylenediamine); 2-chloro-benzene-1,4-diamine; N-phenyl-benzene-1,4-diamine; N-(2-ethoxyethyl)benzene-1,4-diamine; 2-[(4-amino-phenyl)-(2-hydroxy-ethyl)-amino]-ethanol (commonly known as N,N-bis(2-hydroxyethyl)-p-phenylenediamine); (2,5-diamino-phenyl)-methanol; 2-(2,5-diamino-phenyl)-ethanol; N-(4-aminophenyl)benzene-1,4-diamine; 2,6-dimethyl-benzene-1,4-diamine; 2-isopropyl-benzene-1,4-diamine; 1-[(4-aminophenyl)amino]-propan-2-ol; 2-propyl-benzene-1,4-diamine; 1,3-bis[(4-aminophenyl)(2-hydroxyethyl)amino]

propan-2-ol; N$^4$,N$^4$,2-trimethylbenzene-1,4-diamine; 2-methoxy-benzene-1,4-diamine; 1-(2,5-diaminophenyl)ethanol; 1-(2,5-diaminophenyl)ethane-1,2-diol; 2,3-dimethyl-benzene-1,4-diamine; N-(4-amino-3-hydroxy-phenyl)-acetamide; 2,6-di ethylbenzene-1,4-diamine; 2,5-dimethylbenzene-1,4-diamine; 2-thien-2-ylbenzene-1,4-diamine; 2-thien-3-ylbenzene-1,4-diamine; 2-pyri din-3-ylbenzene-1,4-diamine; 1,1'-biphenyl-2,5-diamine; 2-(methoxymethyl)benzene-1,4-diamine; 2-(aminomethyl)benzene-1,4-diamine; diaminophenoxy)ethanol; N-[2-(2,5-diaminophenoxy)ethyl]-acetamide; N,N-dimethylbenzene-1,4-diamine; N,N-diethylbenzene-1,4-diamine; N,N-dipropylbenzene-1,4-diamine; 2-[(4-aminophenyl)(ethyl)amino]ethanol; 2-[(4-amino-3-methyl-phenyl)-(2-hydroxy-ethyl)-amino]-ethanol; N-(2-methoxy ethyl)-benzene-1,4-diamine; 3-[(4-aminophenyl)amino]propan-1-ol; 3-[(4-aminophenyl)-amino]propane-1,2-diol; N-{4-[(4-aminophenyl)amino]buty}benzene-1,4-diamine; 2-[2-(2-{2-[(2,5-diaminophenyl)-oxy]ethoxy}ethoxy)ethoxy]benzene-1,4-diamine; 2,2'-[1,2-Ethanediyl-bis-(oxy-2,1-ethanediyloxy)]-bis-benzene-1,4-diamine; p-aminophenol derivatives such as: 4-amino-phenol (commonly known as p-aminophenol); 4-methylamino-phenol; 4-amino-3-methyl-phenol; 4-amino-2-hydroxymethyl-phenol; 4-amino-2-methyl-phenol; 4-amino-1-hydroxy-2-(2'-hydroxy ethylaminomethyl)benzene; 4-amino-2-methoxymethyl-phenol; 5-amino-2-hydroxy-benzoic acid; 1-(5-amino-2-hydroxy-phenyl)-ethane-1,2-diol; 4-amino-2-(2-hydroxy-ethyl)-phenol; 4-amino-3-(hydroxymethyl)phenol; 4-amino-3-fluoro-phenol; 4-amino-2-(aminomethyl)-phenol; 4-amino-2-fluoro-phenol; o-phenylenediamine derivatives such as: 3,4-Diaminobenzoic acid and salts thereof; o-aminophenol derivatives such as: 2-amino-phenol (commonly known as o-aminophenol); 2,4-diaminophenol; 2-amino-5-methyl-phenol; 2-amino-5-ethyl-phenol; 2-amino-6-methyl-phenol; N-(4-amino-3-hydroxy-phenyl)-acetamide; and 2-amino-4-methyl-phenol; and heterocyclic derivatives such as: pyrimidine-2,4,5,6-tetramine (commonly known as 2,4,5,6-tetraaminopyrimidine); 1-methyl-1H-pyrazole-4,5-diamine; 2-(4,5-diamino-1H-pyrazol-1-yl)ethanol; N$^2$,N$^2$-dimethyl-pyridine-2,5-diamine; 2-[(3-amino-6-methoxypyridin-2-yl)amino]ethanol; 6-methoxy-N$^2$-methyl-pyridine-2,3-diamine; pyridine-2,5-diamine; 1-isopropyl-1H-pyrazole-4,5-diamine; 1-(4-methylbenzyl)-1H-pyrazole-4,5-diamine; 1-(benzyl)-1H-pyrazole-4,5-diamine; 1-(4-chlorobenzyl)-1H-pyrazole-4,5-diamine; pyrazolo[1,5-a]-pyrimidine-3,7-diamine; 5,6,7-trimethylpyrazolo[1,5-a]pyrimidin-3-ylamine hydrochloride; 7-methy 1pyrazolo[1,5-a]pyrimidin-3-ylamine hydrochloride; 2,5,6,7-teramethyl-pyrazolo[1,5-a]pyrimidin-3-yl amine hydrochloride; 5,7-di-tert-butylpyrazolo[1,5-a]pyrimidin-3-ylamine hydrochloride; 5,7-di-trifluoromethyl-pyrazolo[1,5-a]pyrimidin-3-ylamine hydrochloride; 2-methylpyrazolo[1,5-a]pyrimidin-3,7-diamine hydrochloride; 4-hydroxy-2,5,6-tri aminopyrimidine; 2,3-diamino-6,7-dihydropyrazolo[1,2-a]pyrazol-1 (5H)-one dimethosulfonate and salts thereof.

Additional developers are selected from the group consisting of N-(3-furylmethyl)benzene-1,4-diamine; N-thiophen-3-ylmethyl-benzene-1,4-diamine; N-(2-furylmethyl)benzene-1,4-diamine; N-thiophen-2-ylmethyl-benzene-1,4-diamine; 3-(2,5-diamino-phenyl)-N-ethyl-acrylamide; 2-[3-(3-amino-phenylamino)-propenyl]-benzene-1,4-diamine; 2-[3-(4-amino-phenylamino)-propenyl]-benzene-1,4-diamine; 2-(6-methyl-pyridin-2-yl)-benzene-1,4-diamine; 2-pyridin-2-yl-benzene-1,4-diamine; 2-[3-(4-amino-phenylamino)-propenyl]-benzene-1,4-diamine; 2-[3-(3-amino-phenyl amino)-prop enyl]-benzene-1,4-diamine; 3-(2,5-di-amino-phenyl)-N-ethyl-acrylamide; 2-thiazol-2-yl-benzene-1,4-diamine; 3'-fluoro-biphenyl-2,5-diamine; 2-propenyl-benzene-1,4-diamine; 2'-chloro-biphenyl-2,5-diamine; 4'-methoxy-biphenyl-2,5-diamine; N-(4-amino-benzyl)-benzene-1,4-diamine; N-[4-amino-2-(2-hydroxy-ethyl)-2H-pyrazol-3-yl]-3-(5-amino-2-hydroxy-phenyl)-acrylamide hydrochloride; 4-amino-2-propylaminomethyl-phenol; 4-amino-2-(isopropylamino-methyl)-phenol hydrochloride; 4-amino-2-[(2-hydroxy-5-nitro-phenylamino)-methyl]-phenol hydrochloride; 4-amino-2-(pyridin-3-ylaminomethyl)-phenol; 5-cyclobutylamino-2-methyl-phenol; 4,5-diamino-1-methyl-1H-pyrazole-3-carbonitrile; 3-methoxy-1-propyl-1H-pyrazole-4,5-diamine; 3-methoxy-1-(2-methoxy ethyl)-1H-pyrazole-4,5-diamine; 1-(2-aminoethyl)-3-methoxy-1H-pyrazole-4,5-diamine; 8-methoxy-1,2,4,5-tetrahydropyrazolo[5,1-d][1,3,5]oxadiazepin-9-amine; 1-(2-hydroxy ethyl)-3-methoxy-1H-pyrazol-4,5-diamine; 1-cyclohexyl-3-methoxy-1H-pyrazole-4,5-diamine; 6-methoxy-1-methyl-2,3-dihydro-1H-imidazo[1,2-b]pyrazol-7-amine; 2-methoxy-4,5,6,7-tetrahydropyrazolo[1,5-a]pyrimidin-3-amine; 3-methoxy-1-octyl-1H-pyrazole-4,5-diamine; 3-methoxy-1-pentyl-1H-pyrazole-4,5-diamine; 6-methoxy-2,3-dihydro-1H-imidazo[1,2-b]pyrazol-7-amine; 3-methoxy-N$^5$,N$^5$-dimethyl-1-propyl-1H-pyrazole-4,5-diamine; 1-hexyl-3-methoxy-1H-pyrazole-4,5-diamine; 1-butyl-3-methoxy-1H-pyrazole-4,5-diamine; 1-isopropyl-3-methoxy-1H-pyrazole-4,5-diamine; 1-ethyl-3-methoxy-1H-pyrazole-4,5-diamine; 3-methoxy-1-(4-methoxy benzyl)-1H-pyrazole-4,5-diamine; 3-methoxy-1-(pyri din-2-yl)-1H-pyrazole-4,5-diamine; 1-(4-ethylphenyl)-3-methoxy-1H-pyrazole-4,5-diamine; 3-methoxy-1-p-tolyl-1H-pyrazole-4,5-diamine; 3-cyano-1-(2-hydroxyethyl)-1H-pyrazole-4,5-diamine; 1-butyl-3-cyano-1H-pyrazole-4,5-diamine; 3-cyano-1-phenyl-1H-pyrazol-4,5-diamine; 3-cyano-1-hexyl-1H-pyrazole-4,5-diamine; 1-butyl-3-cyano-1H-pyrazol-4,5-diamine; 3-cyano-1-(4-methoxy benzyl)-1H-pyrazol-4,5-diamine; 3-cyano-1-isopropyl-1H-pyrazol-4,5-diamine; 1-cyclohexyl-3-fluoro-N$^5$-isopropyl-1H-pyrazole-4,5-diamine; 1-methyl-3-(trifluoromethoxy)-1H-pyrazole-4,5-diamine; 3-fluoro-1-octyl-1H-pyrazole-4,5-diamine; 3-chloro-1-hexyl-1H-pyrazole-4,5-diamine; 3-fluoro-1-(2-hydroxy ethyl)-1H-pyrazol-4,5-diamine; 3-chloro-1-(2-hydroxyethyl)-1H-pyrazol-4,5-diamine; 3-chloro-1-(4-hydroxy butyl)-1H-pyrazol-4,5-diamine; 3-chloro-1-(pyridin-2-yl)-1H-pyrazole-4,5-diamine; 3-chloro-1-phenyl-1H-pyrazole-4,5-diamine; 3-chloro-1-ethyl-1H-pyrazole-4,5-diamine; 1-(3-methoxypropyl)-3-(methylsulfinyl)-1H-pyrazole-4,5-diamine; 1-(3-hydroxypropyl)-3-(methylsulfinyl)-1H-pyrazole-4,5-diamine; 1-(4-methoxy benzyl)-3-(methylsulfonyl)-1H-pyrazole-4,5-diamine; 1-methyl-3-(methylsulfonyl)-1H-pyrazole-4,5-diamine; and salts thereof.

In some embodiments, developers include but are not limited to: p-phenylenediamine derivatives such as: 2-methyl-benzene-1,4-diamine; benzene-1,4-diamine; 1-(2,5-diamino-phenyl)-ethanol; 2-(methoxymethyl)benzene-1,4-diamine; N-(2-methoxy ethyl)benzene-1,4-diamine; 1-(2,5-diaminophenyl)ethane-1,2-diol; 1,3-bis(N-(2-hydroxy ethyl)-N-(4-amino-phenyl)amino)-2-propanol; 2,2'-[1,2-ethanediyl-bis-(oxy-2,1-ethanediyloxy)]-bis-benzene-1,4-diamine; N,N-bis(2-hydroxyethyl)-p-phenylenediamine; and mixtures thereof; p-aminophenol derivatives such as: 4-amino-phenol; 4-methylamino-phenol; 4-amino-3-methyl-phenol; 4-amino-2-methoxy methyl-phenol; 1-(5-amino-2-hydroxy-phenyl)-ethane-1,2-diol; 4-amino-2-aminomethylphenol; 4-amino-1-hydroxy-2-(2'-hydroxy ethylaminomethyl)benzene; 5-aminosalicylic acid and salts thereof; and mixtures thereof; o-phenylenediamine derivatives such as: 3,4-Diaminobenzoic acid and salts thereof; o-aminophenol derivatives such as: 2-amino-phenol; 2-amino-5-methyl-phenol; 2-amino-6-methyl-phenol; N-(4-amino-3-hydroxy-phenyl)-acetamide; 2-amino-4-methyl-phenol; 2-amino-5-ethyl-phenol; and mixtures thereof; and heterocyclic derivatives such as: pyrimidine-2,4,5,6-tetramine; 1-methyl-1H-pyrazole-4,5-diamine; 2-(4,5-diamino-1H-pyrazol-1-yl)ethanol; 1-(4-methylbenzyl)-1H-pyrazole-4,5-diamine; 1-(benzyl)-1H-pyrazole-4,5-diamine; $N^2,N^2$-di methyl-pyridine-2,5-diamine; 4-Hydroxy-2,5,6-triaminopyrimidine; salts thereof; and mixtures thereof.

In certain embodiments, developers include: 2-methyl-benzene-1,4-diamine; 2-(methoxy methyl)benzene-1,4-diamine; benzene-1,4-diamine; N,N-bis(2-hydroxyethyl)-p-phenylenediamine; 4-amino-phenol; 4-methylamino-phenol; 4-amino-3-methyl-phenol; 2-amino-phenol; 2-amino-5-methyl-phenol; 2-amino-5-ethyl-phenol; 2-amino-6-methyl-phenol; 1-methyl-1H-pyrazole-4,5-diamine; 2-(4,5-diamino-1H-pyrazol-1-yl)ethanol; 2,5-diaminotoluene; 2,5-diaminophenylethyl alcohol; salts thereof; and mixtures thereof.

Couplers

Suitable couplers for use in the compositions described herein include, but are not limited to: phenols, resorcinols, naphthols, m-aminophenols, m-phenylenediamines, and heterocyclic compounds, and derivatives thereof such as: 2-amino-5-ethyl-phenol; naphthalene-1,7-diol; benzene-1,3-diol; 4-chlorobenzene-1,3-diol; naphthalen-1-ol; 2-methyl-naphthalen-1-ol; naphthalene-1,5-diol; naphthalene-2,7-diol; benzene-1,4-diol; 2-methyl-benzene-1,3-diol; 7-amino-4-hydroxy-naphthalene-2-sulfonic acid; 1,2,3,4-tetrahydro-naphthalene-1,5-diol; 2-chloro-benzene-1,3-diol; 4-hydroxy-naphthalene-1-sulfonic acid; benzene-1,2,3-triol; naphthalene-2,3-diol; 5-chloro-2-methylbenzene-1,3-diol; 4,6-di chlorobenzene-1,3-diol; 2,3-dihydroxy-[1,4]naphthoquinone; and 1-Acetoxy-2-methylnaphthalene; m-phenylenediamines such as: 2,4-diaminophenol; benzene-1,3-diamine; 2-(2,4-diamino-phenoxy)-ethanol; 2-[(3-amino-phenyl)-(2-hydroxy-ethyl)-amino]-ethanol; 2-methyl-benzene-1,3-diamine; 2-[[2-(2,4-diamino-phenoxy)-ethyl]-(2-hydroxy-ethyl)-amino]-ethanol; 4-{3-[(2,4-diaminophenyl)oxy]propoxy}benzene-1,3-diamine; 2-(2,4-diamino-phenyl)-ethanol; 2-(3-amino-4-methoxy-phenyl amino)-ethanol; 4-(2-amino-ethoxy)-benzene-1,3-diamine; (2,4-diamino-phenoxy)-acetic acid; 2-[2,4-diamino-5-(2-hydroxy-ethoxy)-phenoxy]-ethanol; 4-ethoxy-6-methyl-benzene-1,3-diamine; 2-(2,4-diamino-5-methyl-phenoxy)-ethanol; 4,6-dimethoxy-benzene-1,3-diamine; 2-[3-(2-hydroxy-ethylamino)-2-methyl-phenyl amino]-ethanol; 3-(2,4-diamino-phenoxy)-propan-1-ol; N-[3-(dimethylamino) phenyl]urea; 4-methoxy-6-methylbenzene-1,3-diamine; 4-fluoro-6-methyl benzene-1,3-diamine; 2-({3-[(2-hydroxyethylamino]-4,6-dimethoxyphenyl}-amino)ethanol; 3-(2,4-diaminophenoxy)-propane-1,2-diol; 2-[2-amino-4-(methyl-amino)-phenoxy]ethanol; 2-[(5-amino-2-ethoxy-phenyl)-(2-hydroxy-ethyl)-amino]-ethanol; 2-[(3-aminophenyl)amino] ethanol; 2,4-Diamino-5-(2'-hydroxy ethyloxy)toluene; N,N-Dimethyl-3-ureidoaniline; N-(2-aminoethyl)benzene-1,3-diamine; 4-{[(2,4-diamino-phenyl)oxy]methoxy}-benzene-1,3-diamine; 1-methyl-2,6-bis(2-hydroxyethylamino) benzene; and 2,4-dimethoxybenzene-1,3-diamine; 1,3-bis-(2,4-diaminophenoxy)propane; 2-methyl-5-[(1-H-pyrrol-2-ylmethyl)-amino]-phenol; 5-[(furan-2-ylmethyl)-amino]-2-methyl-phenol; 5-isopropylamino-2-methyl-phenol; biphenyl-2,4,4'-tri amine hydrochloride; 5-(4-amino-phenyl)aminomethyl-benzene-1,3-diamine hydrochloride; 5-phenyl aminomethyl-benzene-1,3-diamine hydrochloride; 2-[4-amino-2-(3,5-diamino-benzylamino)-phenoxy]-ethanol hydrochloride; 5-(3-amino-phenyl)aminomethyl-benzene-1,3-diamine hydrochloride; N-(2-amino-benzyl)-benzene-1,3-diamine hydrochloride; N-furan-2-ylmethyl-benzene-1,3-diamine hydrochloride; 2-[(3-amino-phenyl amino)-methyl]-phenol hydrochloride; 4-amino-2-propylaminomethyl-phenol; N-benzo[1,3]dioxol-5-ylmethyl-benzene-1,3-diamine hydrochloride; N-[4-amino-2-(2-hydroxyethyl)-2H-pyrazol-3-yl]-3-(5-amino-2-hydroxy-phenyl)-acrylamide; 4-thiophen-3-yl-benzene-1,3-diamine; 5-phenylaminomethyl-benzene-1,3-diamine hydrochloride; 5-(3-amino-phenyl)aminomethyl-benzene-1,3-diamine hydrochloride; 4-thiophen-3-yl-benzene-1,3-diamine; 2',4'-diamino-biphenyl-4-ol; 5-cyclobutylamino-2-methyl-phenol; 5-cyclobutylamino-2-methyl-phenol; 4-amino-2-(pyridin-3-ylaminomethyl)-phenol; 5-(3-amino-phenyl) aminomethyl-benzene-1,3-diamine hydrochloride; 5-allylaminomethyl-benzene-1,3-diamine hydrochloride; N-(4-amino-benzyl)-benzene-1,3-diamine hydrochloride; N-benzyl-benzene-1,3-diamine hydrochloride; 3-[(3-amino-phenyl amino)-methyl]-phenol hydrochloride; N-(4-methoxy-benzyl)-benzene-1,3-diamine hydrochloride; N-thiophen-2-ylmethyl-benzene-1,3-diamine hydrochloride; 4-Amino-2-[(2-hydroxy-5-nitro-phenylamino)-methyl]-phenol; 2',4'-diamino-biphenyl-4-ol hydrochloride; biphenyl-2,4,4'-triamine; 5-(4-amino-phenyl)aminomethyl-benzene-1,3-diamine hydrochloride; 2-[4-amino-2-(3,5-diamino-benzylamino)-phenoxy]-ethanol hydrochloride; 5-allylaminomethyl-benzene-1,3-diamine hydrochloride; 5-(3-amino-phenyl)aminomethyl-benzene-1,3-diamine hydrochloride; N-(4-amino-benzyl)-benzene-1,3-diamine hydrochloride; N-benzyl-benzene-1,3-diamine hydrochloride; 3-[(3-amino-phenylamino)-methyl]-phenol hydrochloride; N-(2-amino-benzyl)-benzene-1,3-diamine hydrochloride; N-(4-methoxy-benzyl)-benzene-1,3-diamine hydrochloride; N-furan-2-ylmethyl-benzene-1,3-diamine hydrochloride; 2-[(3-amino-phenylamino)-methyl]-phenol hydrochloride; N-thiophen-2-ylmethyl-benzene-1,3-diamine hydrochloride; N-benzo[1,3]dioxol-5-ylmethyl-benzene-1,3-diamine hydrochloride; m-aminophenols such as: 3-amino-phenol; 2-(3-hydroxy-4-methyl-phenylamino)-acetamide; 2-(3-hydroxy-phenylamino)-acetamide; 5-amino-2-methyl-phenol; 3-amino-2,6-dimethylphenol; 5-(2-hydroxy-ethyl amino)-2-methyl-phenol; 5-amino-2,4-di chloro-phenol; 3-amino-2-methyl-phenol; 3-amino-2,6-dimethyl-phenol; 3-amino-2-chloro-6-methyl-phenol; 5-amino-2-(2-hydroxy-ethoxy)-phenol; 2-chloro-5-(2,2,2-trifluoro-ethylamino)-phenol; 5-amino-4-chloro-2-methyl-phenol; 3-cyclopentylamino-phenol; 5-[(2-hydroxyethyl)amino]-4-methoxy-2-methylphenol; 5-amino-4-methoxy-2-methylphenol; 3-(dimethyl amino)phenol; 3-(di ethyl amino)phenol; 5-amino-4-fluoro-2-methy 1phenol; 5-amino-4-ethoxy-2-methylphenol; 3-amino-2,4-di chloro-phenol; 3-[(2-methoxy ethyl)amino]phenol; 3-[(2-hydroxy-ethyl)amino]phenol; 5-amino-2-ethyl-phenol; 5-amino-2-methoxy phenol; 5-[(3-hydroxy-propyl)amino]-2-methylphenol; 3-[(3-hydroxy-2-methylphenyl)-amino] propane-1,2-diol; 3-[(2-hydroxy ethyl)amino]-2-methy 1phenol; 2-methyl-5-[(1-H-pyrrol-2-ylmethyl)-amino]-phenol; 5-[(furan-2-ylmethyl)-amino]-2-methyl-phenol; 5-isopropylamino-2-methyl-phenol;-cyclobutylamino-2-methyl-phenol and heterocyclic derivatives such as: 3,4-dihydro-2H-1,4-benzoxazin-6-ol; 6-methoxyquinolin-8-amine; 4-methylpyridine-2,6-diol; 2,3-dihydro-1,4-benzodioxin-5-ol; 1,3-benzodioxol-5-ol; 2-(1,3-benzodioxol-5-ylamino)

ethanol; 3,4-dimethylpyridine-2,6-diol; 5-chloropyridine-2,3-diol; 2,6-dimethoxypyridine-3,5-diamine; 1,3-benzodioxol-5-amine; 2-{[3,5-diamino-6-(2-hydroxyethoxy)-pyridin-2-yl]oxy}-ethanol; 1H-indol-4-ol; 5-amino-2,6-dimethoxy pyridin-3-ol; 1H-indole-5,6-diol; 1H-indol-7-ol; 1H-indol-5-ol; 1H-indol-6-ol; 6-bromo-1,3-benzodioxol-5-ol; 2-aminopyridin-3-ol; pyridine-2,6-diamine; 3-[(3,5-diaminopyridin-2-yl)oxy]propane-1,2-diol; 5-[(3,5-diaminopyridin-2-yl)oxy]pentane-1,3-diol; indoline-5,6-diol; 3,5-dimethoxy pyridine-2,6-diamine; 6-methoxy pyridine-2,3-diamine; 3,4-dihydro-2H-1,4-benzoxazin-6-amine; 4-hydroxy-N-methylindole; 1H-5-methy 1pyrazol-5-one; 1-phenyl-3-methylpyrazol-5-one; 2,6-dimethylpyrazolo[1,5-b]-1,2,4-triazole; 2,6-dimethyl[3,2-c]-1,2,4-triazole; 6-methylpyrazolo-[1,5-a]benzimidazole; 2,6-dihydroxypyridine; 2,6-dihydroxy-3,4-dimethylpyridine; 5-methyl pyrazolo[5,1-e]-1,2,3-triazole; 5-methyl-6-chloro-pyrazolo[5,1-e]-1,2,3-triazole; 5-phenylpyrazolo[5,1-e]-1,2,3-triazole and its addition salts; 1H-2,6-dimethylpyrazolo[1,5-b]-1,2,4-triazole tosylate; 7,8-dicyano-4-methylimidazolo-[3,2-a]imidazole; 2,7-dimethylpyrazolo[1,5-a]pyrimidin-5-one; 2,5-dimethylpyrazolo[1,5-a]pyrimidin-7-one; and 2-methyl-5-methoxymethyl-pyrazolo[1,5-a]pyrimidin-7-one; 6-hydroxybenzomorpholine; and 3-amino-2-methylamino-6-methoxypyridine; salts thereof, and mixtures thereof.

In some embodiments, couplers include but are not limited to: phenol, resorcinol, and naphthol derivatives such as: 2-amino-5-ethyl-phenol; naphthalene-1,7-diol; benzene-1,3-diol; 4-chlorobenzene-1,3-diol; naphthalen-1-ol; 2-methyl-naphthalen-1-ol; naphthalene-1,5-diol; naphthalene-2,7-diol; benzene-1,4-diol; 2-methyl-benzene-1,3-diol; and 2-isopropyl-5-methylphenol; 1,2,4-trihydroxybenzene; 1-acetoxy-2-methylnaphthalene; and mixtures thereof, m-phenylenediamine derivatives such as: benzene-1,3-diamine; 2-(2,4-diamino-phenoxy)-ethanol; 4-{3-[(2,4-diaminophenyl)oxy]propoxy}benzene-1,3-diamine; 2-(3-amino-4-methoxy-phenyl amino)-ethanol; 2-[2,4-diamino-5-(2-hydroxy-ethoxy)-phenoxy]-ethanol; and 3-(2,4-diamino-phenoxy)-propan-1-ol; 2,4-diamino-5-(2'-hydroxy ethyloxy)toluene; N,N-dimethyl-3-ureidoaniline; 2,4-diamino-5-fluorotoluene; 1-methyl-2,6-bis(2-hydroxyethylamino)benzene; and mixtures thereof; m-aminophenol derivatives such as: 3-aminophenol; 5-amino-2-methyl-phenol; 3-amino-2,6-dimethylphenol; 5-(2-hydroxy-ethyl-amino)-2-methyl-phenol; and 3-amino-2-methyl-phenol; 1-hydroxy-3-amino-2,4-dichlorobenzene; 1,3-bis-(2,4-diaminophenoxy)propane; 1-hydroxy-2-methyl-5-amino-6-chlorobenzene; 5-Amino-4-chloro-2-methylphenol; and mixtures thereof, and heterocyclic derivatives such as: 3,4-dihydro-2H-1,4-benzoxazin-6-ol; 1,3-benzodioxol-5-ol; 1,3-benzodioxol-5-amine; 1H-indol-4-ol; 1H-indole-5,6-diol; 1H-indol-7-ol; 1H-indol-5-ol; 1H-indol-6-ol; pyridine-2,6-diamine; 2-aminopyridin-3-ol; 4-hydroxy-N-methylindole; 1H-5-methylpyrazol-5-one; 1-phenyl-3-methylpyrazol-5-one; 2,6-dimethylpyrazolo[1,5-b]-1,2,4-triazole; 2,6-dimethyl[3,2-c]-1,2,4-triazole; 6-methylpyrazolo-[1,5-a]benzimidazole; 2,6-dihydroxypyridine; 2,6-dihydroxy-3,4-dimethylpyridine; 6-hydroxybenzomorpholine; 2,6-dihydroxy-3,4-dimethylpyridine; 3,5-diamino-2,6-dimethoxypyridine; 3-amino-2-methylamino-6-methoxypyridine; salts thereof, and mixtures thereof.

In certain embodiments, couplers include: 2-amino-5-ethyl-phenol; benzene-1,3-diol; 4-chlorobenzene-1,3-diol; 4,6-di chlorobenzene-1,3-diol; 2-methyl-benzene-1,3-diol; 2-amino-4-(2'-hydroxyethyl)aminoanisole; 2,4-diaminobenzyl alcohol; 2,4-diaminophenylethyl alcohol; m-phenylenediamine; 5-amino-2-methyl-phenol; 3-amino-2,6-dimethylphenol; 2,4-diaminophenoxy ethanol; 1-naphthol; 2-methyl-naphthol; 3-aminophenol; 3-amino-2-methyl phenol; 4-hydroxy-1,2-methylenedi oxy benzene; 4-amino-1,2-methylenedioxy benzene; 4-(2'-hydroxyethyl)amino-1,2-methylenedioxybenzene; 1-Methyl-2-hydroxy-4-(2'-hydroxy ethyl)aminobenzene; 2,4-diaminophenetole; 2,4-diamino-5-methy 1phenol e; 4-hydroxyindole; 3-amino-5-hydroxy-2,6-dimethoxy pyridine; and 3,5-diamino-2,6-dimethoxypyridine; benzene-1,3-diamine; 2-aminopyridin-3-ol; 1-phenyl-3-methylpyrazol-5-one; salts thereof; and mixtures thereof.

Additionally, in some embodiments, developers and couplers include 5-methoxymethyl-2-aminophenol; 5-ethyl-2-aminophenol; 5-phenyl-2-aminophenol; 5-cyanoethyl-2-aminophenol; salts thereof; and mixtures thereof.

Any of the developers and couplers described above may be combined to form a mixture of developers and couplers. The hair dye compositions of the present invention will generally comprise from about 0.001% to about 10% by weight of the dyeing composition of developer and coupler dyes. For example, compositions providing low intensity dyeing such as natural blond to light brown hair shades generally comprise from about 0.001% to about 5%, in some embodiments, from about 0.1% to about 2%, in certain embodiments, from about 0.2% to about 1% by weight of dyeing composition of developers and couplers. Darker shades such as browns and black typically comprise from 0.001% to about 10% by weight, in some embodiments, from about 0.05% to about 7% by weight, in certain embodiments, from about 1% to about 5% of developers and couplers. Developer compounds are generally used in approximately equimolar quantities with respect to coupler compounds. The developer compound may, however, be present in a greater or lesser quantity with respect to the coupler compound.

Direct Dyes

The inventive compositions may also comprise compatible direct dyes, in an amount sufficient to provide coloring, particularly with regard to intensity. Typically, such an amount will range from about 0.05% to about 4%, by weight of the dye composition. Suitable direct dyes include but are not limited to: Acid Yellow 1; Acid Orange 3; Disperse Red 17; Basic Brown 17; Acid Black 52; Acid Black 1; Disperse Violet 4; 4-nitro-o-phenylenediamine; 2-nitro-p-phenylenediamine; Picramic Acid; HC Red No. 13; 1,4-bis-(2'-hydroxyethyl)-amino-2-nitrobenzene; HC Yellow No. 5; HC Red No. 7; HC Blue No. 2; HC Yellow No. 4; HC Yellow No. 2; HC Orange No. 1; HC Red No. 1; 2-chloro-5-nitro-N-hydroxyethyl-p-phenylenediamine; HC Red No. 3; 4-amino-3-nitrophenol; 2-hydroxyethylamino-5-nitroanisole; 3-nitro-p-hydroxy ethyl aminophenol; 2-amino-3-nitrophenol; 6-nitro-o-toluidine; 3-methyl amino-4-nitrophenoxyethanol; 2-nitro-5-glycerylmethylaniline; HC Yellow No. 11; HC Violet No. 1; HC Orange No. 2; HC Orange No. 3; HC Yellow No. 9; 4-nitrophenyl aminoethylurea; HC Red No. 10; HC Red No. 11; 2-hydroxyethyl picramic acid; HC Blue No. 12; HC Yellow No. 6; hydroxyethyl-2-nitro-p-toluidine; HC Yellow No. 12; HC Blue No. 10; HC Yellow No. 7; HC Yellow No. 10; HC Blue No. 9; N-ethyl-3-nitro PABA; 4-amino-2-nitrophenyl-amine-2'-carboxylic acid; 2-chloro-6-ethylamino-4-nitrophenol; 6-nitro-2,5-pyridinediamine; HC Violet No. 2; 2-amino-6-chloro-4-nitrophenol; 4-hydroxypropylamino-3-nitrophenol; HC Yellow No. 13; 1,2,3,4-tetrahydro-6-nitrochinoxalin; HC Red No. 14; HC Yellow No. 15; HC Yellow No. 14; 3-amino-6-methylamino-2-nitropyridine; 2,6-diamino-3-((pyridine-3-yl)azo) pyridine; Basic Red No. 118; Basic Orange No. 69; N-(2-nitro-4-aminophenyl)-allylamine; 4-[(4-amino-3-methy 1phenyl)(4-imino-3-methyl-2,5-cyclohexadien-1-ylidene) methyl]-2-methyl-benzeneamine-hydrochloride; 2-[[4-(dimethyl-amino)phenyl]azo]-1,3-dimethyl-1H-imidazolium chloride; 1-methyl-4-[(methylphenyl-hydrazono)methyl]-pyridinium, methyl sulfate; 2-[(4-aminophenyl)azo]-1,3-dimethyl-1H-imidazolium chloride; Basic Red 22; Basic Red 76; Basic Brown 16; Basic Yellow 57; 7-(2',4'-dimethyl-5'-sulfophenylazo)-5-sulfo-8-hydroxynaphthalene; Acid Orange 7; Acid Red 33; 1-(3'-nitro-5'-sulfo-6'-oxophenylazo)-oxo-naphthalene chromium complex; Acid Yellow 23; Acid Blue 9; Basic Violet 14; Basic Blue 7; Basic Blue 26; sodium salt of mixture of mono- & disulfonic acids (mainly the latter) of quinophthalone or 2-quinolylindandione; Basic Red 2; Basic Blue 99; Disperse Red 15; Acid Violet 43; Disperse Violet 1; Acid Blue 62; Pigment Blue 15; Acid Black 132; Basic Yellow 29; Disperse Black 9; 1-(N-methylmorpholinium-propylamino)-4-hydroxy-anthraquinone methylsulfate; N,N-dimethyl-3-((4-(methylamino)-9,10-di oxo-9,10-dihydro anthracen-1-yl)amino)-N-propy 1propan-1-aminium bromide, HC Blue No. 8; HC Red No. 8; HC Green No. 1; HC Red No. 9; 2-hydroxy-1,4-naphthoquinone; Acid Blue 199; Acid Blue 25; Acid Red 4; Henna Red; Indigo; Cochenille; HC Blue No. 14; Disperse Blue 23; Disperse Blue 3; Disperse Blue 377; Basic Red 51; Basic Orange 31; Basic Yellow 87; and mixtures thereof. Preferred direct dyes include but are not limited to: Disperse Black 9; HC Yellow 2; HC Yellow 4; HC Yellow 15; 4-nitro-o-phenylenediamine; 2-amino-6-chloro-4-nitrophenol; HC Red 3; Disperse Violet 1; HC Blue 2; Disperse Blue 3; Disperse Blue 377; Basic Red 51; Basic Orange 31; Basic Yellow 87; and mixtures thereof.

Oxidizing Agent

The inventive compositions may comprise an oxidizing agent, present in an amount sufficient to bleach melanin pigment in hair and/or cause formation of dye chromophores from oxidative dye precursors (including developers and/or couplers when present). Inorganic peroxygen materials capable of yielding hydrogen peroxide in an aqueous medium are preferred and include but are not limited to: hydrogen peroxide; inorganic alkali metal peroxides (e.g. sodium periodate and sodium peroxide); organic peroxides (e.g. urea peroxide, melamine peroxide); inorganic perhydrate salt bleaching compounds (e.g. alkali metal salts of perborates, percarbonates, perphosphates, persilicates, and persulphates, preferably sodium salts thereof), which may be incorporated as monohydrates, tetrahydrates, etc.; alkali metal bromates; enzymes; and mixtures thereof. In one embodiment, the oxidizing agents of the present invention are selected from percarbonates (such as sodium percarbonate, ammonium percarbonate and potassium percarbonate); and persulphates (such as sodium persulphate, ammonium persulphate, and potassium persulphate). In another embodiment, the oxidizing agents of the present invention are selected from sodium percarbonate and ammonium persulfate.

pH Modifiers and Buffering Agents

The inventive compositions may comprise a pH modifier and/or buffering agent in an amount that is sufficiently effective to adjust the pH of the composition to fall within a range from about 3 to about 13, in some embodiments from about 8 to about 12, and even from about 8 to about 11. In some embodiments, the pH range for the carbonate ion source as described herein below is from 8.5 to 9.5, preferably from 8 to 9. Suitable pH modifiers and/or buffering agents for use herein include, but are not limited to: ammonia, alkanolamines such as monoethanolamine, diethanolamine, triethanolamine, monopropanolamine, dipropanolamine, tripropanolamine, tripropanolamine, 2-amino-2-methyl-1-propanol, and 2-amino-2-hydroxymethyl-1,3,-propandiol and guanidium salts, alkali metal and ammonium hydroxides and carbonates, preferably sodium hydroxide and ammonium carbonate, and acidulents such as inorganic and inorganic acids, e.g., phosphoric acid, acetic acid, ascorbic acid, citric acid or tartaric acid, hydrochloric acid, and mixtures thereof.

Carbonate Ion Source

The compositions of the present invention may further comprise in an embodiment at least one source of peroxymonocarbonate ions, preferably formed in situ from a source of hydrogen peroxide and a carbonate ion source. According to the present invention the compositions thus also may comprise at least a source of carbonate ions or carbamate ions or hydrocarbonate ions or any mixture thereof. Any source of these ions may be utilized. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and oxidizing agent. Suitable sources of carbonate ions, carbamate and hydrocarbonate ions include sodium hydrogen carbonate, potassium hydrogen carbonate, ammonium carbamate and mixtures thereof Radical Scavenger System The inventive compositions may comprise a radical scavenger, in a sufficient amount to reduce damage to the hair during an oxidative bleaching or coloring process. The radical scavenger is preferably selected such that it is not an identical species as the alkalizing agent. The radical scavenger is a species that can react with a carbonate radical to convert the carbonate radical by a series of fast reactions to a less reactive species. Suitable radical scavengers may be selected from the classes of alkanolamines, amino sugars, amino acids and mixtures thereof, and may include, but are not limited to: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, serine, tryptophan and potassium, sodium and ammonium salts of the above and mixtures thereof. Other suitable radical scavenger compounds include benzylamine, glutamic acid, imidazole, di-tert-butylhydroxytoluene, hydroquinone, catechol and mixtures thereof.

Chelants

The inventive composition may comprise chelants in an amount sufficient to reduce the amount of metals available to interact with formulation components, particularly oxidizing agents, more particularly peroxides. Suitable chelants for use herein include but are not limited to: diamine-N,N'-dipolyacid, monoamine monoamide-N,N'-dipolyacid, and N,N'-bis(2-hydroxybenzyl)ethylenediamine-N,N'-diacetic acid chelants (preferably EDDS (ethylenediaminedisuccinic acid)), carboxylic acids (preferably aminocarboxylic acids), phosphonic acids (preferably aminophosphonic acids) and polyphosphoric acids (in particular straight polyphosphoric acids), their salts and derivatives.

Foaming Agents

The inventive composition may be delivered in the form of a foam. Such an embodiment requires the use of a foaming agent, such as surfactants (e.g., anionic, non-ionic, cationic and amphoteric), proteins (e.g., enzymes), cellulosic materials, polymeric materials and mixtures thereof. Suitable polymeric materials include hydrophilic polymers, such as, agar-agar, polyvinyl alcohol, sodium alginate and sodium dodecyl sulphate-poly(ethylene oxide). A preferred polymeric material is a hydrophobically-modified alkali soluble emulsion polymer synthesized through an emulsion polymerization process from an acid/acrylate copolymer backbone and a monomer that connects the hydrophobic groups as side chains. An example of such a material is Aculyn™ 22, commercially available from Rohm Haas, which is synthesized from acrylic acid, acrylate esters and a steareth-20 methacrylate ester. Another preferred polymer is an anionic alkali-soluble polymer emulsion synthesized from acid and acrylate comonomers through emulsion polymerization. An example of such a material is Aculyn™ 33, commercially available from Rohm Haas. Other foaming agents include cetyl hydroxyethylcellulose, PEG 7M, hydroxypropyl methylcellulose, Carbomer and polyquaternium-55. Mixtures of these materials may be used.

As used herein "foam" means a hair colorant composition which after being passed through a manually-actuable, non-aerosol dispenser has a foam specific volume from about 6 to about 14 ml/g, such as about 7.5 ml/g to about 12 ml/g, or even from about 8 to about 10.5 ml/g.

Acceptable foam characteristics in hair colorant composition are exemplified by foam that holds its shape and stays in a consistent form. The minimum time for this is at least long enough to transfer from a user's hand to the desired location on the hair, e.g. the foam substantially maintains its shape for at least 15 seconds, for example at least 20, or at least 30 seconds. It could be longer if a quantity of foam, e.g. a bowl full by a hair dresser, is generated and spreading on the head only starts once the bowl full is readily made.

If foam collapses prematurely and becomes liquid-like (or some liquid is forming a puddle in the hand below the foam) any movement of the user's hand causes the foam to run, drip or otherwise move from the user's hand before the foam reaches the desired location and is considered undesirable.

The foam is suitable when formed when the composition is used with a manually-actable, non-aerosol dispenser where the composition is mixed with air such that the ratio of air to composition is from about 1:6 to about 1:15, from about 1:8 to about 1:12, or about 1:10.

A suitable manually-actuable, non-aerosol dispenser structure include the dimensions of the dip tube, dimensions of the air ingress into the mixing chamber, mixing chamber dimensions, including the ingress and egress orifices from the mixing chamber, dispensing channel dimensions, porous elements (such as screens or meshes) and dispensing head orifice.

Method of Making Shampoo Formulations

Any suitable method of making the shampoo of the present invention may be used. In one embodiment, undecyl-based surfactant is blended with the other components of the shampoo compositions, according to standard methods known in the art. The typical procedure used for a clarifying shampoo would be to combine the undecyl sulfate paste or undeceth sulfate paste or mixtures thereof with water, add the desired water soluble co-surfactant and finish the composition by the addition preservatives, pH control agents, perfume, and salts to obtain the target physical properties. If a water insoluble co-surfactant is desired the surfactant and water mixture can be heated to a suitable temperature to facilitate its incorporation. If a rheology modifier is desired it can be added to the surfactant mixture prior the finishing step.

In the case of conditioning shampoos, typically the surfactant paste is combined with the co-surfactant as above and diluted with water to a target level commensurate to achieving the final activity. Rheology modifiers can be added at this point followed by conditioning agents, e.g. sucrose polyesters, silicones or silicone emulsions or other oils, cationic polymers from polymer premixes, perfumes, pearlizing agents or opacifiers, perfumes, and preservatives. Appropriate mixing steps to insure homogeneity are used as needed. The product is finished by the addition of pH control agents, hydrotropes, and salts to the desired physical properties.

Method of Making Conditioner Formulations

The hair conditioners can be prepared by any conventional method well known in the art. They are suitably made as follows: deionized water is heated to 85° C. and cationic surfactants and high melting point fatty compounds are mixed in. If necessary, cationic surfactants and fatty alcohols can be pre-melted at 85° C. before addition to the water. The water is maintained at a temperature of about 85° C. until the components are homogenized, and no solids are observed. The mixture is then cooled to about 55° C. and maintained at this temperature, to form a gel matrix. Silicones, or a blend of silicones and a low viscosity fluid, or an aqueous dispersion of a silicone is added to the gel matrix. When included, poly alpha-olefin oils, polypropylene glycols, and/or polysorbates are also added to the gel matrix. When included, other additional components such as perfumes and preservatives are added with agitation. The gel matrix is maintained at about 50° C. during this time with constant stirring to assure homogenization. After it is homogenized, it is cooled to room temperature. A triblender and/or mill can be used in each step, if necessary to disperse the materials.

Compact Formulations

The present invention can also be used in a compact hair care formulation. A compact formula is a formula which delivers the same benefit to the consumer at a lower usage level. Compact formulations and methods of making compact formulations are described in US Application Publication No 2009/0221463A1.

Adjunct Materials

While not essential for the purposes of the present invention, the non-limiting list of adjuncts illustrated hereinafter are suitable for use in the instant compositions and may be desirably incorporated in certain embodiments of the invention, for example to assist or enhance performance, for treatment of the substrate to be cleaned, or to modify the aesthetics of the composition as is the case with perfumes, colorants, dyes or the like. It is understood that such adjuncts are in addition to the components that are supplied via Applicants' agglomerate/particle. The precise nature of these additional components, and levels of incorporation thereof, will depend on the physical form of the composition and the nature of the operation for which it is to be used. Suitable adjunct materials include, but are not limited to, polymers, for example cationic polymers, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

As stated, the adjunct ingredients are not essential to Applicants' cleaning and fabric care compositions. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. However, when one or more adjuncts is present, such one or more adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds, ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, B-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include manganese, iron and chromium. Suitable MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in U.S. Pat. No. 6,225,464.

Method of Use

In one aspect, a method of treating and/or cleaning a situs, is disclosed. Said method may comprise optionally washing and/or rinsing said situs; contacting said situs with any single or combination of compositions disclosed in the present specification; and optionally washing and/or rinsing said situs. Typically at least a portion of the situs is contacted with an embodiment of Applicants' composition, in neat form or diluted in a liquor, for example, a wash liquor. For purposes of the present invention, washing includes but is not limited to, scrubbing, and mechanical agitation. If the situs comprises a fabric it may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

In one aspect, a situs treated in accordance with such compositions, for example by the aforementioned method is disclosed.

Processes of Making

The compositions of the present invention can be formulated into any suitable form and prepared by any process chosen by the formulator, non-limiting examples of which are described in U.S. Pat. Nos. 5,879,584; 5,691,297; 5,574,005; 5,569,645; 5,565,422; 5,516,448; 5,489,392; 5,486,303 all of which are incorporated herein by reference.

In one aspect, a process of making a composition comprising combining an adjunct ingredient and, based on total composition weight, and from about 0.1% to about 50%, from about 0.2% to about 25%, from about 0.5% to about 10%, or even from about 0.75% to about 5% particles, each of said particles independently having a particle size of from about 2 microns to about 80 microns, from about 5 microns to about 50 microns or even from about 10 microns to about 30 microns, each particle comprising:
  a.) a core that comprises, based on total particle weight, from about 6% to about 95%, from about 11% to about 85%, or from about 50% to about 75%, of a benefit agent and from about 5% to about 94%, from about 15% to about 89%, or even from about 25% to about 50% of a partitioning modifier and/or density modifier; and
  b.) a shell that encapsulates said core, said shell comprising, based on total shell weight, from about 50% to about 100%, from about 70% to about 100% or even from about 80% to about 100% of a polyacrylate,
to form a consumer product, is disclosed.

In one aspect of said process, said particles may be contained in a slurry that is combined with said adjunct.

In one aspect of said process, said slurry may comprise one or more processing aids, selected from the group consisting of water, aggregate inhibiting materials such as divalent salts; particle suspending polymers such as xanthan gum, guar gum, caboxy methyl cellulose.

In one aspect of said process, said particles may be contained in an agglomerate that is combined with said adjunct.

In one aspect of said process, said agglomerate may comprise materials selected from the group consisting of silicas, citric acid, sodium carbonate, sodium sulfate, sodium chloride, and binders such as sodium silicates, modified celluloses, polyethylene glycols, polyacrylates, polyacrylic acids, zeolites and mixtures thereof.

In one aspect, a process of making a composition comprising combining an adjunct ingredient with a particle made by the process of:
  a) reacting a multifunctional acrylate monomer and/or multifunctional acrylate oligomer, in one aspect a multifunctional methacrylate monomer and/or multifunctional methacrylate oligomer, in a benefit agent comprising a partitioning modifier and/or density modifier with a
    composition comprising:
      i) an amine acrylate and/or methacrylate and a strong acid; or
      ii) a carboxylic acid acrylate and/or methacrylate monomer and a strong base; or
      iii) an amine acrylate and/or methacrylate monomer and a carboxylic acid acrylate and/or carboxylic acid methacrylate monomer
    to form a core composition,
  b) forming an emulsion comprising said core composition, a surfactant, in one aspect anionic, cationic or neutral surfactant, and water;
  c) curing said emulsion by applying a sufficient amount of thermal, UV, and/or electron beam energy to said emulsion to induce sufficient free-radical polymerization to form a particle having a core comprising said benefit agent and a shell comprising an acrylate, said shell encapsulating said benefit agent to form a consumer product is disclosed.

Any suitable method of making the shampoo of the present invention may be used. In one embodiment, undecyl-based surfactant is blended with the other components of the shampoo compositions, according to standard methods known in the art. The typical procedure used for a clarifying shampoo would be to combine the undecyl sulfate paste or undeceth sulfate paste or mixtures thereof with water, add the desired water soluble co-surfactant and finish the composition by the addition preservatives, pH control agents, perfume, and salts to obtain the target physical properties. If a water insoluble co-surfactant is desired the surfactant and water mixture can be heated to a suitable temperature to facilitate its incorporation. If a rheology modifier is desired it can be added to the surfactant mixture prior the finishing step.

In the case of conditioning shampoos, typically the surfactant paste is combined with the co-surfactant as above and diluted with water to a target level commensurate to achieving the final activity. Rheology modifiers can be added at this point followed by conditioning agents, e.g. sucrose polyesters, silicones or silicone emulsions or other oils, cationic polymers from polymer premixes, perfumes, pearlizing agents or opacifiers, perfumes, and preservatives. Appropriate mixing steps to insure homogeneity are used as needed. The product is finished by the addition of pH control agents, hydrotropes, and salts to the desired physical properties.

The hair conditioners can be prepared by any conventional method well known in the art. They are suitably made as follows: deionized water is heated to 85° C. and cationic surfactants and high melting point fatty compounds are mixed in. If necessary, cationic surfactants and fatty alcohols can be pre-melted at 85° C. before addition to the water. The water is maintained at a temperature of about 85° C. until the components are homogenized, and no solids are observed. The mixture is then cooled to about 55° C. and maintained at this temperature, to form a gel matrix. Silicones, or a blend of silicones and a low viscosity fluid, or an aqueous dispersion of a silicone are added to the gel matrix. When included, poly alpha-olefin oils, polypropylene glycols, and/or polysorbates are also added to the gel matrix. When included, other additional components such as perfumes and preservatives are added with agitation. The gel matrix is maintained at about 50° C. during this time with constant stirring to assure homogenization. After it is homogenized, it is cooled to room temperature. A triblender and/or mill can be used in each step, if necessary to disperse the materials.

Test Methods

It is understood that the test methods that are disclosed in the Test Methods Section of the present application should be used to determine the respective values of the parameters of Applicants' invention as such invention is described and claimed herein.

(1) C Log P

The "calculated log P" (C log P) is determined by the fragment approach of Hansch and Leo (cf., A. Leo, in Comprehensive Medicinal Chemistry, Vol. 4, C. Hansch, P. G. Sammens, J. B. Taylor, and C. A. Ramsden, Eds. P. 295, Pergamon Press, 1990, incorporated herein by reference). C log P values may be calculated by using the "C LOG P" program available from Daylight Chemical Information Systems Inc. of Irvine, California U.S.A..

(2) Boiling Point

Boiling point is measured by ASTM method D2887-04a, "Standard Test Method for Boiling Range Distribution of Petroleum Fractions by Gas Chromatography," ASTM International.

(3) Median Particle Size

Particle size is measured using an Accusizer 780A, made by Particle Sizing Systems, Santa Barbara CA The instrument is calibrated from 0 to 300μ using Duke particle size standards. Samples for particle size evaluation are prepared by diluting about 1 g of capsule slurry in about 5 g of de-ionized water and further diluting about 1 g of this solution in about 25 g of water.

About 1 g of the most dilute sample is added to the Accusizer and the testing initiated, using the autodilution feature. The Accusizer should be reading in excess of 9200 counts/second. If the counts are less than 9200 additional sample should be added. The accusizer will dilute the test sample until 9200 counts/second and initiate the evaluation. After 2 minutes of testing the Accusizer will display the results, including volume-weighted median size.

The broadness index can be calculated by determining the particle size at which 95% of the cumulative particle volume is exceeded (95% size), the particle size at which 5% of the cumulative particle volume is exceeded (5% size), and the median volume-weighted particle size (50% size–50% of the particle volume both above and below this size). Broadness Index (5)=((95% size)−(5% size)/50% size).

(4) Headspace Ratio (a) Obtain a fragrance free consumer product formulation (shampoo or leave-on conditioner).

(b) Obtain fragrance microcapsules whose water content has been adjusted to achieve a perfume content of 25 wt % in the aqueous slurry.

(c) Prepare Sample A by adding 2.0 grams of the fragrance microcapsule aqueous slurry to 95 grams of the fragrance free consumer product formulation. Then add 3.0 grams of deionized water to balance the formulation to 100 grams. Age this formulation for 1 week at 40 degrees Centigrade.

(d) Prepare Sample B by adding 0.50 grams of the neat fragrance to 95 grams of fragrance free consumer product formulation. Then add 4.5 grams of deionized water to balance the formulation to 100 grams. Age this formulation for 1 week at 40 degrees Centigrade.

The Headspace Ratio is defined as the headspace concentration of Sample A divided by the headspace concentration of Sample B, $$\frac{H_{Sample\_A}}{H_{Sample\_B}},$$

where $H_{Sample\_A}$ is the headspace concentration of a consumer product formulation Sample A, and $H_{Sample\_B}$ is the headspace concentration of a consumer product formulation Sample B.

Solid-Phase Micro-Extraction (SPME)-Gas Chromatography/Mass Spectrometry is used to measure the level of perfume raw materials in the headspace of products. 1.0 grams of the 1 week at 40 degrees Centigrade aged sample (shampoo or conditioner) are placed into a clean 20 ml headspace vial and allowed to equilibrate for at least 2 hours at room temperature.

The samples are then analyzed using the MPS2-SMPE-GC-MS analysis system (GC-02001-0153, MSD-02001-0154, MPS2-02001-0155).

Apparatus:
1. 20 ml headspace vial
2. Timer.
3. Gas Chromatograph (GC): Agilent model 6890 with a CIS-4 injector (Gerstel, Mulheim, Germany) and MPS-2 Autosampler and TDU. For SPME analysis, we used the split/splitless injector (not the CIS-4 injector).
4. GC column: J&W DB-5 MS, 30 M×0.25 mm ID, 1.0-m film thickness obtained from J&W Scientific of Folsom, California, USA.
5. Carrier gas, helium, 1.5 ml/min. flow rate.
6. The injector liner is a special SPME liner (0.75 mm ID) from Supelco.
7. The Detector is a model 5973 Mass Selective Detector obtained from Agilent Technologies, Inc., Wilmington, DE, USA having a source temperature of about 230° C., and a MS Quad temperature of about 150° C.

Analysis Procedure:
1. Transfer sample to proper sample tray and proceed with SPME-GC-MS analysis.
2. Start sequence of sample loading and analysis. In this step, the sample is allowed to equilibrate for at least two hours on the auto sampler tray, then sampled directly from the tray. The SPME fiber assembly is DVB/CAR/PDMS (50/30 um, 24 ga, 1 cm length). Sampling time is 5 minutes.
3. Injector temperature is at 260 C.
4. Then GC-MS analysis run is started. Desportion time is 5 minutes.
5. The following temperature program is used:
   i) an initial temperature of about 50° C. which is held for 3 minutes,
   ii) increase the initial temperature at a rate of about 6° C./min until a temperature of about 250° C. is reached, then 25° C./min to 275° C., hold at about 275° C. for 4.67 minute.

6. Perfume compounds are identified using the MS spectral libraries of John Wiley & Sons and the National Institute of Standards and Technology (NIST), purchased and licensed through Hewlett Packard.
7. Chromatographic peaks for specific ions are integrated using the Chemstation software obtained from Agilent Technologies, Inc., Wilmington, DE, USA..
8. The ratio for each PRM is calculated by dividing the peak area for the perfume raw material in Sample A by the peak area in Sample B.
9. Each ratio is then weighted by that perfume raw material's weight composition in the perfume.
10. The Headspace Ratio is calculated as the sum of the individual perfume raw material ratios obtained in step 9.

(5) Odor Detection Threshold (ODT) is determined using a gas chromatograph. The gas chromatograph is calibrated to determine the exact volume of material injected by the syringe, the precise split ratio, and the hydrocarbon response using a hydrocarbon standard of known concentration and chain length distribution. The air flow rate is accurately measured and, assuming the duration of human inhalation to last 12 seconds, the sampled volume is calculated. Since the precise concentration at the detector at any point in time is known, the mass per volume inhaled is known, and hence the concentration of material. For example, to determine whether a material has a threshold below 50 parts per bullion, solutions are delivered to the sniff port at the calculated concentration. A panelist sniffs the GC effluent and identifies the retention time when odor is noticed. The average among 6 panelists determines the threshold of noticeability. The necessary amount of analyte is injected into the column to achieve a 50 parts per billion concentration at the detector. Typical gas chromatograph parameters for determining odor detection thresholds are listed below:

GC: 5890 Series II with FID detector, 7673 Autosampler
Column: J&W Scientific DB-1
Length: 30 meters, 0.25millimeter inside diameter, 1 micrometer film thickness
Method:
split injection: 17/1 split ratio
Autosampler: 1.13 microliters per injection
Column flow: 1.10 milliLiters per minute
Air Flow: 345 milliLiters per minute
Inlet Temperature: 245 degrees Centigrade
Detector Temperature: 285 degrees Centigrade
Initial Temperature=50 degrees Centigrade, 5 degrees Centigrade per minute ramp rate, final temperature=280 degrees Centigrade, Final time=6 minutes
Leading assumptions: 12 seconds per sniff, GC air adds to sample dilution (6) Olfactive Analysis of Leave-on-Treatment Product
a) 0.16 milliliters of Leave-on-Conditioner product is applied to a hair switch (IHI, 4 grams, 8 inches long, moderately damaged grade) that has been combed, wet, and lightly squeegeed. Lather switch 50-60 strokes (30 seconds) in a milking action.
b) Leave hair to dry at ambient temperature by hanging it on a rack. After approximately 3 hours, olfactively grade the hair switch according to the Primavera Grade (O-100 scale for intensity, where a 10 point difference is consumer noticeable). Record this as the Initial Pre-Comb fragrance intensity.
c) Comb the hair switch 3 times and olfactively grade, record this as the Initial Post-Comb fragrance intensity.
d) Leave the hair switch under ambient conditions (70 degrees Fahrenheit and 30% relative humidity) for 24 hours. Then, olfactively grade the hair switch according to the Primavera Grade (O-100 scale for intensity, where a 10 point difference is consumer noticeable), record this as the 24 hr aged Pre-Comb olfactive intensity. Comb the hair switch 3 times and assign an olfactive grade, record this as the 24 hr aged Post-Comb olfactive intensity.

(7) Olfactive Analysis of Shampoo Product
a. 0.4 milliliters of Shampoo product is applied to a hair switch (IHI, 4 grams, 8 inches long, moderately damaged grade) that has been combed, wet, and lightly squeegeed. Lather switch 50-60 strokes (30 seconds) in a milking action.
b. Rinse with stationary shower rinse with no manipulation of hair (100 degrees Fahrenheit water temperature, water flow at 1.5 gallons per minute, for 30 seconds, water hardness of 8 grains per gallon). Lightly squeegee once down the hair switch from top to bottom between fingers after rinsing to remove excess water.
c. Repeat application of product per step (a), milking, rinsing, and squeegeeing per step (b).
d. Leave hair to dry at ambient temperature by hanging it on a rack. After approximately 3 hours, olfactively grade the hair switch according to the Primavera Grade (O-100 scale for intensity, where a 10 point difference is consumer noticeable). Record this as the Initial Pre-Comb fragrance intensity.
e. Comb the hair switch 3 times and olfactively grade, record this as the Initial Post-Comb fragrance intensity.
f. Leave the hair switch under ambient conditions (70 degrees Fahrenheit and 30% relative humidity) for 24 hours. Then, olfactively grade the hair switch according to the Primavera Grade (O-100 scale for intensity, where a 10 point difference is consumer noticeable), record this as the 24 hr aged Pre-Comb olfactive intensity. Comb the hair switch 3 times and assign an olfactive grade, record this as the 24 hr aged Post-Comb olfactive intensity.

8. Fracture Strength Test Method
a.) Place 1 gram of particles in 1 liter of distilled deionized (DI) water.
b.) Permit the particles to remain in the DI water for 10 minutes and then recover the particles by filtration, using a 60 mL syringe filter, 1.2 micron nitrocellulose filter (Millipore, 25 mm diameter).
c.) Determine the rupture force of 50 individual particles. The rupture force of a particle is determined using the procedure given in Zhang, Z.; Sun, G; "Mechanical Properties of Melamine-Formaldehyde microcapsules," J. Microencapsulation, vol 18, no. 5, pages 593-602, 2001. Then calculate the fracture strength of each particle by dividing the rupture force (in Newtons) by the cross-sectional area of the respective spherical particle ($\pi r^2$, where r is the radius of the particle before compression), said cross-sectional area being determined as follows: measuring the particle size of each individual particle using the experimental apparatus and method of Zhang, Z.; Sun, G; "Mechanical Properties of Melamine-Formaldehyde microcapsules," J. Microencapsulation, vol 18, no. 5, pages 593-602, 2001.
d.) Use the 50 independent measurements from c.) above, and calculate the percentage of particles having a fracture strength within the claimed range fracture strength range.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

A perfume composition, called Scent A, is utilized to prepare the examples of the invention. The table below lists the ingredients, and their properties. Table 2 provides the C log P breakdown of the perfume oil composition.

TABLE 1

| Material Name | ClogP | Boiling Point ° C. |
|---|---|---|
| Beta Gamma Hexenol | 1.3 | 155 |
| Phenyl Ethyl Alcohol | 1.32 | 219 |
| Helional | 1.77 | 329 |
| Triplal Extra | 1.78 | 199 |
| Amyl- Acetate (isomer Blends) | 1.87 | 135 |
| Melonal | 2.09 | 182 |
| Liffarome | 2.14 | 167 |
| Iso Eugenol Acetate | 2.17 | 303 |
| Cis 3 Hexenyl Acetate | 2.18 | 167 |
| Jasmolactone | 2.36 | 219 |
| 2` 6-nonadien-1-ol | 2.43 | 213 |
| Florosa | 2.46 | 238 |
| Nonalactone | 2.66 | 193 |
| Cis Jasmone | 2.81 | 254 |
| Ethyl Linalool | 2.92 | 223 |
| Pino Acetaldehyde | 2.98 | 261 |
| Methyl Dihydro Jasmonate | 3.01 | 323 |
| Undecavertol | 3.06 | 242 |
| Azurone 10/tec 0015573 | 3.06 | 395 |
| Dihydro Myrcenol | 3.08 | 195 |
| Cyclemax | 3.23 | 281 |
| Hivernal | 3.29 | 351 |
| Pomarose | 3.51 | 214 |
| Undecalactone | 3.75 | 228 |
| Damascenone Total 937459 | 3.89 | 267 |
| Acalea (01-1963) | 3.9 | 344 |
| Cis-3-hexenyl Salicylate | 4 | 316 |
| Ionone Beta | 4.02 | 267 |
| Polysantol | 4.21 | 256 |
| Ambroxan | 4.58 | 285 |
| 5-cyclohexadecen-1-one | 5.04 | 331 |
| Iso E Super Or Wood | 5.05 | 325 |
| Laevo Muscone | 5.48 | 321 |
| Helvetolide 947650 | 5.56 | 309 |

TABLE 2

| Clog P Range | wt % of Formula |
|---|---|
| 0.1-1.5 | 2.0% |
| 1.5-2.5 | 16.3% |
| 2.5-3.5 | 38.8% |
| 3.5-4.5 | 19.3% |
| >4.5 | 23.6% |

Example 1: 90 wt % Core/10 wt % Wall, Scent A Fragrance Oil

The following general procedure is used to prepare microcapsules using the materials and methods detailed in Examples 2 through 17.

An oil solution, consisting of 150 g Fragrance Oil, 0.6 g DuPont Vazo-52, and 0.4 g DuPont Vazo-67, is added to a 35° C. temperature controlled steel jacketed reactor, with mixing at 1000 rpm (4 tip, 2" diameter, flat mill blade) and a nitrogen blanket applied at 100 cc/min. The oil solution is heated to 75° C. in 45 minutes, held at 75° C. for 45 minutes, and cooled to 60° C. in 75 minutes.

A second oil solution, consisting of 37.5 g Fragrance Oil, 0.5 g tertiarybutylaminoethyl methacrylate, 0.4 g 2-carboxyethyl acrylate, and 19.5 g Sartomer CN975 (hexafunctional aromatic urethane-acrylate oligomer) is added when the first oil solution reached 60° C. The combined oils are held at 60° C. for an additional 10 minutes.

Mixing is stopped and a water solution, consisting of 112 g 5% Celvol 540 polyvinyl alcohol, 200 g water, 1.1 g 20% NaOH, and 1.17 g DuPont Vazo-68WSP, is added to the bottom of the oil solution, using a funnel.

Mixing is again started, at 2500 rpm, for 60 minutes to emulsify the oil phase into the water solution. After milling is completed, mixing is continued with a 3" propeller at 350 rpm. The batch is held at 60° C. for 45 minutes, the temperature is increased to 75° C. in 30 minutes, held at 75° C. for 4 hours, heated to 90° C. in 30 minutes and held at 90° C. for 8 hours. The batch is then allowed to cool to room temperature.

The finished microcapsules have a median particle size of 7 microns, and a broadness index of 1.3.

Example 2-8. 90 wt % Core, 10 wt % Wall, (Scent A with Various Amounts of IPM: 10%, 20%, 30%, 40%, 50%, 60%, 87%)

Examples 2-8 are prepared by the same procedure as in Example 1 except that the Fragrance Oil is formulated with Scent A and Isopropyl Myristate prior to preparation of first and second oil solutions. The table below provides the total mass of fragrance oil by its components—Scent A fragrance and isopropyl myristate partitioning modifier, along with the properties of the microcapsules.

| Example | Mass of Scent A in Fragrance Oil | Mass of Isopropyl Myristate in Fragrance Oil | Median Particle Size (microns) | Broadness Index |
|---|---|---|---|---|
| 1 | 187.5 | 0 | 7 | 1.3 |
| 2 | 168.75 | 18.75 | 8.58 | 1.32 |
| 3 | 150.00 | 37.50 | 9.72 | 1.25 |
| 4 | 131.25 | 56.25 | 7.11 | 1.63 |
| 5 | 112.50 | 75.00 | 10.01 | 1.29 |
| 6 | 93.75 | 93.75 | 10.88 | 1.18 |
| 7 | 75.00 | 112.50 | 9.97 | 1.42 |
| 8 | 24.38 | 163.13 | 10.74 | 1.30 |

Example 9. 90 wt % Core, 10 wt % Wall, (Scent A+20% Castor Oil)

Example 9 is prepared by the same procedure as Example 1 except that 20% of Fragrance oil in the first and second oil solutions is replaced by the same quantity of Castor Oil (obtained from J. T. Baker of Phillipsburg, New Jersey, USA)

| Example | Mass of Scent A in Fragrance Oil | Mass of Castor Oil in Fragrance Oil | Median Particle Size (microns) | Broadness Index |
|---|---|---|---|---|
| 9 | 150.00 | 37.5 | 12.02 | 1.30 |

Example 10. 90 wt % Core, 10 wt % Wall, (Scent A+20% Triethyl Citrate)

Example 10 is prepared by the same procedure as Example 1 except that 20% of Fragrance oil in the first and second oil solutions is replaced by the same quantity of Triethyl Citrate (obtained from Sigma Aldrich of Milwaukee, Wisconsin, USA)

| Example | Mass of Scent A in Fragrance Oil | Mass of Triethyl Citrate in Fragrance Oil | Median Particle Size (microns) | Broadness Index |
|---|---|---|---|---|
| 10 | 150 | 37.5 | 8.06 | 1.38 |

Example 11. 90 wt % Core, 10 wt % Wall, (Scent A+20% Paraffin Oil)

Example 11 is prepared by the same procedure as Example 1 except that 20% of Fragrance oil in the first and second oil solutions is replaced by the same quantity of Paraffin Oil (Isopar L obtained from Exxon Mobil Chemical Company of Houston, Texas, USA)

| Example | Mass of Scent A in Fragrance Oil | Mass of Paraffin Oil in Fragrance Oil | Median Particle Size (microns) | Broadness Index |
|---|---|---|---|---|
| 11 | 150 | 37.5 | 11.29 | 1.14 |

Example 12. 90 wt % Core, 10 wt % Wall, (Scent A+20% Mineral Oil)

Example 12 is prepared by the same procedure as Example 1 except that 20% of Fragrance oil in the first and second oil solutions is replaced by the same quantity of Mineral Oil (obtained from Fisher Scientific Company of Fairlawn, New Jersey, USA)

| Example | Mass of Scent A in Fragrance Oil | Mass of Mineral Oil in Fragrance Oil | Median Particle Size (microns) | Broadness Index |
|---|---|---|---|---|
| 12 | 150 | 37.5 | 11.43 | 1.21 |

Example 13. 90 wt % Core, 10 wt % Wall, (Scent A+20% IPM) ANIONIC

Example 13 is prepared by the same procedure as Example 3 except the water phase solution consisted of 22.5 g of a 25% solution of polyacrylic acid/butyl acrylate copolymer, 325 g water, 1.1 g 20% NaOH, and 1.17 g DuPont Vazo-68WSP.

| Example | Mass of Scent A in Fragrance Oil | Mass of Isopropyl Myristate in Fragrance Oil | Median Particle Size (microns) | Broadness Index |
|---|---|---|---|---|
| 13 | 150 | 37.5 | 7.02 | 1.53 |

Example 14. 90 wt % Core, 10 wt % Wall, (Scent A+20% IPM) CATIONIC

Example 14 is prepared by the same procedure as Example 3 except the water phase solution consisted of 11.2 g of a 50% solution of Poly(dimethylamine-co-epichlorohydrin-co-ethylenediamine) terpolymer, 350 g water, 2.8 g 20% NaOH, and 1.17 g DuPont Vazo-68WSP.

| Example | Mass of Scent A in Fragrance Oil | Mass of Isopropyl Myristate in Fragrance Oil | Median Particle Size (microns) | Broadness Index |
|---|---|---|---|---|
| 14 | 150 | 37.5 | 10.48 | 1.30 |

Example 15. 90 wt % Core, 10 wt % Wall, (Scent A+20% IPM) 5 Micron

Example 15 is prepared by the same procedure as Example 3, but milling conditions adjusted to achieve a 5 micron final capsule size.

| Example | Mass of Scent A in Fragrance Oil | Mass of Isopropyl Myristate in Fragrance Oil | Median Particle Size (microns) | Broadness Index |
|---|---|---|---|---|
| 15 | 150 | 37.5 | 5.71 | 1.54 |

Example 16. 90 wt % Core, 10 wt % Wall, (Scent A+20% IPM) 30 Micron

Example 16 is prepared by the same procedure as Example 3, but milling conditions adjusted to achieve a 30 micron final capsule size.

| Example | Mass of Scent A in Fragrance Oil | Mass of Isopropyl Myristate in Fragrance Oil | Median Particle Size (microns) | Broadness Index |
|---|---|---|---|---|
| 16 | 150 | 37.5 | 27.70 | 1.33 |

Example 17. 90 wt % Core, 10 wt % Wall, (Scent A+20% IPM) 50 Micron

Example 17 is prepared by the same procedure as Example 3, but milling conditions adjusted to achieve a 50 micron final capsule size.

| Example | Mass of Scent A in Fragrance Oil | Mass of Isopropyl Myristate in Fragrance Oil | Median Particle Size (microns) | Broadness Index |
|---|---|---|---|---|
| 17 | 150 | 37.5 | 56.60 | 1.05 |

| Ingredient | Wt. % |
|---|---|
| Water | 86.14% |
| Cetyl Alcohol | 3.46% |
| Steary Alcohol | 6.44% |
| Sodium laureth-3 sulfate (28% Active) | 3.93% |
| 5-Chloro-2-methyl-4-isothiazolin-3-one, Kathon CG | 0.03% |

Example 18. Polyurea/Urethane Capsules

An aqueous solution, consisting of 6.06 g Celvol 523 polyvinyl alcohol (Celanese Chemicals) and 193.94 g deionized water, is added into a temperature controlled steel jacketed reactor at room temperature. Then an oil solution, consisting of 75 g Scent A and 25 g Desmodur N3400 (polymeric hexamethylene diisocyanate), is added into the reactor. The mixture is emulsified with a propeller (4 tip, 2" diameter, flat mill blade; 2200 rpm) to desired emulsion droplet size. The resulting emulsion is then mixed with a Z-bar propeller at 450 rpm. An aqueous solution, consisting of 47 g water and 2.68 g tetraethylenepentamine, is added into the emulsion. And it is then heated to 60° C., held at 60° C. for 8 hours, and allowed to cool to room temperature. The median particle size of the formed microcapsules is 10 microns, with a broadness index of 1.5

Example 19. Polyurea/Urethane Capsules

Prepare the Oil Phase by adding 4.44 grams of isophorone diisocyanate (Sigma Aldrich) to 5.69 grams of Scent A fragrance oil. Prepare a Water Phase by mixing 1.67 grams of Ethylene Diamine (Sigma Aldrich) and 0.04 grams of 1,4-Diazabicyclo[2.2.2]octane (Sigma Aldrich) into 40 grams of a 5 wt % aqueous solution of Polyvinylpyrrolidone K-90 (Sigma Aldrich) at 10 degrees Centigrade. Next, add the Oil Phase contents to 15.0 grams of a 5 wt % aqueous solution of Polyvinylpyrrolidone K-90 (Sigma Aldrich), while agitating the mix at 1400 RPM using a Janke & Kunkel IKA Laboretechnik RW20 DZM motor with a 3-blade turbine agitator for approximately 9 minutes. Next, add the addition of the Water Phase into the emulsified Oil Phase dropwise over a 6.5 minute period, while continuing to agitate at 1400 RPM. Continue to agitate for 23 minutes, then reduce the agitation speed to 1000 RPM. After 3.75 additional hours, reduce the agitation speed to 500 RPM, and continue to agitate for 14 hours. Start heating the dispersion to 50 degrees Centigrade, over a 2 hour period. Age the capsules at 50 C for 2 hours, then collect the formed microcapsules. The resulting polyurea/urethane particles have a median particle size of 12 microns and a broadness index of 1.5

Example 20. Polyurea/Urethane Capsules

The same procedure as outlined in Example 18 is followed, except that the Fragrance Oil comprises 80 wt % Scent A and 20 wt % Isopropyl Myristate. The formed microcapsules have a median particle size of 11 microns, and a broadness index of 1.5

Example 21. Spray Drying of Perfume Microcapsules

The perfume microcapsule slurry of Example 2 is pumped at a rate of 1 kg/hr into a co-current spray dryer (Niro Production Minor, 1.2 meter diameter) and atomized using a centrifugal wheel (100 mm diameter) rotating at 18,000 RPM. Dryer operating conditions are: air flow of 80 kg/hr, an inlet air temperature of 200 degrees Centigrade, an outlet temperature of 100 degrees Centigrade, dryer operating at a pressure of −150 millimeters of water vacuum. The dried powder is collected at the bottom of a cyclone. The collected particles have an approximate particle diameter of 11 microns. The equipment used the spray drying process may be obtained from the following suppliers: IKA Werke GmbH & Co. KG, Janke and Kunkel—Str. 10, D79219 Staufen, Germany; Niro A/S Gladsaxevej 305, P.O. Box 45, 2860 Soeborg, Denmark and Watson-Marlow Bredel Pumps Limited, Falmouth, Cornwall, TR11 4RU, England.

Example 22. Microcapsules in Leave-On-Conditioner

Each of the capsules from the above examples is formulated into a leave-on-conditioner formulation as follows: to 98.0 grams of leave-on-conditioner (with a typical formulation given below) is added an appropriate amount of microcapsule slurry of examples 1 through 20 to deliver a Scent A fragrance usage level of 0.5 wt %. The microcapsules are added on top of the conditioner formulation, then the contents are mixed using a SpeedMixer by Hauschild DAC 400FVZ, at 1000 RPM for 1 minute.

A portion of this product is weighed in 20 mL vials, and placed into a constant temperature environment for ageing (1 week at 40 degrees Centigrade).

A portion of this product is used to treat hair switches for in-vitro testing, using the Olfactive Analysis of Leave-On-Treatment test method. The following results are obtained.

| Example | Level of partitioning modifier | % Scent A Fragrance in Capsule Slurry | Quantity of Leave on Conditioner Product (g) | Quantity of Fragrance Delivery Technology (g) | Quantity of Water (g) | Olfactive Performance - Initial Pre-Comb/Post-Comb | Olfactive Performance - 24 hr Aged Pre-Comb/Post-Comb |
|---|---|---|---|---|---|---|---|
| Neat Perfume | 0% | N/A | 98.00 | 0.50 | 1.50 | 35/40 | 25/30 |
| 1 | 0% | 32% | 98.00 | 1.58 | 0.42 | 40/40 | 20/20 |
| 2 | 10% | 44.71% | 98.00 | 1.12 | 0.88 | 40/75 | 40/75 |
| 3 | 20% | 39.93% | 98.00 | 1.25 | 0.75 | 40/70 | 40/75 |
| 4 | 30% | 28.85% | 98.00 | 1.73 | 0.27 | 35/70 | 40/70 |
| 5 | 40% | 30.67% | 98.00 | 1.63 | 0.37 | 40/75 | 40/75 |
| 6 | 50% | 23.06% | 98.00 | 2.17 | 0.00 | 40/70 | 40/60 |
| 7 | 60% | 15.48% | 98.00 | 3.23 | 0.00 | 40/70 | 40/50 |
| 8 | 87% | 5.93% | 98.00 | 8.43 | 0.00 | 40/70 | 30/65 |
| 9 | 20% | 34.40% | 98.00 | 1.45 | 0.55 | 35/65 | 30/60 |
| 10 | 20% | 32.00% | 98.00 | 1.56 | 0.44 | 35/40 | 35/40 |
| 11 | 20% | 33.57% | 98.00 | 1.49 | 0.51 | 35/70 | 40/75 |
| 12 | 20% | 31.38% | 98.00 | 1.59 | 0.41 | 35/70 | 40/65 |
| 13 | 20% | 34.41% | 98.00 | 1.45 | 0.55 | 40/75 | 40/75 |
| 14 | 20% | 33.74% | 98.00 | 1.48 | 0.52 | 40/65 | 40/65 |
| 15 | 20% | 24.39% | 98.00 | 2.05 | 0.00 | 55/80 | 30/75 |
| 16 | 20% | 28.01% | 98.00 | 1.79 | 0.21 | 45/80 | 20/40 |

| Example | Level of partitioning modifier | % Scent A Fragrance in Capsule Slurry | Quantity of Leave on Conditioner Product (g) | Quantity of Fragrance Delivery Technology (g) | Quantity of Water (g) | Olfactive Performance - Initial Pre-Comb/Post-Comb | Olfactive Performance - 24 hr Aged Pre-Comb/Post-Comb |
|---|---|---|---|---|---|---|---|
| 17 | 20% | 24.06% | 98.00 | 2.08 | 0.00 | 40/45 | 20/35 |
| 18 | 0% | 22.50% | 98.00 | 2.22 | 0.00 | 40/40 | 20/30 |
| 19 | 0% | 11.00% | 98.00 | 4.55 | 0.00 | 45/55 | 20/25 |
| 20 | 20% | 27.05% | 98.00 | 1.85 | 0.15 | 45/45 | 20/25 |

A 10 point increase in the olfactive grade is a noticeable change in odor intensity. Pre-comb refers to the olfactive intensity of Scent A on dry hair; post-comb refers to the olfactive intensity of Scent A on dry hair after combing the hair switch 3 times. Note the significant increase in post-comb odor intensity with the Acrylate capsules of example 2-9 and 11-15 for initial hair odor and 24 hr aged hair odor. One can see the dramatic change in odor intensity upon combing, when compared to the pre-comb at the time point, and when compared to the neat perfume control. The partitioning modifier type and level, and the median particle size play a critical role in driving the fragrance benefit. The polyurea/urethane capsules do not deliver the desired olfactive performance profile.

The Headspace Ratio of these products is also measured, and is tabulated below.

| Example | Headspace Ratio -LOT |
|---|---|
| Neat Perfume | 1.00 |
| 1 | 1.00 |
| 2 | 0.79 |
| 3 | 0.78 |
| 4 | 0.58 |
| 5 | 0.35 |
| 6 | 0.28 |
| 7 | 0.23 |
| 8 | 0.20 |
| 9 | 0.83 |
| 10 | 0.95 |
| 11 | 0.64 |
| 12 | 0.77 |
| 13 | 0.73 |
| 14 | 0.79 |
| 15 | 0.72 |
| 16 | 0.64 |
| 17 | 0.59 |
| 18 | 0.44 |
| 19 | 0.68 |
| 20 | not available |

A typical composition of a leave-on conditioner formulation is given in the following table:

| Components | Ex. II (LOT) (%) |
|---|---|
| Premix | |
| Aminosilicone | — |
| PDMS | 1.0-1.5 |
| Gel matrix carrier | |
| Behenyl trimethyl ammonium chloride | — |
| Stearamidopropyldimethylamine (SAPDMA), C18 | 0.60-0.8 |
| DTDMAC, C18(Quaternium-18) | 0.45-0.6 |
| Citric Acid (anhydrous) | 0.10-0.25 |
| Cetyl alcohol | 0.80-1.0 |
| Stearyl alcohol | 0.54-1.0 |
| Deionized Water | Balance |
| Polymers | |
| Hydroxyethylcellulose (HEC) | 0.15-0.50 |
| PEG-2M (Polyox WAR N-10) | 0.30-0.60 |
| Others | |
| Perfume microcapsules | 0.10-1.20 |
| Preservatives | 0.40-0.60 |

Example 23. Microcapsules in Shampoo

A subset of the capsules from the above examples is formulated into a rinse-off Shampoo formulation as follows: to 90.0 grams of shampoo formulation (with a typical formulation given below) is added an appropriate amount of microcapsule slurry of examples 15 through 20 to deliver a Scent A fragrance usage level of 0.5 wt %. The microcapsules and water are added on top of the shampoo formulation, then the contents are mixed using a SpeedMixer by Hauschild DAC 400FVZ mixer, at 1850 RPM for 1 minute.

A portion of this product is weighed in 20 mL vials, and placed into a constant temperature environment for ageing (1 week at 40 degrees Centigrade).

A portion of this product is used to treat hair switches for in-vitro testing, using the Olfactive Analysis of Shampoo test method. The following results are obtained.

| Example | Level of partitioning modifier | % Scent A Fragrance in Capsule Slurry | Quantity of Shampoo Product (g) | Quantity of Fragrance Delivery Technology (g) | Quantity of Water (g) | Olfactive Performance - Initial Pre-Comb/Post-Comb | Olfactive Performance - 24 hr Aged Pre-Comb/Post-Comb |
|---|---|---|---|---|---|---|---|
| Neat Perfume | 0% | N/A | 90.00 | 0.50 | 9.50 | 5/20 | 5/10 |
| 15 | 20% | 24.39% | 90.00 | 2.05 | 7.95 | 5/25 | 5/25 |
| 16 | 20% | 28.01% | 90.00 | 1.79 | 8.21 | 5/10 | 5/5 |
| 17 | 20% | 24.06% | 90.00 | 2.08 | 7.92 | 5/10 | 5/10 |

| Example | Level of partitioning modifier | % Scent A Fragrance in Capsule Slurry | Quantity of Shampoo Product (g) | Quantity of Fragrance Delivery Technology (g) | Quantity of Water (g) | Olfactive Performance - Initial Pre-Comb/Post-Comb | Olfactive Performance - 24 hr Aged Pre-Comb/Post-Comb |
|---|---|---|---|---|---|---|---|
| 18 | 0% | 22.50% | 90.00 | 2.22 | 7.78 | 20/20 | 5/5 |
| 19 | 0% | 11.00% | 90.00 | 4.55 | 5.45 | 5/20 | 5/5 |
| 20 | 20% | 27.05% | 90.00 | 1.85 | 8.15 | 5/15 | 5/5 |

Note that the olfactive results are much lower in the case of shampoo, primarily due to poor retention of capsules on hair during the rinse-off process. However, particle size seems to play an important role in improving retention and driving a sustained fragrance odor performance upon combing (initially and after 24 hour ageing of hair)—compare Example 15 with the Neat Perfume control.

The Headspace Ratio is also measured for the above samples, and is tabulated below.

| Example | Headspace Ratio |
|---|---|
| 15 | 0.86 |
| 16 | 0.80 |
| 17 | 0.76 |
| 18 | 0.24 |
| 19 | 0.77 |
| 20 | Not Measured |

Typical composition of shampoo formulations are given in the examples below.

| | EXAMPLE COMPOSITION | | |
|---|---|---|---|
| Ingredient | I | II | III |
| Water | q.s. | q.s. | q.s. |
| Polyquaternium 76[1] | 2.50 | — | — |
| Guar, Hydroxylpropyl Trimonium Chloride[2] | — | 0.25 | — |
| Polyquaterium 6[3] | — | — | 0.79 |
| Sodium Laureth Sulfate (SLE3S)[4] | 21.43 | 21.43 | 21.43 |
| Sodium Lauryl Sulfate (SLS)[5] | 20.69 | 20.69 | 20.69 |
| Silicone[6] | 0.75 | 1.00 | 0.5 |
| Cocoamidopropyl Betaine[7] | 3.33 | 3.33 | 3.33 |
| Cocoamide MEA[8] | 1.0 | 1.0 | 1.0 |
| Ethylene Glycol Distearate[9] | 1.50 | 1.50 | 1.50 |
| Sodium Chloride[10] | 0.25 | 0.25 | 0.25 |
| Fragrance | 0.70 | 0.70 | 0.70 |
| Fragrance Microcapsule of Example 3 | 1.2 | 1.2 | 1.2 |
| Preservatives, pH adjusters | Up to 1% | Up to 1% | Up to 1% |

[1]Mirapol AT-1, Copolymer of Acrylamide(AM) and TRIQUAT, MW = 1,000,000; CD = 1.6 meq./gram; 10% active; Supplier Rhodia
[2]Jaguar C500, MW-500,000, CD = 0.7, supplier Rhodia
[3]Mirapol 100S, 31.5% active, supplier Rhodia
[4]Sodium Laureth Sulfate, 28% active, supplier: P&G
[5]Sodium Lauryl Sulfate, 29% active supplier: P&G
[6]Glycidol Silicone VC2231-193C
[7]Tegobetaine F-B, 30% active supplier: Goldschmidt Chemicals
[8]Monamid CMA, 85% active supplier Goldschmidt Chemical
[9]Ethylene Glycol Distearate, EGDS Pure, supplier Goldschmidt Chemical
[10]Sodium Chloride USP (food grade), supplier Morton; note that salt is an adjustable ingredient, higher or lower levels may be added to achieve target viscosity.

| | EXAMPLE COMPOSITION | | |
|---|---|---|---|
| Ingredient | IV | V | VI |
| Water | q.s. | q.s. | q.s. |
| Silicone A [1] | 1.0 | — | — |
| Silicone B [2] | — | 0.5 | — |
| Silicone C [3] | — | — | 0.5 |
| Cyclopentasiloxane [4] | — | 0.61 | 1.5 |
| Behenyl trimethyl ammonium chloride [5] | 2.25 | 2.25 | 2.25 |
| Isopropyl alcohol | 0.60 | 0.60 | 0.60 |
| Cetyl alcohol [6] | 1.86 | 1.86 | 1.86 |
| Stearyl alcohol [7] | 4.64 | 4.64 | 4.64 |
| Disodium EDTA | 0.13 | 0.13 | 0.13 |
| NaOH | 0.01 | 0.01 | 0.01 |
| Benzyl alcohol | 0.40 | 0.40 | 0.40 |
| Methylchloroisothiazolinone/Methylisothiazolinone [8] | 0.0005 | 0.0005 | 0.0005 |
| Panthenol [9] | 0.10 | 0.10 | 0.10 |
| Panthenyl ethyl ether [10] | 0.05 | 0.05 | 0.05 |
| Fragrance | 0.35 | 0.35 | 0.35 |
| Fragrance Microcapsules (Example 3) | 1.2 | 1.2 | 1.2 |

[1] Glycidol Silicone VC2231-193
[2] Glycidol Silicone VC2231-193F
[3] Glycidol Silicone VC2231-193A
[4] Cyclopentasiloxane: SF1202 available from Momentive Performance Chemicals
[5] Behenyl trimethyl ammonium chloride/Isopropyl alcohol: Genamin ™ KMP available from Clariant
[6] Cetyl alcohol: Konol ™ series available from Shin Nihon Rika
[7] Stearyl alcohol: Konol ™ series available from Shin Nihon Rika
[8] Methylchloroisothiazolinone/Methylisothiazolinone: Kathon TM CG available from Rohm & Haas
[9] Panthenol: Available from Roche
[10] Panthenyl ethyl ether: Available from Roche

| | EXAMPLE COMPOSITION | |
|---|---|---|
| Ingredient | VII | VIII |
| Sodium Laureth Sulfate | 10.00 | 10.00 |
| Sodium Lauryl Sulfate | 1.50 | 1.50 |
| Cocamidopropyl betaine | 2.00 | 2.00 |
| Guar Hydroxypropyl trimonium chloride (1) | 0.40 | |
| Guar Hydroxypropyl trimonium chloride (2) | | 0.40 |
| Dimethicone (3) | 2.00 | 2.00 |
| Gel Network (4) | | 27.27 |
| Ethylene Glycol Distearate | 1.50 | 1.50 |
| 5-Chloro-2-methyl-4-isothiazolin-3-one, Kathon CG | 0.0005 | 0.0005 |
| Sodium Benzoate | 0.25 | 0.25 |
| Disodium EDTA | 0.13 | 0.13 |
| Perfume | 0.70 | 0.70 |
| Fragrance Microcapsules of Example 3 | 1.0 | 1.0 |

-continued

| Ingredient | EXAMPLE COMPOSITION | |
|---|---|---|
| | VII | VIII |
| Citric Acid/Sodium Citrate Dihydrate | pH QS | pH QS |
| Sodium Chloride/ | Visc. | Visc. |
| Ammonium Xylene Sulfonate | QS | QS |
| Water | QS | QS |

(1) Jaguar C17 available from Rhodia
(2) N-Hance 3269 (with Mol. W. of ~500,000 and 0.8 meq/g) available from Aqulaon/Hercules
(3) Viscasil 330M available from General Electric Silicones
(4) Gel Networks; See Composition below. The water is heated to about 74° C. and the Cetyl Alcohol, Stearyl Alcohol, and the SLES Surfactant are added to it. After incorporation, this mixture is passed through a heat exchanger where it is cooled to about 35° C. As a result of this cooling step, the Fatty Alcohols and surfactant crystallized to form a crystalline gel network.

Example 24. Microcapsules in Lotion

| | Example | | |
|---|---|---|---|
| | I | II | III |
| PHASE A | | | |
| DC-9040 [1] | 8.60 | 3.00 | 5.00 |
| Dimethicone | 4.09 | 4.00 | 4.00 |
| Polymethylsilsesquioxane [2] | 4.09 | 4.00 | 4.00 |
| Cyclomethicone | 11.43 | 0.50 | 11.33 |
| KSG-210 [3] | 5.37 | 5.25 | 5.40 |
| Polyethylene wax [4] | 3.54 | | 2.05 |
| DC-2503 Cosmetic Wax [5] | 7.08 | 10.00 | 3.77 |
| Hydrophobic TiO2 | | | 0.50 |
| Iron oxide coated Mica | | | 0.65 |
| TiO2 Coated Mica | 1.00 | 1.00 | |
| Fragrance Particles of Example 3 | 1.00 | 1.00 | 1.00 |
| PHASE B | | | |
| Glycerin | 10.00 | 10.00 | 10.00 |
| Dexpanthenol | 0.50 | 0.50 | 0.50 |
| Pentylene Glycol | 3.00 | 3.00 | 3.00 |
| Hexamidine Diisethionate [6] | 0.10 | 0.10 | 0.10 |
| Niacinamide [7] | 5.00 | 5.00 | 5.00 |
| Methylparaben | 0.20 | 0.20 | 0.20 |
| Ethylparaben | 0.05 | 0.05 | 0.05 |
| Sodium Citrate | 0.20 | 0.20 | 0.20 |
| Citric Acid | 0.03 | 0.03 | 0.03 |
| Sodium Benzoate | 0.05 | 0.05 | 0.05 |
| Sodium Chloride | 0.50 | 0.50 | 0.50 |
| FD&C Red #40 (1%) | 0.05 | 0.05 | 0.05 |
| Water | q.s to 100 | q.s to 100 | q.s to 100 |
| Hardness at 21° C. (g) | 33.3 | 15.4 | 14.2 |
| Hardness at 33° C. (g) | 6.4 | 0.7 | 4.0 |

[1] 12.5% Dimethicone Crosspolymer in Cyclopentasiloxane. Available from Dow Corning™.
[2] E.g., Tospearl™ 145A or Tospearl 2000. Available from GE Toshiba Silicone™.
[3] 25% Dimethicone PEG-10/15 Crosspolymer in Dimethicone. Available from Shin-Etsu™.
[4] Jeenate™ 3H polyethylene wax from Jeen™
[5] Stearyl Dimethicone. Available from Dow Corning.
[6] Hexamidine diisethionate, available from Laboratoires Serobiologiques.
[7] Additionally or alternatively, the composition may comprise one or more other skin care actives, their salts and derivatives, as disclosed herein, in amounts also disclosed herein as would be deemed suitable by one of skill in the art.

For the examples above, in a suitable container, combine the ingredients of Phase A. In a separate suitable container, combine the ingredients of Phase B. Heat each phase to 73° C.-78° C. while mixing each phase using a suitable mixer (e.g., Anchor blade, propeller blade, or IKA T25) until each reaches a substantially constant desired temperature and is homogenous. Slowly add Phase B to Phase A while continuing to mix Phase A. Continue mixing until batch is uniform. Pour product into suitable containers at 73-78° C. and store at room temperature. Alternatively, continuing to stir the mixture as temperature decreases results in lower observed hardness values at 21 and 33° C.

Example 25. Microcapsules in Single Unit Dose Personal Care Product

The following surfactant/polymer liquid processing composition is prepared at the indicated weight percentages as described in Table 1 below.

TABLE 1

| Component | |
|---|---|
| Glycerin | 3.2 |
| Polyvinyl alcohol[1] | 8.1 |
| Sodium Lauroamphoacetate (26% activity)[2] | 31.8 |
| Ammonium Laureth-3 sulfate (25% activity) | 4.9 |
| Ammonium Undecyl sulfate (24% activity) | 19.9 |
| Ammonium Laureth-1 sulfate (70% activity) | 8.0 |
| Cationic cellulose[3] | 0.5 |
| Citric Acid | 1.6 |
| Distilled water | 22.0 |
| Total | 100.0 |
| pH | 5.8 |
| Viscosity (cp) | 35,400 |

[1]Sigma-Aldrich Catalog No. 363081, MW 85,000-124,000, 87-89% hydrolyzed
[2]McIntyre Group Ltd, University Park, IL, Mackam HPL-28ULS
[3]UCARE™ Polymer LR-400, available from Amerchol Corporation (Plaquemine, Louisiana)

A target weight of 300 grams of the above composition is prepared with the use of a conventional overhead stirrer (IKA® RW20DZM Stirrer available from IKA® Works, Inc., Wilmington, DE) and a hot plate (Corning Incorporated Life Sciences, Lowell, MA). Into an appropriately sized and cleaned vessel, the distilled water and glycerin are added with stirring at 100-150 rpm. The cationic polymer, when present, is then slowly added with constant stirring until homogenous. The polyvinyl alcohol is weighed into a suitable container and slowly added to the main mixture in small increments using a spatula while continuing to stir while avoiding the formation of visible lumps. The mixing speed is adjusted to minimize foam formation. The mixture is slowly heated to 80° C. after which surfactants are added. The mixture is then heated to 85° C. while continuing to stir and then allowed to cool to room temperature. Additional distilled water is added to compensate for water lost to evaporation (based on the original tare weight of the container). The final pH is between 5.2-6.6 and adjusted with citric acid or diluted sodium hydroxide if necessary. The resulting processing mixture viscosity is measured.

A porous dissolvable solid substrate (also referred to in the examples herein as "substrate") is prepared from the above liquid processing mixture as described in Table 2 below.

TABLE 2

| | |
|---|---|
| Aeration Time (sec) | 62 |
| Wet Density (g/cm$^3$) | 0.26 |
| Oven Temperature (° C.) | 130 |
| Drying Time (min) | 38 |
| Average dry substrate weight (g) | 1.10 |
| Average dry substrate thickness (cm) | 0.62 |
| Average substrate shrinkage (%) | 4.6% |
| Average dry substrate density (g/cm$^3$) | 0.11 |
| Average basis weight (g/m$^2$) | 650 |

300 grams of the processing mixture is stored within a convection oven for greater than two hours at 70° C. to pre-heat the processing mixture. The mixture is then transferred into a pre-heated 5 quart stainless steel bowl (by placing into 70° C. oven for greater than 15 minutes) of a KITCHENAID® Mixer Model K5SS (available from Hobart Corporation, Troy, OH) fitted with a flat beater attachment and with a water bath attachment comprising tap water at 70-75° C. The mixture is vigorously aerated at a maximum speed setting of 10 until a wet density of approximately 0.26 grams/cm$^3$ is achieved (time recorded in table). The density is measured by weighing a filling a cup with a known volume and evenly scraping off the top of the cup with a spatula. The resulting aerated mixture is then spread with a spatula into square 160 mm×160 mm aluminum molds with a depth of 6.5 mm with the excess wet foam being removed with the straight edge of a large metal spatula that is held at a 45° angle and slowly dragged uniformly across the mold surface. The aluminum molds are then placed into a 130° C. convection oven for approximately 35 to 45 minutes. The molds are allowed to cool to room temperature with the substantially dry porous dissolvable solid substrates removed from the molds with the aid of a thin spatula and tweezers.

Each of the resulting 160 mm×160 mm square substrates is cut into nine 43 mm×43 mm squares (with rounded edges) using a cutting die and a Samco SB20 cutting machine (each square representing surface area of approximately 16.9 cm$^2$). The resulting smaller substrates are then equilibrated overnight (14 hours) in a constant environment room kept at 70° F. and 50% relative humidity within large zip-lock bags that are left open to the room atmosphere.

Within a fume hood, the substrate is mounted on a stainless steel easel that rests at about a 60 degree angle and with notches holding the substrate from sliding downward and with a hole in plate so that the substrate can easily be removed from the mount by pushing from the easel. It is important that the top surface of the substrate (the side that is exposed to the air in the drying oven and opposite the side that is in direct contact with the aluminum mold during the drying process) is facing away from the easel. A small glass bottle with a pump spray is filled with the primary fragrance oil 1a and then sprayed onto the surface of the substrate from a distance of 2 to 3 inches. The substrate is then removed from the easel and returned to the weigh boat on the balance with the top side facing upwards. The weight of perfume applied is recorded and in the instance that the target weight is not achieved, either another spray amount is applied or a Kim wipe to absorb excess perfume away from the substrate. This iterative process is repeated until the target weight range is achieved. The amount of fragrance 1a applied is recorded in the below table. The resulting substrate resting on the small weigh boat is stored within a zip-lock bag and sealed from the atmosphere. The above process is repeated on a second substrate.

The first substrate within its weigh boat is later removed from the zip-lock bag and tared again to zero weight on a 4 place weigh balance. A perfume microcapsule of Example 21 is then applied to the surface of each substrate. The substrate is coated with the perfume microcapsule powder by gently shaking the substrate in a tray (or other suitable container) containing an excess of the perfume inclusion complex in a side-to-side manner ten times (the process is repeated for the other side). The resulting powder coated substrate is then picked up (with gloved hands) and gently shaken and tapped several times to remove any excess powder that is not sufficiently adhered to the substrate. The resulting weight of the microcapsule of the secondary fragrance applied is recorded in the below table. The porous substrate within its weigh boat is then returned the zip lock bag and sealed from the atmosphere. This powder application process is repeated for the second substrate.

The final weights achieved are given in the below table:

| Substrate No. | Initial substrate weight | Weight of primary fragrance applied | Weight of Scent A perfume microcapsule powder (Example 21) |
|---|---|---|---|
| 1 | 1.194 | 0.050 | 0.0175 |
| 2 | 1.063 | 0.055 | 0.0150 |
| Averages | 1.129 | 0.053 | 0.0161 |

Example 26. Microcapsules in Antiperspirant/Deodorant

| Ingredient | Comparative Example I | Comparative Example II[9] | Example III | Example IV | Example V |
|---|---|---|---|---|---|
| Part I: Partial Continuous Phase | | | | | |
| Hexamethyldisiloxane[1] | 22.65 | 21.25 | 21.25 | 21.25 | 21.25 |
| DC5200[2] | 1.20 | 1.20 | 1.20 | 1.20 | |
| Fragrance | 0.35 | 1.25 | 1.25 | 1.25 | 1.25 |
| Fragrance Capsules of Example 3 | 1.00 | 1.00 | 1.00 | 1.00 | 1.00 |
| Shin Etsu KF 6038[3] | | | | | 1.20 |
| Part II: Disperse Phase | | | | | |
| ACH (40% solution)[4] | 40.00 | 55.0 | | | |
| IACH (34% solution)[5] | | 2.30 | 49.00 | | |
| ZAG (30% solution)[6] | | | | 52.30 | 52.30 |
| propylene glycol | 5.00 | | 5.00 | 5.00 | 5.00 |
| water | 12.30 | | 3.30 | | |
| Part III: Structurant Plus Remainder of Continuous Phase | | | | | |
| FinSolve TN | 6.50 | 6.00 | 6.50 | 6.00 | 6.50 |
| Ozocrite Wax | | | | | 12.00 |
| Performalene PL[7] | 11.00 | 11.00 | 12.00 | 12.00 | |
| Aqueous Phase Conductivity (mS/cm) | 37.7 | 79.5 | 40.5 | 60.3 | 60.3 |

[1]DC 246 fluid from Dow Corning
[2]from Dow Corning
[3]from Shinetsu
[4]Standard aluminum chlorohydrate solution
[5]IACH solution stabilized with calcium
[6]IZAG solution stabilized with calcium
[7]from New Phase Technologies
[9]emulsion broke when manufacturing this composition The above examples I through V can be made via the following general process, which one skilled in the art will be able to alter to incorporate available equipment. The ingredients of Part I and Part II are mixed in separate suitable containers. Part II is then added slowly to Part I under agitation to assure the making of a water-in-silicone emulsion. The emulsion is then milled with suitable mill, for example a Greeco 1L03 from Greeco Corp, to create a homogenous emulsion. Part III is mixed and heated to 88° C. until the all solids are completely melted. The emulsion is then also heated to 88° C. and then added to the Part 3 ingredients. The final mixture is then poured into an appropriate container, and allowed to solidify and cool to ambient temperature.

| Ingredient | VI | VII | VIII | EX | X |
|---|---|---|---|---|---|
| | \multicolumn{5}{c}{Product Form} | | | | |
| | Solid Deodorant | Solid Deodorant | Solid Deodorant | Solid Deodorant | Deodorant or Body Spray |
| dipropylene glycol | 45 | 22 | 20 | 30 | 20 |
| propylene glycol | 22 | 45 | 22 | | |
| tripopylene glycol | | | 25 | | |
| glycerine | | | | 10 | |
| PEG -8 | | | | 20 | |
| ethanol | | | | | QS |
| water | QS | QS | QS | QS | |
| sodium stearate | 5.5 | 5.5 | 5.5 | 5.5 | |
| tetra sodium EDTA | 0.05 | 0.05 | 0.05 | 0.05 | |
| sodium hydroxide | 0.04 | 0.04 | 0.04 | 0.04 | |

Examples VI to IX can be made as follows: all ingredients except the fragrance, linalool, and dihydromyrcenol are combined in a suitable container and heated to about 85° C. to form a homogenous liquid. The solution is then cooled to about 62° C. and then the fragrance, linalool, and dihydromyrcenol are added. The mixture is then poured into an appropriate container and allowed to solidify up cooling to ambient temperature.

Example X can be made as follows: all the ingredients except the propellant are combined in an appropriate aerosol container. The container is then sealed with an appropriate aerosol delivery valve. Next air in the container is removed by applying a vacuum to the valve and then propellant is added to container through the valve. Finally an appropriate actuator is connected to the valve to allow dispensing of the product.

Example 27. Microcapsules in Rinse-Off Conditioner

| Components | Ex. I | Ex. II | Ex. III | Ex. IV | Ex. V | Ex. VI (Comparative example, w/PDMS instead of amino silicone) |
|---|---|---|---|---|---|---|
| Premix | | | | | | |
| Aminosilicone-1 *1 | 0.50 | 0.50 | | | | |
| Aminosilicone-2 *2 | | | 0.50 | 0.50 | 0.50 | |
| PDMS | | | | | | 0.50 |
| Fragrance microcapsules of Example 13 | . . . | 1.0 | 1.0 | 1.0 | 1.0 | 1.0 |
| Gel matrix carrier | | | | | | |
| Behenyl trimethyl ammonium chloride | 2.30 | 2.30 | 2.30 | 2.30 | 2.30 | 2.30 |
| Cetyl alcohol | 1.5 | 1.5 | 1.5 | 1.5 | 1.5 | 1.5 |
| Stearyl alcohol | 3.8 | 3.8 | 3.8 | 3.8 | 3.8 | 3.8 |
| Deionized Water | QS | QS | QS | QS | QS | QS |
| Preservatives | 0.4 | 0.4 | 0.4 | 0.4 | 0.4 | 0.4 |
| Panthenol | — | — | 0.03 | — | — | — |
| Panthenyl ethyl ether | — | — | 0.03 | — | — | — |

Definitions of Components
*1 Aminosilicone-1 (AMD): having an amine content of 0.12-0.15 mmol/g and a viscosity of 3,000-8,000 mPa · s, which is water insoluble
*2 Aminosilicone-2 (TAS): having an amine content of 0.04-0.06 mmol/g and a viscosity of 10,000-16,000 mPa · s, which is water insoluble -continued

| Ingredient | VI | VII | VIII | EX | X |
|---|---|---|---|---|---|
| | \multicolumn{5}{c}{Product Form} | | | | |
| | Solid Deodorant | Solid Deodorant | Solid Deodorant | Solid Deodorant | Deodorant or Body Spray |
| triclosan | 0.3 | 0.3 | 0.3 | 0.3 | |
| Fragrmce | 0.5 | 0.5 | 0.5 | 0.5 | 0.5 |
| Fragrance capsules of Example 3 | 1.0 | 1.0 | 1.0 | 1.0 | 0.5 |
| dihydromyrcenol | 0.3 | .1 | 0.3 | 0.5 | .1 |
| linalool | 0.2 | .15 | 0.2 | 0.25 | .15 |
| Propellant (1,1 difluoroethane) | | | | | 40 |

QS - indicates that this material is used to bring the total to 100%.

Method of Preparation

The conditioning compositions of "Ex. I" through "Ex. VI" are prepared as follows: Cationic surfactants, high melting point fatty compounds are added to water with agitation, and heated to about 80° C. The mixture is cooled down to about 50° C. to form a gel matrix carrier. Separately, slurries of perfume microcapsules and silicones are mixed with agitation at room temperature to form a premix. The premix is added to the gel matrix carrier with agitation. If included, other ingredients such as preservatives are added with agitation. Then the compositions are cooled down to room temperature.

The conditioning composition of "Ex. II" is prepared as follows: Cationic surfactants, high melting point fatty compounds are added to water with agitation, and heated to about 80° C. The mixture is cooled down to about 50° C. to form a gel matrix carrier. Then, silicones are added with agitation. Separately, slurries of perfume microcapsules, and if included, other ingredients such as preservatives are added with agitation. Then the compositions are cooled down to room temperature.

Example 28. Microcapsules in a Body Cleansing Composition

|  | Example D | Example E | Example F |
|---|---|---|---|
| I: Cleansing Phase Composition | | | |
| Sodium Trideceth Sulfate (sulfated from Iconol TDA-3 (BASF Corp.) to >95% sulfate) | 5.9 | 5.9 | 5.9 |
| Sodium Lauryl Sulfate (Procter and Gamble) | 5.9 | 5.9 | 5.9 |
| Sodium Lauroamphoacetate (Cognis Chemical Corp.,) | 3.6 | 3.6 | 3.6 |
| Guar Hydroxypropyltrimonium Chloride (N-Hance 3196 from Aqualon) | — | 0.3 | 0.7 |
| Guar Hydroxypropyltrimonium Chloride (Jaguar C-17 from Rhodia) | 0.6 | — | — |
| Stabylen 30 (Acrylates/Vinyl Isodecanoate, 3V) | 0.33 | 0.33 | 0.33 |
| Sodium Chloride | 3.75 | 3.75 | 3.75 |
| Trideceth-3 (Iconal TDA-3 from BASF Corp.) | 1.75 | 1.75 | 1.75 |
| Methyl chloro isothiazolinone and methyl isothiazolinone (Kathon CG, Rohm & Haas) | 0.033 | 0.033 | 0.033 |
| EDTA (Dissolvine NA 2x) | 0.15 | 0.15 | 0.15 |
| Sodium Benzoate | 0.2 | 0.2 | 0.2 |
| Citric Acid, titrate | pH = 5.7 ± 0.2 | pH = 5.7 ± 0.2 | pH = 5.7 ± 0.2 |
| Perfume | 1.11% | 1.11% | 1.11% |
| Water and Minors (NaOH) | Q.S. | Q.S. | Q.S. |
| II: Benefit Phase Composition | | | |
| Petrolatum (G2218 from Sonnerbonn) | 60 | 60 | 60 |
| Mineral Oil (Hydrobrite 1000 from Sonnerbonn) | 20 | 20 | 20 |
| Fragrance Microcapsules of Example 3 | 10 | 10 | 10 |
| III: Surfactant Phase:Benefit Phase Blending Ratio | 50:50 | 90:10 | 90:10 |

Example 29. Microcapsules in Fabric Softening Product

Non-limiting examples of product formulations containing purified perfume microcapsules of the aforementioned examples are summarized in the following table.

| (% wt) | A | B | C | D | E | F | G | H | I | J |
|---|---|---|---|---|---|---|---|---|---|---|
| FSA [a] | 14 | 16.47 | 14 | 12 | 12 | 16.47 | — | — | 5 | 5 |
| FSA [b] | | | | | — | | 3.00 | — | — | — |
| FSA [c] | | | | | — | | — | 6.5 | — | — |
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Starch [d] | 1.25 | 1.47 | 2.00 | 1.25 | — | 2.30 | 0.5 | 0.70 | 0.71 | 0.42 |
| Microcapsule (% active)* | 0.6 | 0.75 | 0.6 | 0.75 | 0.37 | 0.60 | 0.37 | 0.6 | 0.37 | 0.37 |
| Phase Stabilizing Polymer [f] | 0.21 | 0.25 | 0.21 | 0.21 | 0.14 | — | — | 0.14 | — | — |
| Suds Suppressor [g] | — | — | — | — | — | — | — | 0.1 | — | — |
| Calcium Chloride | 0.15 | 0.176 | 0.15 | 0.15 | 0.30 | 0.176 | — | 0.1-0.15 | — | — |
| DTPA [h] | 0.017 | 0.017 | 0.017 | 0.017 | 0.007 | 0.007 | 0.20 | — | 0.002 | 0.002 |
| Preservative (ppm) [i,j] | 5 | 5 | 5 | 5 | 5 | 5 | — | 250 [j] | 5 | 5 |
| Antifoam [k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |

-continued

| (% wt) | EXAMPLES | | | | | | | | | |
|---|---|---|---|---|---|---|---|---|---|---|
| | A | B | C | D | E | F | G | H | I | J |
| HCl | 0.012 | 0.014 | 0.012 | 0.012 | 0.028 | 0.028 | 0.016 | 0.025 | 0.011 | 0.011 |
| Structurant[l] | 0.01 | 0.01 | 0.01 | 0.01 | 0.01 | 0.01 | 0.01 | 0.01 | 0.01 | 0.01 |
| Neat Unencapsulated Perfume | 0.8 | 0.7 | 0.9 | 0.5 | 1.2 | 0.5 | 1.1 | 0.6 | 1.0 | 0.9 |
| Deionized Water | Balance | Balance | Balance | Balance | Balance | Balance | Balance | Balance | Balance | Balance |

[a] N,N-di(tallowoyloxyethyl)-N,N-dimethylammonium chloride.
[b] Methyl bis(tallow amidoethyl)2-hydroxyethyl ammonium methyl sulfate.
[c] Reaction product of Fatty acid with Methyldiethanolamine in a molar ratio 1.5:1, quaternized with Methylchloride, resulting in a 1:1 molar mixture of N,N-bis(stearoyl-oxy-ethyl) N,N-dimethyl ammonium chloride and N-(stearoyl-oxy-ethyl) N,-hydroxyethyl N,N dimethyl ammonium chloride.
[d] Cationic high amylose maize starch available from National Starch under the trade name CATO ®.
[f] Copolymer of ethylene oxide and terephthalate having the formula described in U.S. Pat. No. 5,574,179 at col. 15, lines 1-5, wherein each X is methyl, each n is 40, u is 4, each R1 is essentially 1,4-phenylene moieties, each R2 is essentially ethylene, 1,2-propylene moieties, or mixtures thereof.
[g] SE39 from Wacker
[h] Diethylenetriaminepentaacetic acid.
[i] KATHON ® CG available from Rohm and Haas Co. "PPM" is "parts per million."
[j] Gluteraldehyde
[k] Silicone antifoam agent available from Dow Corning Corp. under the trade name DC2310.
[l] Hydrophobically-modified ethoxylated urethane available from Rohm and Haas under the tradename Aculyn™ 44.
*Suitable combinations of the microcapsules provided in Examples 1 through 20. (Percent active relates to the core content of the microcapsule.)

Example 30. Microcapsules in Dry Laundry Formulations

Non-limiting examples of product formulations containing purified perfume microcapsules of the aforementioned examples are summarized in the following table.

| Component | % w/w granular laundry detergent composition | | | | | | |
|---|---|---|---|---|---|---|---|
| | A | B | C | D | E | F | G |
| Brightener | 0.1 | 0.1 | 0.1 | 0.2 | 0.1 | 0.2 | 0.1 |
| Soap | 0.6 | 0.6 | 0.6 | 0.6 | 0.6 | 0.6 | 0.6 |
| Ethylenediamine disuccinic acid | 0.1 | 0.1 | 0.1 | 0.1 | 0.1 | 0.1 | 0.1 |
| Acrylate/maleate copolymer | 1.5 | 1.5 | 1.5 | 1.5 | 1.5 | 1.5 | 1.5 |
| Hydroxyethane di(methylene phosphonic acid) | 0.4 | 0.4 | 0.4 | 0.4 | 0.4 | 0.4 | 0.4 |
| Mono-$C_{12}$-$C_{14}$ alkyl, di-methyl, mono-hydroyethyl quaternary ammonium chloride | 0.5 | 0.5 | 0.5 | 0.5 | 0.5 | 0.5 | 0.5 |
| Linear alkyl benzene | 0.1 | 0.1 | 0.2 | 0.1 | 0.1 | 0.2 | 0.1 |
| Linear alkyl benzene sulphonate | 10.3 | 10.1 | 19.9 | 14.7 | 10.3 | 17 | 10.5 |
| Magnesium sulphate | 0.4 | 0.4 | 0.4 | 0.4 | 0.4 | 0.4 | 0.4 |
| Sodium carbonate | 19.5 | 19.2 | 10.1 | 18.5 | 29.9 | 10.1 | 16.8 |
| Sodium sulphate | 29.6 | 29.8 | 38.8 | 15.1 | 24.4 | 19.7 | 19.1 |
| Sodium Chloride | 0.1 | 0.1 | 0.1 | 0.1 | 0.1 | 0.1 | 0.1 |
| Zeolite | 9.6 | 9.4 | 8.1 | 18 | 10 | 13.2 | 17.3 |
| Photobleach particle | 0.1 | 0.1 | 0.2 | 0.1 | 0.2 | 0.1 | 0.2 |
| Blue and red carbonate speckles | 1.8 | 1.8 | 1.8 | 1.8 | 1.8 | 1.8 | 1.8 |
| Ethoxylated Alcohol AE7 | 1 | 1 | 1 | 1 | 1 | 1 | 1 |
| Tetraacetyl ethylene diamine agglomerate (92 wt % active) | 0.9 | 0.9 | 0.9 | 0.9 | 0.9 | 0.9 | 0.9 |
| Citric acid | 1.4 | 1.4 | 1.4 | 1.4 | 1.4 | 1.4 | 1.4 |
| PDMS/clay agglomerates (9.5% wt % active PDMS) | 10.5 | 10.3 | 5 | 15 | 5.1 | 7.3 | 10.2 |
| Polyethylene oxide | 0.2 | 0.2 | 0.2 | 0.2 | 0.2 | 0.2 | 0.2 |
| Enzymes e.g. Protease (84 mg/g active), Amylase (22 mg/g active) | 0.2 | 0.3 | 0.2 | 0.1 | 0.2 | 0.1 | 0.2 |
| Suds suppressor agglomerate (12.4 wt % active) | 0.2 | 0.2 | 0.2 | 0.2 | 0.2 | 0.2 | 0.2 |
| Sodium percarbonate (having from 12% to 15% active AvOx) | 7.2 | 7.1 | 4.9 | 5.4 | 6.9 | 19.3 | 13.1 |
| Perfume oil | 0.5 | 0.5 | 0.5 | 0.5 | 0.5 | 0.5 | 0.5 |
| Solid perfume particles | 0.4 | 0 | 0.4 | 0.4 | 0.4 | 0.4 | 0.6 |

-continued

| Component | % w/w granular laundry detergent composition | | | | | | |
|---|---|---|---|---|---|---|---|
| | A | B | C | D | E | F | G |
| Perfume microcapsules* | 1.3 | 2.4 | 1 | 1.3 | 1.3 | 1.3 | 0.7 |
| Water | 1.4 | 1.4 | 1.4 | 1.4 | 1.4 | 1.4 | 1.4 |
| Misc | 0.1 | 0.1 | 0.1 | 0.1 | 0.1 | 0.1 | 0.1 |
| Total Parts | 100 | 100 | 100 | 100 | 100 | 100 | 100 |

*Microcapsule added as 25-35% active slurry (aqueous solution). Core/wall ratio can range from 80/20 up to 90/10 and average particle diameter can range from 5 μm to 50 μm, and can be purified via any of the aforementioned examples. Suitable combinations of the microcapsules provided in Examples 1 through 21.

Example 31. Liquid Laundry Formulations (HDLs)

Non-limiting examples of product formulations containing purified perfume microcapsules of the aforementioned examples are summarized in the following table.

| Ingredient | HDL 1 | HDL 2 | HDL3 | HDL4 | HDL 5 | HDL 6 |
|---|---|---|---|---|---|---|
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |
| Glutaraldehyde | 0 | 0 | 19 ppm | 0 | 13 ppm | 0 |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Silicone (PDMS) emulsion | 0.003 | 0.003 | 0.003 | 0.003 | 0.003 | 0.003 |
| Perfume | 0.7 | 0.5 | 0.8 | 0.8 | 0.6 | 0.6 |
| Polyethyleneimine | 0.01 | 0.10 | 0.00 | 0.10 | 0.20 | 0.05 |
| Perfume Microcapsules* | 1.00 | 5.00 | 1.00 | 2.00 | 0.10 | 0.80 |
| Water | Balance to 100% | Balance to 100% | Balance to 100% | Balance to 100% | Balance to 100% | Balance to 100% |

Non-limiting examples of product formulations containing purified perfume microcapsules of the aforementioned examples are summarized in the following table.

| Examples of liquid detergents | A | B | C | D |
|---|---|---|---|---|
| $C_{14}$-$C_{15}$ alkyl poly ethoxylate (8) | 6.25 | 4.00 | 6.25 | 6.25 |
| $C_{12}$-$C_{14}$ alkyl poly ethoxylate (7) | 0.40 | 0.30 | 0.40 | 0.40 |
| $C_{12}$-$C_{14}$ alkyl poly ethoxylate (3) | 10.60 | 6.78 | 10.60 | 10.60 |
| sulfate Na salt | | | | |
| Linear Alkylbenzene sulfonate acid | 0.19 | 1.16 | 0.79 | 0.79 |
| Citric Acid | 3.75 | 2.40 | 3.75 | 3.75 |
| $C_{12}$-$C_{18}$ Fatty Acid | 4.00 | 2.56 | 7.02 | 7.02 |
| Enzymes | 0.60 | 0.4 | 0.60 | 0.60 |
| Boric Acid | 2.4 | 1.5 | 1.25 | 1.25 |
| Trans-sulphated ethoxylated | 1.11 | 0.71 | 1.11 | 1.11 |

| Examples of liquid detergents | A | B | C | D |
|---|---|---|---|---|
| hexamethylene diamine quat | | | | |
| Diethylene triamine penta methylene phosphonic acid | 0.17 | 0.11 | 0.17 | 0.17 |
| Fluorescent brightener | 0.09 | 0.06 | 0.14 | 0.14 |
| Hydrogenated Castor Oil | 0.05 | 0.300 | 0.20 | 0.20 |
| Ethanol | 2.50 | 1.00 | 2.50 | 2.50 |
| 1,2 propanediol | 1.14 | 0.7 | 1.14 | 1.14 |
| Sodium hydroxide | 3.8 | 2.6 | 4.60 | 4.60 |
| Mono Ethanol Amine | 0.8 | 0.5 | | |
| Na Cumene Sulphonate | | | | |
| Silicone emulsion | 0.0030 | 0.0030 | 0.0030 | 0.0030 |
| Dye | 0.002 | 0.002 | 0.002 | 0.002 |
| Opacifier (Styrene Acrylate based) | | | | |
| Bentonite Softening Clay | | 1.0 | | |
| Acrylamide/MAPTAC (ex Nalco Chemicals of Naperville, IL) | | | 0.40 | |
| Mirapol 550 (ex Rhodia Chemie, France) | | | | 0.4 |
| PP-5495 (silicone ex Dow Corning Corporation, Midland, MI) | | 1.0 | | |
| DC 1664 (silicone ex Dow Corning Corporation, Midland, MI) | 1.0 | | | |
| Pearlescent agent * | | | | 0.2 |
| Perfume micro capsules** (expressed as perfume oil) | 0.8 | 0.5 | 1.0 | 0.7 |
| Perfume | 0.7 | 0.55 | 1.00 | 1.00 |
| Poly Ethylene Imine MW 25000 | 0.1 | 0.01 | | |
| Water | Up to 100 | Up to 100 | Up to 100 | Up to 100 |

* Mica-$TiO_2$ (Prestige Silk Silver Star ex Eckart) or BiOCl (Biron Silver CO - Merck) or pre-crystallized EGDS (Tegopearl N 100 ex Degussa, expressed as pure EGDS)
**Microcapsule added as 25-35% active slurry (aqueous solution). Core/wall ratio can range from 80/20 up to 90/10 and average particle diameter can range from 5 μm to 50 μm, and can be purified via any of the aforementioned examples. Suitable combinations of the microcapsules provided in Example 6.

| Examples of liquid detergents | E | F | G | H |
|---|---|---|---|---|
| $C_{14}$-$C_{15}$ alkyl poly ethoxylate (8) | 6.25 | 4.00 | 6.25 | 6.25 |
| $C_{12}$-$C_{14}$ alkyl poly ethoxylate (7) | 0.40 | 0.30 | 0.40 | |
| $C_{12}$-$C_{14}$ alkyl poly ethoxylate (3) sulfate Na salt | 10.60 | 6.78 | 10.60 | 10.60 |
| Linear Alkylbenzene sulfonate acid | 0.79 | 1.19 | 0.79 | 0.79 |
| Citric Acid | 3.75 | 2.40 | 3.75 | 3.75 |
| $C_{12}$-$C_{18}$ Fatty Acid | 7.02 | 4.48 | 7.02 | 7.02 |
| Enzymes | 0.60 | 1.0 | 0.60 | |
| Boric Acid | 1.25 | 1.25 | 1.25 | 1.25 |
| Trans-sulphated ethoxylated hexamethylene diamine quat | 1.11 | 0.71 | 1.11 | 1.11 |
| Diethylene triamine penta methylene phosphonic acid | 0.17 | 0.11 | 0.17 | 0.17 |
| Fluorescent brightener | 0.14 | 0.06 | 0.14 | |
| Hydrogenated Castor Oil | 0.20 | 0.300 | 0.20 | 0.20 |
| Ethanol | 2.50 | 1.00 | 2.50 | 2.50 |
| 1,2 propanediol | 1.14 | 0.09 | 1.14 | 1.14 |
| Sodium hydroxide | 4.60 | 3.01 | 4.60 | 4.60 |
| Mono Ethanol Amine | 2.0 | 1.0 | 0.5 | |
| Na Cumene Sulphonate | | | | 1.6 |
| Silicone emulsion | 0.0030 | 0.0030 | 0.0030 | 0.0030 |
| Dye | 0.002 | 0.00084 | 0.00084 | 0.00084 |
| Opacifier (Styrene Acrylate based) | | | | 0.1 |
| Bentonite Softening Clay | | | | 1.0 |
| Acrylamide/MAPTAC (ex Nalco Chemicals of Naperville, IL) | | | 0.40 | |
| Mirapol 550 (ex Rhodia Chemie, France) | 0.40 | 0.25 | | |
| Polyquaternium 10 - Cationic hydroxyl ethyl cellulose | | | | 0.30 |
| PP-5495 (silicone ex Dow Corning Corporation, Midland, MI) | | 3.0 | | |
| DC 1664 (silicone ex Dow Corning Corporation, Midland, MI) | 3.0 | | 3.0 | |
| Pearlescent agent * | | | 0.2 | |
| Perfume micro capsules** (expressed as perfume oil) | 0.9 | 0.3 | 0.5 | 1.2 |
| Perfume | 1.00 | 0.65 | 1.00 | 1.00 |
| Poly Ethylene Imine MW 25000 | | | | |
| Water | Up to 100 | Up to 100 | Up to 100 | Up to 100 |

* Mica-$TiO_2$ (Prestige Silk Silver Star ex Eckart) or BiOCl (Biron Silver CO - Merck) or pre-crystallized EGDS (Tegopearl N 100 ex Degussa, expressed as pure EGDS)
**Microcapsule added as 25-35% active slurry (aqueous solution). Core/wall ratio can range from 80/20 up to 90/10 and average particle diameter can range from 5 μm to 50 μm, and can be purified via any of the aforementioned examples. Suitable combinations of the microcapsules provided in Examples 1 through 21.

| Examples of liquid detergents | I | J | K |
|---|---|---|---|
| $C_{14}$-$C_{15}$ alkyl poly ethoxylate (8) | 4.00 | 6.1 | |
| $C_{12}$-$C_{14}$ alkyl poly ethoxylate (7) | | | 2.00 |
| $C_{12}$-$C_{14}$ alkyl poly ethoxylate (3) sulfate Na salt | 6.78 | | |
| Linear Alkylbenzene sulfonate acid | 1.19 | 7.8 | 15.0 |
| Citric Acid | 2.40 | 2.6 | 2.50 |
| $C_{12}$-$C_{18}$ Fatty Acid | 4.48 | 2.6 | 11.4 |
| Enzymes | | .55 | .07 |
| Boric Acid | 1.25 | 1.50 | 1.3 |
| Trans-sulphated ethoxylated hexamethylene diamine quat | 0.71 | 1.20 | |
| Diethylene triamine penta methylene phosphonic acid | 0.11 | 0.20 | 0.7 |
| Fluorescent brightener | | 0.09 | 0.14 |
| Hydrogenated Castor Oil | 0.300 | 0.45 | 0.09 |
| Ethanol | 1.00 | 1.40 | 0.7 |
| 1,2 propanediol | 0.09 | 3.30 | 6.7 |
| Sodium hydroxide | 3.01 | 3.00 | 5.5 |
| Mono Ethanol Amine | 1.0 | 0.50 | |
| Na Cumene Sulphonate | | | 1.6 |
| Silicone emulsion | 0.0030 | 0.0030 | 0.30 |
| Dye | 0.00084 | 0.02 | 0.004 |
| Opacifier (Styrene Acrylate based) | | | |
| Bentonite Softening Clay | | | 3.40 |
| Acrylamide/MAPTAC (ex Nalco Chemicals of Naperville, IL) | | | 1.0 |
| Mirapol 550 (ex Rhodia Chemie, France) | | 1.0 | |
| Polyquaternium 10 - Cationic hydroxyl ethyl cellulose | 0.18 | | 0.1 |
| PP-5495 (silicone ex Dow Corning Corporation, Midland, MI) | | 1.0 | |
| DC 1664 (silicone ex Dow Corning Corporation, Midland, MI) | 3.0 | | |
| Pearlescent agent * | 0.2 | | |
| Perfume micro capsules (expressed as perfume oil) | 0.2 | 0.45 | 0.75 |
| Perfume | 0.65 | 0.5 | 1.0 |
| Poly Ethylene Imine MW 25000 | | | 0.08 |
| Water | Up to 100 | Up to 100 | Up to 100 |

| Examples of liquid detergents | L | M ** | N |
|---|---|---|---|
| $C_{14}$-$C_{15}$ alkyl poly ethoxylate (8) | 3.7 | | 20.7 |
| $C_{12}$-$C_{14}$ alkyl poly ethoxylate (7) | | 16.7 | |
| $C_{12}$-$C_{14}$ alkyl poly ethoxylate (3) sulfate Na salt | 17.8 | | 5.5 |
| Linear Alkylbenzene sulfonate acid | 12.5 | 22.9 | 13.5 |
| Citric Acid | 3.9 | | 1.7 |
| $C_{12}$-$C_{18}$ Fatty Acid | 11.1 | 18 | 5.1 |
| Enzymes | 3 | 1.2 | 3 |
| Boric Acid | 0.5 | | 0.5 |
| Trans-sulphated ethoxylated hexamethylene diamine quat | 3.25 | | 1.2 |

-continued

| | | | |
|---|---|---|---|
| PEI 600 EO20 | 1.25 | | 1.2 |
| Diethylene triamine penta methylene phosphonic acid or HEDP | 1.6 | | 0.85 |
| Fluorescent brightener | 0.2 | 0.3 | 0.14 |
| Hydrogenated Castor Oil | | 0.2 | |
| 1,2 propanediol | 4.3 | 20.3 | 11.7 |
| Sodium hydroxide | | 1.0 | 3.9 |
| Mono Ethanol Amine | 9.8 | 6.8 | 3.1 |
| Dye | Present | Present | Present |
| PDMS | | 2.15 | |
| Potassium sulphite | | 0.2 | |
| Perfume micro capsules * (expressed as perfume oil) | 1.6 | 1.5 | 1.4 |
| Perfume | 1.2 | 1.6 | 1.0 |
| Form. Phenyl Boronic Acid | | | Present |
| Water | Up to 100 | Up to 100 | Up to 100 |

* Microcapsule added as 25-35% active slurry (aqueous solution). Core/wall ratio can range from 80/20 up to 90/10 and average particle diameter can range from 5 μm to 50 μm, and can be purified via any of the aforementioned examples. Suitable combinations of the microcapsules provided in Examples 1 through 21.
** Low water liquid detergent in Polyvinylalcohol unidose/sachet Examples 32: Liquid and Gel Detergents

TABLE 1

(% by Weight)

| Ingredients | 33 | 34 | 35 |
|---|---|---|---|
| Alkylbenzenesulfonic acid | 17.2 | 12.2 | 23 |
| $C_{12}$-$C_{14}$ alcohol 7-ethoxylate | 8.6 | 0.4 | 19.5 |
| $C_{14}$-$C_{15}$ alcohol 8-ethoxylate | — | 9.6 | — |
| $C_{12}$-$C_{14}$ alcohol 3-ethoxylate sulphate, Na salt | 8.6 | — | — |
| $C_8$-$C_{10}$ Alkylamidopropyldimethyl amine | — | — | 0.9 |
| Citric acid | 2.9 | 4.0 | — |
| $C_{12}$-$C_{18}$ fatty acid | 12.7 | 4.0 | 17.3 |
| Enzymes | 3.5 | 1.1 | 1.4 |
| Ethoxylated polyimine | 1.4 | — | 1.6 |
| Ethoxylated polyimine polymer, quaternized and sulphated | 3.7 | 1.8 | 1.6 |
| Hydroxyethane diphosphonic acids (HEDP) | 1.4 | — | — |
| Pentamethylene triamine pentaphosphonic acid | — | 0.3 | — |
| Catechol 2,5 disulfonate, Na salt | 0.9 | — | — |
| Fluorescent whitening agent | 0.3 | 0.15 | 0.3 |
| 1,2 propandiol | 3.5 | 3.3 | 22 |
| Ethanol | — | 1.4 | — |
| Diethylene glycol | — | 1.6 | — |
| 1-ethoxypentanol | 0.9 | — | — |
| Sodium cumene sulfonate | — | 0.5 | — |
| Monoethanolamine (MEA) | 10.2 | 0.8 | 8.0 |
| MEA borate | 0.5 | 2.4 | — |
| Sodium hydroxide | — | 4.6 | — |
| Perfume | 1.6 | 0.7 | 1.5 |
| Microcapsules* | 1.1 | 1.2 | 0.9 |
| Water** | 22.1 | 50.8 | 2.9 |
| Perfume, dyes, miscellaneous minors | Balance | Balance | Balance |
| Undiluted viscosity ($V_n$) at 20 s$^{-1}$, cps | 2700 | 400 | 300 |

*Microcapsule added as 25-35% active slurry (aqueous solution). Core/wall ratio can range from 80/20 up to 90/10 and average particle diameter can range from 5 μm to 50 μm, and can be purified via any of the aforementioned examples. Suitable combinations of the microcapsules provided in Examples 1 through 21.
**Low water liquid detergent in Polyvinylalcohol unidose/sachet Example 33: Liquid Unit Dose The following are examples of unit dose executions wherein the liquid composition is enclosed within a PVA film. The preferred film used in the present examples is Monosol M8630 76 μm thickness.

| | D 3 compartments | | | E 2 compartments Compartment # | | F 3 compartments | | |
|---|---|---|---|---|---|---|---|---|
| | 42 | 43 | 44 | 45 | 46 | 47 | 48 | 49 |
| | | | | Dosage (g) | | | | |
| | 34.0 | 3.5 | 3.5 | 30.0 | 5.0 | 25.0 | 1.5 | 4.0 |
| Ingredients | | | | Weight % | | | | |
| Alkylbenzene sulfonic acid | 20.0 | 20.0 | 20.0 | 10.0 | 20.0 | 20.0 | 25 | 30 |
| Alkyl sulfate | | | | 2.0 | | | | |
| $C_{12-14}$ alkyl 7-ethoxylate | 17.0 | 17.0 | 17.0 | | 17.0 | 17.0 | 15 | 10 |
| $C_{12-14}$ alkyl ethoxy 3 sulfate | 7.5 | 7.5 | 7.5 | | | 7.5 | 7.5 | |
| Citric acid | 0.5 | | 2.0 | 1.0 | | | | 2.0 |
| Zeolite A | | | | 10.0 | | | | |
| $C_{12-18}$ Fatty acid | 13.0 | 13.0 | 13.0 | | 18.0 | 18.0 | 10 | 15 |
| Sodium citrate | | | | 4.0 | 2.5 | | | |
| Enzymes | 0-3 | 0-3 | 0-3 | 0-3 | | 0-3 | 0-3 | 0-3 |
| Sodium Percarbonate | | | | 11.0 | | | | |
| TAED | | | | 4.0 | | | | |
| Polycarboxylate | | | | 1.0 | | | | |
| Ethoxylated Polyethylenimine[1] | 2.2 | 2.2 | 2.2 | | | | | |
| Hydroxyethane diphosphonic acid | 0.6 | 0.6 | 0.6 | 0.5 | | | 2.2 | |
| Ethylene diamine tetra(methylene phosphonic) acid | | | | | | 0.4 | | |

-continued

| | D<br>3 compartments | | | E<br>2 compartments<br>Compartment # | | F<br>3 compartments | | |
|---|---|---|---|---|---|---|---|---|
| | 42 | 43 | 44 | 45 | 46 | 47 | 48 | 49 |
| | | | | Dosage (g) | | | | |
| | 34.0 | 3.5 | 3.5 | 30.0 | 5.0 | 25.0 | 1.5 | 4.0 |
| Ingredients | | | | Weight % | | | | |
| Brightener | 0.2 | 0.2 | 0.2 | 0.3 | | 0.3 | | |
| Microcapsules* | 0.4 | 1.2 | 1.5 | 1.3 | 1.3 | 0.4 | 0.12 | 0.2 |
| Water | 9 | 8.5 | 10 | 5 | 11 | 10 | 10 | 9 |
| CaCl2 | | | | | | | 0.01 | |
| Perfume | 1.7 | 1.7 | | 0.6 | | 1.5 | 0.5 | |
| Minors (antioxidant, sulfite, aesthetics, . . .) | 2.0 | 2.0 | 2.0 | 4.0 | 1.5 | 2.2 | 2.2 | 2.0 |
| Buffers (sodium carbonate, monoethanolamine) [3] | | | | To pH 8.0 for liquids<br>To RA > 5.0 for powders | | | | |
| Solvents (1,2 propanediol, ethanol), Sulfate | | | | To 100 p | | | | |

[1] Polyethylenimine (MW = 600) with 20 ethoxylate groups per —NH.
[2] RA = Reserve Alkalinity (g NaOH/dose)
*Microcapsule added as 25-35% active slurry (aqueous solution). Core/wall ratio can range from 80/20 up to 90/10 and average particle diameter can range from 5 μm to 50 μm, and can be purified via any of the aforementioned examples. Suitable combinations of the microcapsules provided in Examples 1 through 21.
**Low water liquid detergent in Polyvinylalcohol unidose/sachet

Example 34. Centrifugation of PMC Slurry 14 milliliters of the aqueous suspension of perfume microcapsules of Example 2 are placed in a 20 milliliter centrifuge tube. 6 identical such tubes are prepared and placed in a batch centrifuge (IEC Centra CL2). After 20 minutes at 3800 RPM, the centrifuge tubes are removed. The top microcapsule layer is isolated from the remaining material. This material contains approximately 20 wt % water, and can be incorporated into low water containing formulations.

Example 35. Higher Density Capsules

Microcapsules are prepared by the same procedure as in Example 5 except that the Fragrance Oil is formulated with Scent A and Brominated Vegetable Oil (Virginia Dare Extract Co.) prior to preparation of first and second oil solutions. The table below provides the total mass of fragrance oil by its components—Scent A fragrance and brominated vegetable oil (density 1.33 g/mL) density modifier, along with the properties of the microcapsules.

| Example | Mass of Scent A in Fragrance Oil | Mass of Brominated Vegetable Oil in Fragrance Oil | Median Particle Size (microns) | Broadness Index |
|---|---|---|---|---|
| 33 | 112.50 | 75.00 | 11.81 | 1.28 |

To 90.0 grams of shampoo formulation (with a typical formulation given below) is added 2.33 grams of microcapsules (21.5 wt % Scent A oil) and 7.67 grams of deionized water to deliver a Scent A fragrance usage level of 0.5 wt %. The microcapsules and water are added on top of the shampoo formulation, then the contents are mixed using a SpeedMixer by Hauschild DAC 400FVZ mixer, at 1850 RPM for 1 minute.

A portion of this product is used to treat hair switches for in-vitro testing, using the Olfactive Analysis of Shampoo test method. The following results are obtained.

| Example | Level of density modifier | % Scent A Fragrance in Capsule Slurry | Quantity of Shampoo Product (g) | Quantity of Fragrance Delivery Technology (g) | Quantity of Water (g) | Olfactive Performance - Initial Pre-Comb/Post-Comb | Olfactive Performance - 24 hr Aged Pre-Comb/Post-Comb |
|---|---|---|---|---|---|---|---|
| Neat Perfume | 0% | N/A | 90.00 | 0.50 | 9.50 | 15/20 | 5/10 |
| 5 | 40% | 30.67% | 90.00 | 1.63 | 8.37 | 20/25 | 5/25 |
| 33 | 40% | 21.50% | 90.00 | 2.33 | 7.67 | 40/60 | 5/35 |

Notice that the higher density particles with brominated vegetable oil density modifier are able to deliver a substantially better initial and aged olfactive performance.

The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising an adjunct ingredient and, based on total composition weight, from about 0.1% to about 50%, of particles, wherein the particles have a median particle size of from about 5 microns to about 56 microns, wherein the particles comprise:
   a) a core comprising, based on total particle weight,
      from about 6% to about 99.9% of a benefit agent, wherein the benefit agent comprises perfume, and
      from about 0.1% to about 94% of a partitioning modifier comprising an oil soluble material that has a ClogP greater than about 4,
      wherein the benefit agent and the partitioning modifier are different materials; and
   b) a shell that encapsulates said core, said shell comprising, based on total shell weight, from about 50% to about 100% a polyacrylate,
      wherein the polyacrylate is formed, at least in part, from a multifunctional acrylate monomer and/or a multifunctional acrylate oligomer,
         wherein the multifunctional acrylate monomer and/or the multifunctional acrylate oligomer is a hexafunctional acrylate oligomer, and
   wherein the particles are characterized by a core/shell weight ratio of 80/20 to 90/10.

2. The composition of claim 1, wherein the hexafunctional acrylate oligomer is a hexafunctional aromatic acrylate oligomer.

3. The composition of claim 2, wherein the hexafunctional aromatic acrylate oligomer is a hexafunctional aromatic urethane acrylate oligomer.

4. The composition of claim 1, wherein the polyacrylate is further formed, at least in part, from an amine acrylate monomer, an amine methacrylate monomer, or a mixture thereof.

5. The composition of claim 4, wherein the polyacrylate is further formed, at least in part, from a carboxylic acid acrylate monomer, a carboxylic acid methacrylate monomer, or a mixture thereof.

6. The composition of claim 1, wherein the polyacrylate is further formed, at least in part, from a carboxylic acid acrylate monomer, a carboxylic acid methacrylate monomer, or a mixture thereof.

7. The composition of claim 1, wherein the particles further comprise a coating material.

8. The composition of claim 1, wherein the particles independently have a particle size of from about 2 microns to about 80 microns.

9. The composition of claim 1, wherein the particles have a median particle size of from about 7 microns to about 30 microns.

10. The composition of claim 1, wherein the particles have a median particle size of from about 10 microns to about 27 microns.

11. The composition of claim 1, wherein the adjunct ingredient comprises member selected from the group consisting of a humectant, a suspending agent, a dye, a pigment, and mixtures thereof.

12. The composition of claim 1, wherein the composition further comprises a member selected from the group consisting of a pH adjusting agent, a antimicrobial agent, an antifoam agent, a surfactant, a clay, a rheology modifier, a deposition aid, and mixtures thereof.

13. The composition of claim 1, wherein the composition further comprises surfactant.

14. The composition of claim 1, wherein the composition is a fabric care composition.

15. The composition of claim 1, wherein the composition is a fluid composition.

16. The composition of claim 1, wherein the composition is an aqueous liquid composition.

17. The composition of claim 1, wherein the composition is a detergent and is encapsulated by a water-soluble film to form a unit dose detergent.

* * * * *